US011759512B2

(12) United States Patent
D'Aoust et al.

(10) Patent No.: US 11,759,512 B2
(45) Date of Patent: Sep. 19, 2023

(54) MODIFIED NOROVIRUS VP1 PROTEINS AND VLPS COMPRISING MODIFIED NOROVIRUS VP1 PROTEINS

(71) Applicant: MEDICAGO INC., Quebec (CA)

(72) Inventors: Marc-Andre D'Aoust, Quebec (CA); Pierre-Olivier Lavoie, Quebec (CA)

(73) Assignee: MEDICAGO INC., Québec (CA)

( * ) Notice: Subject to any disclaimer, the term of this patent is extended or adjusted under 35 U.S.C. 154(b) by 157 days.

(21) Appl. No.: 17/259,789

(22) PCT Filed: Nov. 30, 2018

(86) PCT No.: PCT/CA2018/051529
§ 371 (c)(1),
(2) Date: Jan. 12, 2021

(87) PCT Pub. No.: WO2020/010428
PCT Pub. Date: Jan. 16, 2020

(65) Prior Publication Data
US 2021/0128714 A1 May 6, 2021

Related U.S. Application Data

(60) Provisional application No. 62/697,770, filed on Jul. 13, 2018.

(51) Int. Cl.
A61K 39/12 (2006.01)
C07K 14/085 (2006.01)
C12N 15/82 (2006.01)

(52) U.S. Cl.
CPC ............ A61K 39/12 (2013.01); C07K 14/085 (2013.01); C12N 15/82 (2013.01); C12N 2770/16023 (2013.01); C12N 2770/16034 (2013.01)

(58) Field of Classification Search
CPC ............ A61K 2039/5258; A61K 39/12; A61K 9/0019; C12N 2770/16023; C12N 2770/16022; C12N 15/8258; C12N 2770/16011; C12N 2770/16034; C12N 15/82; C12N 15/8257; A61P 31/14; C07K 14/005; C07K 14/085; C12P 21/02
See application file for complete search history.

(56) References Cited

U.S. PATENT DOCUMENTS

| 8,841,120 | B2 | 9/2014 | Richardson et al. |
| 9,518,096 | B2 | 12/2016 | Richardson et al. |
| 2013/0273105 | A1 | 10/2013 | Richardson et al. |
| 2014/0271712 | A1 | 9/2014 | Baric et al. |
| 2015/0023995 | A1 | 1/2015 | Richardson et al. |

FOREIGN PATENT DOCUMENTS

| WO | 2005/032457 A3 | 4/2005 | |
| WO | 2011/035422 A1 | 3/2011 | |
| WO | 2012/006293 A1 | 1/2012 | |
| WO | WO2014145245 A2 * | 9/2014 | ............ C07N 14/08 |
| WO | 2017/191264 A1 | 11/2017 | |
| WO | 2018/170603 A1 | 9/2018 | |

OTHER PUBLICATIONS

Bertolotti-Ciarlet et al., "The 3' End of Norwalk Virus mRNA Contains Determinants That Regulate the Expression and Stability of the Viral Capsid Protein VP1: a Novel Function for the VP2 Protein", Journal of Virology, 2003, vol. 77, Issue 21, pp. 11603-11615 (27 pages total).
Huo et al., "Chimeric VLPs with GII.3 P2 domain in a backbone of GII.4 VP1 confers novel HBGA binding ability", Virus Research, 2016, vol. 224, pp. 1-5 (5 pages total).
Tacket et al., "Human Immune Responses to a Novel Norwalk Virus Vaccine Delivered in Transgenic Potatoes", The Journal of Infectious Diseases, 2000, vol. 182, pp. 302-305 (4 pages total).
Huang et al., "A DNA Replicon System for Rapid High-Level Production of Virus-Like Particles in Plants", Biotechnology and Bioengineering, 2009, vol. 103, No. 4, pp. 706-714 (9 pages total).
Ben-Bassat et al., "Processing of the Initiation Methionine from Proteins: Properties of the *Escherichia coli* Methionine Aminopeptidase and Its Gene Structure", Journal of Bacteriology, 1987, vol. 169, No. 2, pp. 751-757 (7 pages total).
O'Regan et al., "Cloning and nucleotide sequence of the phosphoenolpyruvate carboxylase-coding gene of *Corynebacterium glutamicum* ATCC13032", Gene, 1989, vol. 77, pp. 237-251 (15 pages total).
Hochuli et al., "Genetic Approach to Facilitate Purification of Recombinant Proteins with a Novel Metal Chelate Adsorbent", Biotechnology, Nov. 1988, pp. 1321-1325 (5 pages total).
Sahin-Toth et al., "Cysteine scanning mutagenesis of the N-terminal 32 amino acid residues in the lactose permease of *Escherichia coli*", Protein Science, 1994, vol. 3, pp. 240-247 (8 pages total).
Parra et al., "Identification of a Broadly Cross-Reactive Epitope in the Inner Shell of the Norovirus Capsid", PLOS ONE, Jun. 2013, vol. 8, Issue 6, e67592, pp. 1-7 (7 pages total).
Motoya et al., "Molecular Evolution of the VP1 Gene in Human Norovirus GII.4 Variants in 1974-2015", Frontiers in Microbiology, Dec. 2017, vol. 8, Article 2399, pp. 1-17 (17 pages total).
Souza et al., "Expression and assembly of Norwalk virus-like particles in plants using a viral RNA silencing suppressor gene", Appl Microbiol Biotechnol, 2013, vol. 97, pp. 9021-9027 (7 pages total).
GenBank, capsid protein, partial [*Norovirus* sp.], APY24054.1, Feb. 4, 2017 (1 page total).
Hansman et al., "Genetic and antigenic diversity among noroviruses", Journal of General Virology, 2006, vol. 87, pp. 909-919 (11 pages total).

(Continued)

Primary Examiner — Bao Q Li
(74) Attorney, Agent, or Firm — Sughrue Mion, PLLC

(57) ABSTRACT

Nucleic acids encoding modified norovirus VP1 proteins, and VLPs comprising one or more of the modified norovirus VP1 proteins are provided. Methods for modified norovirus VP1 protein, and norovirus VLP, production in plants, portions of the plant or a plant cell, are also described.

22 Claims, 63 Drawing Sheets
Specification includes a Sequence Listing.

(56) References Cited

OTHER PUBLICATIONS

Vongpunsawad et al., "Norwalk Virus Minor Capsid Protein VP2 Associates within the VP1 Shell Domain", Journal of Virology, 2013, vol. 87, No. 9, pp. 4818-4825 (8 pages total).

Hugh S. Mason et al., "Expression of Norwalk virus capsid protein in transgenic tobacco and potato and its oral immunogenicity in mice", Proc. Natl. Acad. Sci., 1996, vol. 93, pp. 5335-5340 (6 pages total).

"VP1 [Norovirus GII]", GenBank: AWR17495.1, 2018 (2 pages total).

* cited by examiner

Figure 5A

Amino acid sequence of GII.4/Sydney/2012/K4LM89 (GII.4/2012; SEQ ID NO: 1)

MKMASSDANPSDGSAANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSRNYTMNLASQNWNDYDPTEEIPAPLGTPDFVGKIQG
VLTQTTRTDGSTRGHKATVYTGSADFAPKLGRVQFETDTDRDFEANQNTKFTPVGVIQDGGTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

Figure 5B

Nucleic acid sequence of Hu cod VP1 GII.4/Sydney/2012/K4LM89 (GII.4/2012; SEQ ID NO:2)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCCCATTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTCTAC
CACTACAATCAATCCAATGATCCGACCATTAAACTCATCGCGATGTTGTACACCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCCGAACCAAGCCCTTTAGTGTCCCCGTACTCACAGTCGAGGAGATGACAAATAGCCGCTTTCCAATCCCCCTTGAGAAACTG
TTCACAGGACCTTCCTCGGCATTCGTGGTTCAGCCACAGAACGGACGCTGCACAACTGACGGCGTGCTGCTCGGAACCACCCA
GCTTAGCCCTGTTAATATCTGTACGTTTAGAGGCGACGTAACTCACATAACTGGCTCACGGAACTATACCATGAATCTGGCAT
CACAGAATTGGAATGACTACGACCCAACCGAAGAGATTCCCGCACCTCTTGGAACCCCCGACTTTGTGGGAAAAATACAGGGC
GTCCTGACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCTGTAGGAG
TGATTCAGGACGGGGGCACCACTCACCGGAACGAGCCGCAACAATGGGTCCTGCCCTCTTATAGCGGGAGGAATACTCATAAT
GTGCATTTGGCTCCTGCAGTGGCTCCCACGTTTCCCGGGGAACAACTGCTCTTTTTCGTTCAACCATGCCTGGATGCTCCGG
ATATCCCAATATGGATCTCGATTGCCTGCTCCCACAGGAATGGGTGCAGTATTTTTATCAAGAGGCCGCACCAGCCCAATCCG
ACGTCGCACTTCTGCGGTTCGTGAATCCAGACACAGGCCGCGTGTTGTTTGAGTGCAAATTGCACAAATCAGGATACGTTACA
GTGGCTCATACTGGACAGCATGACCTGGTGATCCCACCCAACGGATATTTTAGGTTCGACTCCTGGGTGAATCAGTTTTATAC
ATTAGCCCCCATGGGGAATGGGACTGGCAGACGCAGGGCTGTCTGA

Figure 5C

Amino acid sequence of VP1 Hu/GII.4/Sydney/2015 (GII.4/2015; SEQ ID NO: 3)

MKMASSDANPSDGSAANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

Figure 5D

Nucleic acid sequence of Hu cod VP1 Hu/GII.4/Sydney/2015 (GII.4/2015; SEQ ID NO:4)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATACGTAACAACT
TGTTCAGGCCCCGGTGGAGAGTTTACAGTCAGCCCAAGAAACGCTCCTGGAGAGATACTGTGGAGCGCCCCACTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGCGATGTTACACATATCACTGGTTCTCACAACTATACTATGAACCTGGCCA
GCCGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 5E

Schematic representation of construct 4153 (VP1 GII.4/2015)

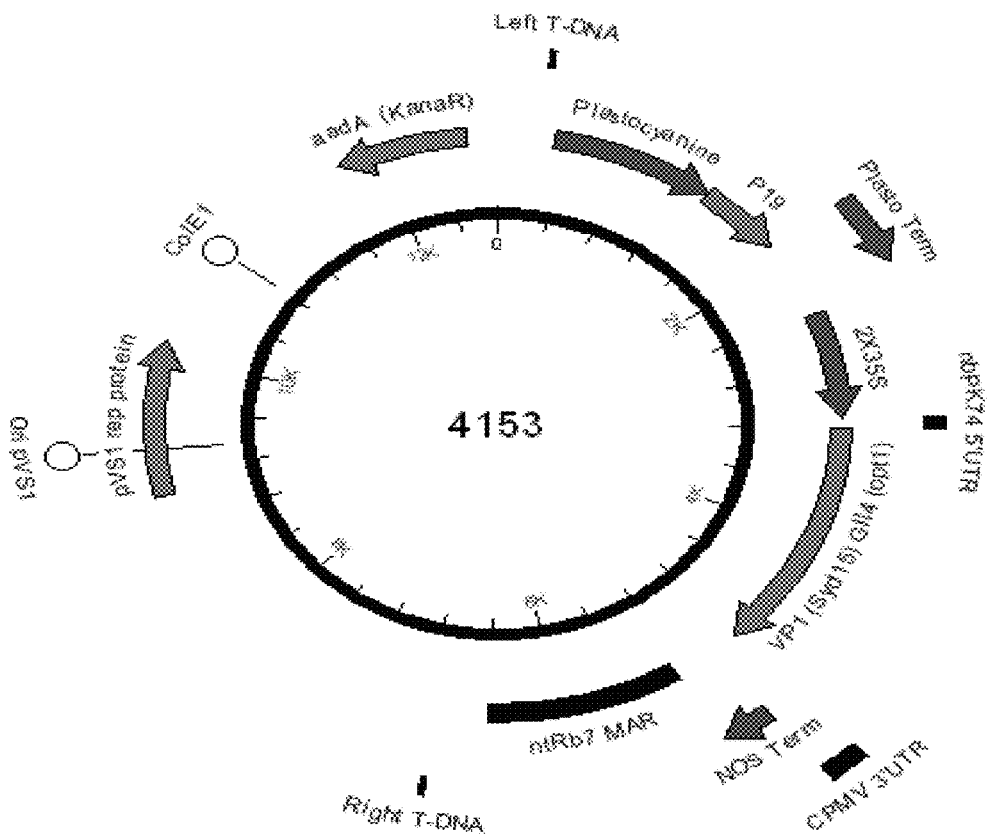

Figure 6A

Amino acid sequence of VP1 US96: GII.4/Dresden174/1997/DE_AY741811 (SEQ ID NO: 5)

```
MKMASNDANPSDGSTANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKVIFAAVPPNFPTEGLSPSQVTMFPHIIVDVRQLEPVLIPLPDVRNNFY
HYNQSNDSTIKLIAMLYTPLKANNAGDDVFTVSCRVLTRPSPDFDFIFLVPPTVESRTKPFTVPILTVEEMSNSRFPIPLEKL
YTGPSSAFVVQPQNGRCTTDGVLLGTTQLSAVNICTFRGDVTHIAGSHDYTMNLASQNWNNYDPTEEIPAPLGTPDFVGKIQG
MLTQTTREDGSTRAHKATVSTGSVHFTPKLGSVQYTTDTNNDFQTGQNTKFTPVGVIQDGNNHQNEPQQWVLPNYSGRTGHNV
HLAPAVAPTFPGEQLLFFRSTMPGCSGYPNMNLDCLLPQEWVQHFYQEAAPAQSDVALLRFVNPDTGRVLFECKLHKSGYVTV
AHTGPHDLVIPPNGYFRFDSWVNQFYTLAPMGNGAGRRRAL
```

Figure 6B

Amino acid sequence of VP1 FH02: GII.4/FarmingtonHills/2002/US_AY502023 (SEQ ID NO: 6)

```
MKMASNDANPSDGSTANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKIIFAAVPPNFPTEGLSPSQVTMFPHIIVDVRQLEPVLIPLPDVRNNFY
HYNQLNDPTIKLIAMLYTPLRANNAGEDVFTVSCRVLTRPSPDFDFIFLVPPTVESRTKPFTVPILTVEEMTNSRFPIPLEKL
FTGPSGAFVVQPQNGRCTTDGVLLGTTQLSPVNICTFRGDVTHIAGTHNYTMNLASQNWNNYDPTEEIPAPLGTPDFVGRIQG
MLTQTTRGDGSTRGHKATVSTGDVHFTPKLGSIQFNTDTNNDFETGQNTKFTPVGVVQDGNGTHQNEPQQWVLPSYSGRTGHN
VHLAPAVAPTFPGEQLLFFRSTMPGCSGYPNMNLDCLLPQEWVQHFYQEAAPAQSDVALLRFVNPDTGRVLFECKLHKSGYVT
VAHTGQHDLVIPPNGYFRFDSWVNQFYTLAPMGNGTGRRRAL
```

Figure 6C

Amino acid sequence of VP1 Hnt04:GII.4/Hunter-NSW504D/2004/AU_DQ078814 (SEQ ID NO: 7)

```
MKMASNDATPSDGSTANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKIIFAAVPPNFPTEVLSPSQVTMFPHIIVDVRQLEPVLIPLPDVRNNLY
HYNQSNDPTIRLIAMLYTPLRANNAGDDVFTVSCRVLTRPSPDFDFIFLVPPTVESRTKPFSVPILTVEEMTNSRFPIPLEKL
FTGPSSAFVVQPQNGRCTTDGVLLGTTQLSPVNICTFRGDVTHIAGTQNYTMNLASQNWNNYDPTEEIPAPLGTPDFVGRIQG
VLTQTTRRDGSTRGHKATVSTGSVHFTPKLGSVQFSTDTSNDFETGQNTRFTPVGVQDGSTTHQNEPQQWVLPDYSGRDSHN
VHLAPAVAPTFPGEQLLFFRSTMPGCSGYPNMNLDCLLPQEWVQHFYQESAPAQSDVALLRFVNPDTGRVLFECKLHKSGYVT
VAHTGQHDLVIPPNGYFRFDSWVNQFYTLAPMGNGAGRRRAL
```

Figure 6D

Amino acid sequence of VP1 2006b: GII.4/Shellharbour-NSW696T/2006/AU_EF684915 (SEQ ID NO: 8)

```
MKMASNDANPSDGSAANLVPEVNNEVMALEPVVGAAIAAPVAGQQNVIDPWIRNNFVQAPGGEFTVSPRNAPGEILWSAPLGP
DLNPYLSHLARMYNGYAGGFEVQVILAGNAFTAGKIIFAAVPPNFPTEGLSPSQVTMFPHIIVDVRQLEPVLIPLPDVRNNFY
HYNQSNDSTIKLIAMLYTPLRANNAGEDVFTVSCRVLTRPSPDFDFIFLVPPTVESRTKPFTVPILTVEEMTNSRFPIPLEKL
FTGPSGAFVVQPQNGRCTTDGVLLGTTQLSPVNICTFRGDVTHIAGSRNYTMNLASLKWNKYDPTEEIPAPLGTPDFVGKIQG
VLTQTTKGDGSTRGHKATIYTGSAPFTPKLGSVQFSTDTENDFETHQNTKFTPVGVTQDGSTTHRNEPQQWVLPSYSGRNVHN
VHLAPAVAPTFPGEQLLFFRSTMPGCSGYPNMDLDCLLPQEWVQHFYQEAAPAQSDVALLRFVNPDTGRVLFECKLHKSGYVT
VAHTGQHDLVIPPNGYFRFDSWVNQFYTLAPMGNGTGRRRAL
```

Figure 6E

Amino acid sequence of VP1 NO09: GII.4/Orange-NSW001P/2008/AU_GQ845367 (SEQ ID NO: 9)

MKMASSDANPSDGSTANLVPEVNNEVMALEPVVGAAIAAPVAGQQNVIDPWIRNNFVQAPGGEFTVSPRNAPGEILWSAPLGP
DMNPYLSHLARMYNGYAGGFEVQVILAGNAFTAGKIIFAAVPPNFPTEGLSPSQVTMFPHIIVDVRQLEPVLIPLPDVRNNFY
HYNQSNDPTIKLIAMLYTPLRANNAGDDVFTVSCRVLTRPSPDFDFIFLVPPTVESRTKPFSVPILTVEEMTNSRFPIPLEKL
FTGPSSAFVVQPQNGRCTTDGVLLGTTQLSPVNICTFRGDVTHIAGSRNYTMNLASQNWNSYDPTEEIPAPLGTPDFVGKIQG
VLTQTTRTDGSTRGHKATVYTGSADFSPKLGRVQFATDTDNDFDANQNTKFTPVGVIQDGNTAHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAL

FIGURE 7A

Nucleic acid sequence of Hu cod VP1 GII.4/2012_P80S (SEQ ID NO:10)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTCTAC
CACTACAATCAATCAATGATCCGACCATTAAACTCATCGCGATGTTGTACACCCTCTGCGCGCTAACAATGCTGGAGACGA
CGTATTCACCGTGTCATGCAGAGTGCTCACGAGACCTTCACCAGACTTTGCATTTATCTTCTTAGTGCCCCCCACTGTTGAGA
GCCGAACCAAGCCCTTTAGTGTCCCCGTACTCACAGTCGAGGAGATGACAAATAGCCGCTTCCAATCCCCCTTGAGAAACTG
TTCACAGGACCTTCCTCGGCATTCGTGGTTCAGCCACAGAACGGACGCTGCACAACTGACGGCGTGCTGCTCGGAACCACCCA
GCTTAGCCCTGTTAATATCTGTACGTTTAGAGGCGACGTAACTCACATAACTGGCTCACGGAACTATACCATGAATCTGGCAT
CACAGAATTGGAATGACTACGACCCAACCGAAGAGATTCCCGCACCTCTTGGAACCCCCGACTTTGTGGGAAAAATACAGGGC
GTCCTGACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCTGTAGGAG
TGATTCAGGACGGGGGCACCACTCACCGGAACGAGCCGCAACAATGGGTCCTGCCCTCTTATAGCGGGAGGAATACTCATAAT
GTGCATTTGGCTCCTGCAGTGGCTCCCACGTTTCCGGGGAACAACTGCTCTTTTTTCGTTCAACCATGCCTGGATGCTCCGG
ATATCCCAATATGGATCTCGATTGCCTGCTCCCACAGGAATGGGTGCAGTATTTTTATCAAGAGGCCGCACCAGCCCAATCCG
ACGTCGCACTTCTGCGGTTCGTGAATCCAGACACAGGCCGCGTGTTGTTTGAGTGCAAATTGCACAAATCAGGATACGTTACA
GTGGCTCATACTGGACAGCATGACCTGGTGATCCCACCCAACGGATATTTTAGGTTCGACTCCTGGGTGAATCAGTTTTATAC
ATTAGCCCCCATGGGGAATGGGACTGGCAGACGCAGGGCTGTCTGA

FIGURE 7B

Amino acid sequence of VP1 GII.4/2012_P80S (SEQ ID NO:11)

MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSRNYTMNLASQNWNDYDPTEEIPAPLGTPDFVGKIQG
VLTQTTRTDGSTRGHKATVYTGSADFAPKLGRVQFETDTDRDFEANQNTKFTPVGVIQDGGTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 7C

Schematic representation of construct 4152 (VP1 GII.4/2012_P80S)

FIGURE 7D

Nucleic acid sequence of Hu cod VP1 GII.4/2015_P80S (SEQ ID NO:12)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
```

Figure 7D (continued)

```
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 7E

Amino acid sequence of VP1 GII.4/2015_P80S (SEQ ID NO:13)

```
MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 7F

Schematic representation of construct 4154 (VP1 GII.4/2015_P80S)

FIGURE 7G

Nucleic acid sequence of Hu cod VP1 S(GII.4/2012_P80S) + P(GII.4/2015) (SEQ ID NO:14)

```
ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 7H

Amino acid sequence of VP1 S(GII.4/2012_P80S) + P(GII.4/2015) (SEQ ID NO:15)

```
MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 7I

Schematic representation of construct 4171 (VP1 S(GII.4/2012_P80S) + P(GII.4/2015))

FIGURE 8A

Nucleic acid sequence of Hu cod VP1 S(GII.4/2012_P80S) + P(GII.4/2015_M333V) (SEQ ID NO:16)

```
ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCGACCATTAAACTCATCGCGATGTTGTACACCCCTCTGCGCGCTAACAATGCTGGAACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
```

Figure 8A (continued)

AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 8B

Amino acid sequence of VP1 S(GII.4/2012_P80S) + P(GII.4/2015_M333V) (SEQ ID NO:17)

MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 8C

Schematic representation of construct 4174 (VP1 S(GII.4/2012_P80S) + P(GII.4/2015_M333V))

FIGURE 8D

Nucleic acid sequence of Hu cod VP1 S(GII.4/2012_P80S) + P(GII.4/2015_Q368E) (SEQ ID NO:18)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGAAAGATCCAGGGC
ATGCTGACACAGACGACAAAGACAGATGGTTCAACAAGAGGTCACAAAGCTACTGTTTACACCGGCTCTGCCGATTTCGCACC

Figure 8D (continued)

```
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 8E

Amino acid sequence of VP1 S(GII.4/2012_P80S) + P(GII.4/2015_ Q368E) (SEQ ID NO:19)

```
MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 8F

Schematic representation of construct 4176 (VP1 S(GII.4/2012_P80S) + P(GII.4/2015_ Q368E))

FIGURE 8G

Nucleic acid sequence of Hu cod VP1 S(GII.4/2012_P80S) + P(GII.4/2015_M333V+Q368E) (SEQ ID NO:20)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTCTTCCGCTCTACAATGCCCGGGTGCTCTGG
ATACCCAAATATGGATCTGGACTGCCTCCTGCCGCAAGAATGGGTGCAGTATTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 8H

Amino acid sequence of VP1 S(GII.4/2012_P80S) + P(GII.4/2015_ M333V+Q368E) (SEQ ID NO:21)

MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 8I

Schematic representation of construct 4187 (VP1 S(GII.4/2012_P80S)+P(GII.4/2015_ M333V+Q368E))

FIGURE 9A

Nucleic acid sequence of Hu cod VP1 S(GII.4/2012_A39V+P80S) + P(GII.4/2015_M333V) (SEQ ID NO:22)

```
ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCCTCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
```

Figure 9A (continued)

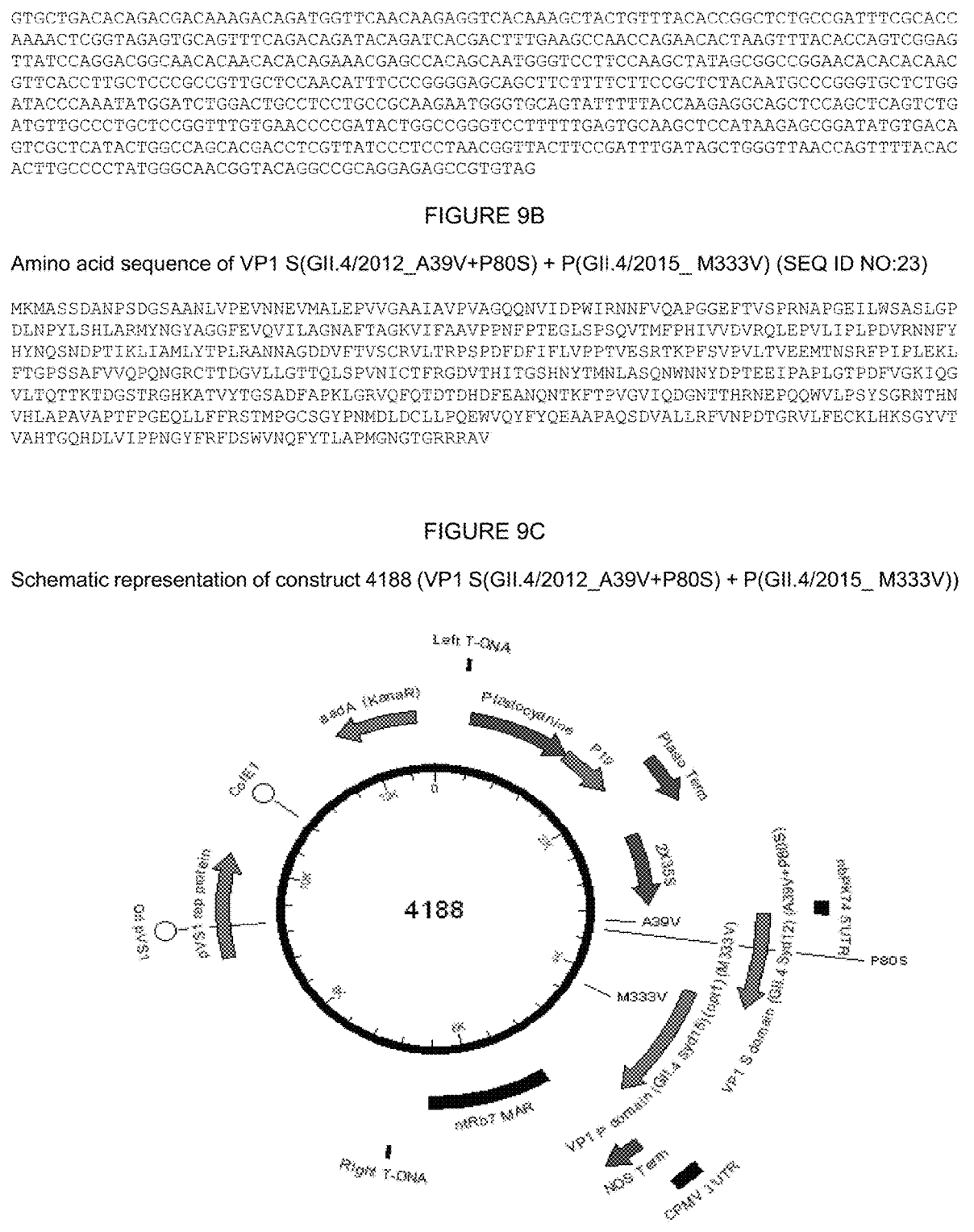

```
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCAC

FIGURE 9D

Nucleic acid sequence of Hu cod VP1 S(GII.4/2012_A39V+P80S) + P(GII.4/2015_Q368E) (SEQ ID NO:24)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 9E

Amino acid sequence of VP1 S(GII.4/2012_A39V+P80S) + P(GII.4/2015_ Q368E) (SEQ ID NO:25)

MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 9F

Schematic representation of construct 4194 (VP1 S(GII.4/2012_A39V+P80S)+P(GII.4/2015_Q368E))

FIGURE 9G

Nucleic acid sequence of Hu cod VP1 S(GII.4/2012_A39V+P80S) + P(GII.4/2015_M333A+Q368E) (SEQ ID NO:26)

```
ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATACGCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
```

Figure 9G (continued)

```
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 9H

Amino acid sequence of VP1 S(GII.4/2012_A39V+P80S) + P(GII.4/2015_ M333V+Q368E) (SEQ ID NO:27)

```
MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 9I

Schematic representation of construct 4191 (VP1 S(GII.4/2012_A39V+P80S) + P(GII.4/2015_ M333V+Q368E))

FIGURE 10A

Nucleic acid sequence of Hu cod VP1 S(GII.4/2012_R53I+P80S) + P(GII.4/2015_M333V) (SEQ ID NO:28)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTCTTCCGCTCTACAATGCCCGGGTGCTCTGG
ATACCCAAATATGGATCTGGACTGCCTCCTGCCGCAAGAATGGGTGCAGTATTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 10B

Amino acid sequence of VP1 S(GII.4/2012_R53I+P80S) + P(GII.4/2015_M333V) (SEQ ID NO:29)

MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 10C

Schematic representation of construct 4189 (VP1 S(GII.4/2012_R53I+P80S) + P(GII.4/2015_M333V))

FIGURE 10D

Nucleic acid sequence of Hu cod VP1 S(GII.4/2012_R53I+P80S) + P(GII.4/2015_Q368E) (SEQ ID NO:30)

```
ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGCACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
```

Figure 10D (continued)

ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 10E

Amino acid sequence of VP1 S(GII.4/2012_R53I+P80S) + P(GII.4/2015_ Q368E) (SEQ ID NO:31)

MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 10F

Scheamtic representation of construct 4195 (VP1 S(GII.4/2012_R53I+P80S) + P(GII.4/2015_Q368E))

FIGURE 10G

Nucleic acid sequence of Hu cod VP1 S(GII.4/2012_R53I+P80S) + P(GII.4/2015_M333V+Q368E) (SEQ ID NO:32)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGCGCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 10H

Amino acid sequence of VP1 S(GII.4/2012_R53I+P80S) + P(GII.4/2015_ M333V+Q368E) (SEQ ID NO:33)

MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 10I

Schematic representation of construct 4192 (VP1 S(GII.4/2012_R53I+P80S) + P(GII.4/2015_M333V+Q368E))

FIGURE 11A

Nucleic acid sequence of Hu cod VP1 S(GII.4/2012_A39V+R53I+P80S) + P(GII.4/2015_M333V) (SEQ ID NO:34)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA

Figure 11A (continued)

```
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACA

Schematic representation of construct 4190 (VP1 S(GII.4/2012_A39V+R53I+P80S) + P(GII.4/2015_M333V))

Nucleic acid sequence of Hu cod VP1 S(GII.4/2012_A39V+R53I+P80S) + P(GII.4/2015_Q368E) (SEQ ID NO:36)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC

Figure 11D (continued)

```
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 11E

Amino acid sequence of VP1 S(GII.4/2012_A39V+R53I+P80S) + P(GII.4/2015_Q368E) (SEQ ID NO:37)

```
MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 11F

Schematic representation of construct 4196 (VP1 S(GII.4/2012_A39V+R53I+P80S) + P(GII.4/2015_Q368E))

FIGURE 11G

Nucleic acid sequence of Hu cod VP1 S(GII.4/2012_A39V+R53I+P80S) + P(GII.4/2015_M333V+Q368E) (SEQ ID NO:38)

ATGAAAATGGCCTCGAGTGACGCTAACCCTAGTGACGGCAGCGCCGCCAATCTTGTGCCTGAGGTTAATAATGAGGTGATGGC
CCTGGAGCCTGTGGTGGGCGCAGCCATAGCAGTCCCCGTGGCCGGTCAGCAGAATGTGATTGACCCGTGGATAATCAACAATT
TTGTCCAAGCCCCTGGTGGGGAGTTCACCGTTAGCCCGAGAAATGCGCCAGGAGAAATCCTGTGGTCGGCCAGCTTGGGACCC
GATCTGAACCCCTATTTGTCACATCTCGCTCGGATGTACAACGGGTATGCCGGCGGATTTGAAGTGCAGGTGATTCTGGCTGG
GAACGCGTTCACTGCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACGCAATAATTTCTAC
CACTACAATCAATCCAATGATCCGACCATTAAACTCATCGCGATGTTGTACACCCCTCTGCGCGCTAACAATGCTGGAGACGA
CGTATTCACCGTGTCATGCAGAGTGCTCACCAGACCTTCACCAGACTTTGACTTTATCTTCTTAGTGCCCCCACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 11H

Amino acid sequence of VP1 S(GII.4/2012_A39V+R53I+P80S) + P(GII.4/2015_M333V+Q368E) (SEQ ID NO:39)

MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKVIFAAVPPNFPTEGLSPSQVTMFPHIVVDVRQLEPVLIPLPDVRNNFY
HYNQSNDPTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 11I

Schematic representation of construct 4193 (VP1 S(GII.4/2012_A39V+R53I+P80S) + P(GII.4/2015_M333V+Q368E)).

FIGURE 12A

Nucleic acid sequence of Hu cod VP1 GII.4/2015_P80S+M333V (SEQ ID NO:40)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATACGTAACAACT
TGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGTGCTCTGG
ATACCCAAATATGGATCTGGACTGCCTCCTGCCGCAAGAATGGGTGCAGTATTTTTACCAAGAGGCAGCTCCAGCTCAGTCTG
```

Figure 12A (continued)

```
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 12B

Amino acid sequence of VP1 GII.4/2015_P80S+M333V (SEQ ID NO:41)

```
MKMASSDANFSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 12C

Schematic representation of construct 4241 (VP1 GII.4/2015_P80S+M333V)

FIGURE 12D

Nucleic acid sequence of Hu cod VP1 GII.4/2015_P80S+Q368E (SEQ ID NO:42)

ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCTCTTATACCCCTGCCCGATGTCCGAAACAACTTCTAC
CACTATAATCAGAGCAACGACAGCACAATCAAGCTCATCGCTATGCTCTACACACCACTGAGAGCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 12E

Amino acid sequence of VP1 GII.4/2015_P80S+Q368E (SEQ ID NO:43)

MKMASSDANPSDGSAANLVPEVNNEVMALEPVVGAAIAAPVAGQQNVIDPWIRMNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 12F

Schematic representation of construct 4242 (VP1 GII.4/2015_P80S+Q368E)

FIGURE 12G

Nucleic acid sequence of Hu cod VP1 GII.4/2015_P80S+M333V+Q368E (SEQ ID NO:44)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATACGTAACAACT
TGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACAGAAGAGCCACAATGGGTCCTTCAAGCTATAGCGGCCGGAACACACAAC
GTTCACCTTGCTCCCGCCGTTGCTCCAACATTTCCGGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
```

Figure 12G (continued)

```
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 12H

Amino acid sequence of VP1 GII.4/2015_P80S+M333V+Q368E (SEQ ID NO:45)

```
MKMASSDANPSDGSAANLVPEVNNEVMALEPVVGAAIAAPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 12I

Schematic representation of construct 4243 (VP1 GII.4/2015_P80S+M333V+Q368E)

FIGURE 13A

Nucleic acid sequence of Hu cod VP1 GII.4/2015_A39V+P80S (SEQ ID NO:46)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCCTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 13B

Amino acid sequence of VP1 GII.4/2015_A39V+P80S (SEQ ID NO:47)

```
MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 13C

Schematic representation of construct 4244 (VP1 GII.4/2015_A39V+P80S)

FIGURE 13D

Nucleic acid sequence of Hu cod VP1 GII.4/2015_A39V+P80S+M333V (SEQ ID NO:48)

ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTACAACTATACTATGAACCTGGCCA
GCCAGAACTGGAACAACTACGACCCAACAGAGGAGATCCCTGCTCCACTTGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG

Figure 13D (continued)

```
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 13E

Amino acid sequence of VP1 GII.4/2015_A39V+P80S+M333V (SEQ ID NO:49)

```
MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 13F

Schematic representation of construct 4245 (VP1 GII.4/2015_A39V+P80S+M333V)

FIGURE 13G

Nucleic acid sequence of Hu cod VP1 GII.4/2015_A39V+P80S+Q386E (SEQ ID NO:50)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 13H

Amino acid sequence of VP1 GII.4/2015_A39V+P80S+Q386E (SEQ ID NO:51)

```
MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

Schematic representation of construct 4246 (VP1 GII.4/2015_A39V+P80S+Q386E)

FIGURE 13J

Nucleic acid sequence of Hu cod VP1 GII.4/2015_A39V+P80S+M333V+Q386E (SEQ ID NO:52)

ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATACGTAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 13K

Amino acid sequence of VP1 GII.4/2015_A39V+P80S+M333V+Q386E (SEQ ID NO:53)

MKMASSDANPSDGSAANLVPEVNNEVMALEPVVGAAIAVPVAGQQNVIDPWIRNNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 13L

Schematic representation of construct 4247 (VP1 GII.4/2015_A39V+P80S+M333V+Q386E

FIGURE 14A

Nucleic acid sequence of Hu cod VP1 GII.4/2015_R53I+P80S (SEQ ID NO:54)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATAATCAACAACT
TGTTCAGGCCCCCGGTGGAGAGTTTACAGTCAGCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
```

Figure 14A (continued)

```
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 14B

Amino acid sequence of VP1 GII.4/2015_R53I+P80S (SEQ ID NO:55)

```
MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 14C

Schematic representation of construct 4248 (VP1 GII.4/2015_R53I+P80S)

FIGURE 14D

Nucleic acid sequence of Hu cod VP1 GII.4/2015_R53I+P80S+M333V (SEQ ID NO:56)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATAATCAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 14E

Amino acid sequence of VP1 GII.4/2015_R53I+P80S+M333V (SEQ ID NO:57)

```
MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 14F

Schematic representation of construct 4249 (VP1 GII.4/2015_R53I+P80S+M333V)

FIGURE 14G

Nucleic acid sequence of Hu cod VP1 GII.4/2015_R53I+P80S+Q386E (SEQ ID NO:58)

ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATAATCAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG

FIGURE 14H

Amino acid sequence of VP1 GII.4/2015_R53I+P80S+Q386E (SEQ ID NO:59)

MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV

FIGURE 14I

Schematic representation of construct 4250 (VP1 GII.4/2015_R53I+P80S+Q386E)

FIGURE 14J

Nucleic acid sequence of Hu cod VP1 GII.4/2015_R53I+P80S+M333V+Q386E (SEQ ID NO:60)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGCTCCTGTTGCTGGGCAGCAGAACGTGATAGACCCATGGATAATCAACAACT
TGTTCAGGCCCCCGGTGGAGAGTTTACAGTCAGCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTACAACTATACTATGAACCTGGCCA
GCCAGAACTGGAACAACTACGACCCAACAGAGGAGATCCCTGCTCCACTTGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
```

Figure 14J (continued)

```
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 14K

Amino acid sequence of VP1 GII.4/2015_R53I+P80S+M333V+Q386E (SEQ ID NO:61)

```
MKMASSDANPSDGSAANLVPEVNNEVMALEPVVGAAIAAPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 14L

Schematic representation of construct 4251 (VP1 GII.4/2015_R53I+P80S+M333V+Q386E)

FIGURE 15A

Nucleic acid sequence of Hu cod VP1 GII.4/2015_A39V+R53I+P80S (SEQ ID NO:62)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATAATCAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
ATGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 15B

Amino acid sequence of VP1 GII.4/2015_A39V+R53I+P80S (SEQ ID NO:63)

```
MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

Schematic representation of construct 4252 (VP1 GII.4/2015_A39V+R53I+P80S)

Nucleic acid sequence of Hu cod VP1 GII.4/2015_A39V+R53I+P80S+M333V (SEQ ID NO:64)

ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATAATCAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC

Figure 15D (continued)

```
AAAACTCGGTAGAGTGCAGTTTCAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 15E

Amino acid sequence of VP1 GII.4/2015_A39V+R53I+P80S+M333V (SEQ ID NO:65)

```
MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFQTDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

Schematic representation of construct 4253 (of VP1 GII.4/2015_A39V+R53I+P80S+M333V)

Nucleic acid sequence of Hu cod VP1 GII.4/2015_A39V+R53I+P80S+Q386E (SEQ ID NO:66)

```
ATGAAGAT

Figure 15G (continued)

```
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 15H

Amino acid sequence of VP1 GII.4/2015_A39V+R53I+P80S+Q386E (SEQ ID NO:67)

```
MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
MLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 15I

Schematic representation of construct 4254 (VP1 GII.4/2015_A39V+R53I+P80S+Q386E)

FIGURE 15J

Nucleic acid sequence of Hu cod VP1 GII.4/2015_A39V+R53I+P80S+M333V+Q386E (SEQ ID NO:68)

```
ATGAAGATGGCTAGCTCAGACGCCAATCCAAGCGACGGTAGCGCTGCCAACCTCGTGCCCGAGGTCAACAACGAAGTTATGGC
CCTTGAGCCCGTGGTTGGAGCTGCTATAGCTGTGCCTGTTGCTGGGCAGCAGAACGTGATAGACCCATGGATAATCAACAACT
TTGTTCAGGCCCCCGGTGGAGAGTTTACAGTCAGCCCAAGAAACGCTCCTGGAGAGATACTGTGGAGCGCCTCCCTCGGCCCC
GACCTCAACCCCTATCTGTCACATCTCGCTCGCATGTATAACGGCTATGCTGGCGGTTTTGAAGTTCAGGTCATCCTTGCCGG
AAACGCCTTCACCGCTGGGAAGATAATCTTTGCTGCTGTCCCACCCAACTTTCCAACTGAGGGCCTGAGCCCAAGCCAGGTTA
CAATGTTTCCACACATGATAGTTGATGTCAGACAGCTGGAGCCAGTCCTTATACCCCTGCCCGATGTCCGAAACAACTTCTAC
CACTATAATCAGAGCAACGACAGCACAATCAAGCTCATCGCTATGCTCTACACACCACTGAGAGCCAACAACGCAGGAGATGA
CGTGTTACAGTGTCATGTAGAGTCCTCACAAGACCAAGCCCTGATTTTGATTTCATCTTCCTCGTGCCGCCAACTGTTGAGA
GCAGAACTAAGCCCTTTTCTGTTCCCGTGCTGACAGTTGAGGAAATGACAAATTCTAGATTTCCAATCCCCCTTGAAAAGCTG
TTTACGGGACCAAGCTCTGCCTTCGTGGTGCAGCCACAGAATGGTCGATGTACAACAGACGGCGTCCTGCTCGGTACAACACA
GCTCAGCCCTGTTAACATATGCACTTTTAGGGGCGATGTTACACATATCACTGGTTCTCACAACTATACTATGAACCTGGCCA
GCCAGAACTGGAACAACTACGACCCAACAGAGGAGATCCCTGCTCCACTTGGGACACCCGACTTTGTTGGAAAGATCCAGGGC
GTGCTGACACAGACGACAAAGACAGATGGTTCAACAAGAGGTCACAAAGCTACTGTTTACACCGGCTCTGCCGATTTCGCACC
AAAACTCGGTAGAGTGCAGTTTGAGACAGATACAGATCACGACTTTGAAGCCAACCAGAACACTAAGTTTACACCAGTCGGAG
TTATCCAGGACGGCAACACAACACACAGAAACGAGCCACAGCAATGGGTCCTTCCAAGCTATAGCGGCCGGAACACACACAAC
GTTCACCTTGCTCCCGCCGTTGCTCCAACATTTCCCGGGGAGCAGCTTCTTTCTTCCGCTCTACAATGCCCGGGTGCTCTGG
ATACCCAAATATGGATCTGGACTGCCTCCTGCCGCAAGAATGGGTGCAGTATTTTTACCAAGAGGCAGCTCCAGCTCAGTCTG
ATGTTGCCCTGCTCCGGTTTGTGAACCCCGATACTGGCCGGGTCCTTTTTGAGTGCAAGCTCCATAAGAGCGGATATGTGACA
GTCGCTCATACTGGCCAGCACGACCTCGTTATCCCTCCTAACGGTTACTTCCGATTTGATAGCTGGGTTAACCAGTTTTACAC
ACTTGCCCCTATGGGCAACGGTACAGGCCGCAGGAGAGCCGTGTAG
```

FIGURE 15K

Amino acid sequence of VP1 GII.4/2015_A39V+R53I+P80S+M333V+Q386E (SEQ ID NO:69)

```
MKMASSDANPSDGSAANLVPEVNNEVMALEPVVGAAIAVPVAGQQNVIDPWIINNFVQAPGGEFTVSPRNAPGEILWSASLGP
DLNPYLSHLARMYNGYAGGFEVQVILAGNAFTAGKIIFAAVPPNFPTEGLSPSQVTMFPHMIVDVRQLEPVLIPLPDVRNNFY
HYNQSNDSTIKLIAMLYTPLRANNAGDDVFTVSCRVLTRPSPDFDFIFLVPPTVESRTKPFSVPVLTVEEMTNSRFPIPLEKL
FTGPSSAFVVQPQNGRCTTDGVLLGTTQLSPVNICTFRGDVTHITGSHNYTMNLASQNWNNYDPTEEIPAPLGTPDFVGKIQG
VLTQTTKTDGSTRGHKATVYTGSADFAPKLGRVQFETDTDHDFEANQNTKFTPVGVIQDGNTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRVLFECKLHKSGYVT
VAHTGQHDLVIPPNGYFRFDSWVNQFYTLAPMGNGTGRRRAV
```

FIGURE 15L

Schematic representation of construct 4255 (VP1 GII.4/2015_A39V+R53I+P80S+M333V+Q386E)

FIGURE 16A

Nucleic acid sequence of Cloning vector 3674 from left to right T-DNA (SEQ ID NO:70)

```
TGGCAGGATATATTGTGGTGTAAACAAATTGACGCTTAGACAACTTAATAACACATTGCGGACGTTTTAATGTACTGAATTA
ACGCCGAATCCCGGGCTGGTATATTTATATGTTGTCAAATAACTCAAAAACCATAAAAGTTTAAGTTAGCAAGTGTGTACATT
TTTACTTGAACAAAAATATTCACCTACTACTGTTATAAATCATTATTAAACATTAGAGTAAAGAAATATGGATGATAAGAACA
AGAGTAGTGATATTTTGACAACAATTTTGTTGCAACATTTGAGAAAATTTTGTTGTTCTCTCTTTTCATTGGTCAAAAACAAT
AGAGAGAGAAAAGGAAGAGGGGAGAATAAAAACATAATGTGAGTATGAGAGAGAAAGTTGTACAAAAGTTGTACCAAAATAGT
TGTACAAATATCATTGAGGAATTTGACAAAAGCTACACAAATAAGGGTTAATTGCTGTAAATAAATAAGGATGACGCATTAGA
GAGATGTACCATTAGAGAATTTTTGGCAAGTCATTAAAAAGAAAGAATAAATTATTTTTAAAATTAAAAGTTGAGTCATTTGA
TTAAACATGTGATTATTTAATGAATTGATGAAAGAGTTGGATTAAAGTTGTATTAGTAATTAGAATTTGGTGTCAAATTTAAT
TTGACATTTGATCTTTTCCTATATATTGCCCCATAGAGTCAGTTAACTCATTTTTATATTTCATAGATCAAATAAGAGAAATA
ACGGTATATTAATCCCTCCAAAAAAAAAAAACGGTATATTTACTAAAAAATCTAAGCCACGTAGGAGGATAACAGGATCCCCG
TAGGAGGATAACATCCAATCCAACCAATCACAACAATCCTGATGAGATAACCCACTTTAAGCCCACGCATCTGTGGCACATCT
ACATTATCTAAATCACACATTCTTCCACACATCTGAGCCACACAAAAACCAATCCACATCTTTATCACCCATTCTATAAAAAA
TCACACTTTGTGAGTCTACACTTTGATTCCCTTCAAACACATACAAAGAGAAGAGACTAATTAATTAATTAATCATCTTGAGA
GAAAATGGAACGAGCTATACAAGGAAACGACGCTAGGGAACAAGCTAACAGTGAACGTTGGGATGGAGGATCAGGAGGTACCA
CTTCTCCCTTCAAACTTCCTGACGAAAGTCCGAGTTGGACTGAGTGGCGGCTACATAACGATGAGACGAATTCGAATCAAGAT
AATCCCCTTGGTTTCAAGGAAAGCTGGGGTTTCGGGAAAGTTGTATTTAAGAGATATCTCAGATACGACAGGACGGAAGCTTC
ACTGCACAGAGTCCTTGGATCTTGGACGGGAGATTCGGTTAACTATGCAGCATCTCGATTTTTCGGTTTCGACCAGATCGGAT
GTACCTATAGTATTCGGTTTCGAGGAGTTAGTATCACCGTTTCTGGAGGGTCGCGAACTCTTCAGCATCTCTGTGAGATGGCA
ATTCGGTCTAAGCAAGAACTGCTACAGCTTGCCCCAATCGAAGTGGAAAGTAATGTATCAAGAGGATGCCCTGAAGGTACTCA
AACCTTCGAAAAAGAAAGCGAGTAAGTTAAAATGCTTCTTCGTCTCCTATTTATAATATGGTTTGTTATTGTTAATTTTGTTC
TTGTAGAAGAGCTTAATTAATCGTTGTTGTTATGAAATACTATTTGTATGAGATGAACTGGTGTAATGTAATTCATTTACATA
AGTGGAGTCAGAATCAGAATGTTTCCTCCATAACTAACTAGACATGAAGACCTGCCGCGTACAATTGTCTTATATTTGAACAA
CTAAAATTGAACATCTTTTGCCACAACTTTATAAGTGGTTAATATAGCTCAAATATATGGTCAAGTTCAATAGATTAATAATG
GAAATATCAGTTATCGAAATTCATTAACAATCAACTTAACGTTATTAACTACTAATTTTATATCATCCCCTTTGATAAATGAT
AGTACACCAATTAGGAAGGAGCATGCTCGCCTAGGAGATTGTCGTTTCCCGCCTTCAGTTTGCAAGCTGCTCTAGCCGTGTAG
CCAATACGCAAACCGCCTCTCCCCGCGCGTTGGGAATTACTAGCGCGTGTCGACAAGCTTGCATGCCGGTCAACATGGTGGAG
CACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACCCCCACCC
ACGAGGAGCATCGTGGAAAAAGAAGACGTTCCAACCACGTCTTCAAAGCAAGTGGATTGATGTGATAACATGGTGGAGCACGA
CACACTTGTCTACTCCAAAAATATCAAAGATACAGTCTCAGAAGACCAAAGGGCAATTGAGACTTTTCAACAAAGGGTAATAT
CCGGAAACCTCCTCGGATTCCATTGCCCAGCTATCTGTCACTTTATTGTGAAGATAGTGGAAAAGGAAGGTGGCTCCTACAAA
TGCCATCATTGCGATAAAGGAAAGGCCATCGTTGAAGATGCCTCTGCCGACAGTGGTCCCAAAGATGGACCCCCACCCACGAG
GAGCATCGTGGAAAAGAAGACGTTCCAACCACGTCTTCAAAGCAAGTGGATTGATGTGATATCTCCACTGACGTAAGGGATG
ACGCACAATCCCACTATCCTTCGCAAGACCCTTCCTCTATATAAGGAAGTTCATTTCATTTGGAGAGGATAACAATTTAAACA
AACAAAATCAACAAATATAGAAAATAACGCATTTCCAATTCTTTGAAATTTCTGACGTCACTCCTCAGCCAAAACGACACCCC
CATCTGTCTATCCACTGGCCCCTGGATCTGCTGCCCAAACTAACTCCATGGTGACCCTGGGATGCCTGGTCAAGGGCTATTTC
CCTGAGCCAGTGACAGTGACCTGGAACTCTGGATCCCTGTCCAGCGGTGTGCACACCTTCCCAGCTGTCCTGCAGTCTGACCT
CTACACTCTGAGCAGCTCAGTGACTGTCCCCTCCAGCACCTGGCCCAGCGAGACCGTCACCTGCAACGTTGCCCACCCGGCCA
GCAGCACCAAGGTGGACAAGAAAATTGTGCCCAGGGATTGTGGTTGTAAGCCTTGCATATGTACAGTCCCAGAAGTATCATCT
GTCTTCATCTTCCCCCCAAAGCCCAAGGATGTGCTCACCATTACTCTGACTCCTAAGGTCACGTGTGTTGTGGTAGACATCAG
CAAGGATGATCCCGAGGTCCAGTTCAGCTGGTTTGTAGATGATGTGGAGGTGCACACAGCTCAGACGCAACCCCGGGAGGAGC
AGTTCAACAGCACTTTCCGCTCAGTCAGTGAACTTCCCATCATGCACCAGGACTGGCTCAATGGCAAGGAGCGATCGCTCACC
ATCACCATCACCATCACCATTAAAGGCCTATTTTCTTTAGTTTGAATTTACTGTTATTCGGTGTGCATTTCTATGTT
TGGTGAGCGGTTTTCTGTGCTCAGAGTGTGTTTATTTTATGTAATTTAATTTCTTTGTGAGCTCCTGTTTAGCAGGTCGTCCC
TTCAGCAAGGACACAAAAAGATTTTAATTTTATTATCGTTCAAACATTTGGCAATAAAGTTTCTTAAGATTGAATCCTGTTGC
CGGTCTTGCGATGATTATCATATAATTTCTGTTGAATTACGTTAAGCATGTAATAATTAACATGTAATGCATGACGTTATTTA
TGAGATGGGTTTTTATGATTAGAGTCCCGCAATTATACATTTAATACGCGATAGAAACAAAATATAGCGCGCAAACTAGGAT
AAATTATCGCGCGCGGTGTCATCTATGTTACTAGATCTCTAGGTAAAAATCCCAATTATATTTGGTCTAATTTAGTTTGGTAT
TGAGTAAAACAAATTCGAACCAAACCAAAATATAAATATATAGTTTTTATATATATGCCTTTAAGACTTTTTATAGAATTTTC
TTTAAAAAATATCTAGAAATATTTGCGACTCTTCTGGCATGTAATATTTCGTTAAATATGAAGTGCTCCATTTTTATTAACTT
TAAATAATTGGTTGTACGATCACTTTCTTATCAAGTGTTACTAAAATGCGTCAATCTCTTTGTTCTTCCATATTCATATGTCA
AATCTATCAAAATTCTTATATATCTTTTTCGAATTTGAAGTGAAATTTCGATAATTTAAAATTAAATAGAACATATCATTAT
TTAGGTATCATATTGATTTTTATACTTAATTACTAAATTTGGTTAACTTTGAAAGTGTACATCAACGAAAAATTAGTCAAACG
```

FIGURE 16A (continued)

```
ACTAAAATAAATAAATATCATGTGTTATTAAGAAAATTCTCCTATAAGAATATTTTAATAGATCATATGTTTGTAAAAAAAT
TAATTTTTACTAACACATATATTTACTTATCAAAAATTTGACAAAGTAAGATTAAAATAATATTCATCTAACAAAAAAAAAC
CAGAAAATGCTGAAAACCCGGCAAAACCGAACCAATCCAAACCGATATAGTTGGTTTGGTTTGATTTTGATATAAACCGAACC
AACTCGGTCCATTTGCACCCCTAATCATAATAGCTTTAATATTTCAAGATATTATTAAGTTAACGTTGTCAATATCCTGGAAA
TTTTGCAAAATGAATCAAGCCTATATGGCTGTAATATGAATTTAAAAGCAGCTCGATGTGGTGGTAATATGTAATTTACTTGA
TTCTAAAAAAATATCCCAAGTATTAATAATTTCTGCTAGGAAGAAGGTTAGCTACGATTTACAGCAAAGCCAGAATACAAAGA
ACCATAAAGTGATTGAAGCTCGAAATATACGAAGGAACAAATATTTTTAAAAAAATACGCAATGACTTGGAACAAAAGAAAGT
GATATATTTTTTGTTCTTAAACAAGCATCCCCTCTAAAGAATGGCAGTTTTCCTTTGCATGTAACTATTATGCTCCCTTCGTT
ACAAAAATTTTGGACTACTATTGGGAACTTCTTCTGAAAATTCTAGAGTCTCAAGCTTGGCGCGCCCACGTGACTAGTGGCAC
TGGCCGTCGTTTTACAACGTCGTGACTGGGAAAACCCTGGCGTTACCCAACTTAATCGCCTTGCAGCACATCCCCCTTTCGCC
AGCTGGCGTAATAGCGAAGAGGCCCGCACCGATCGCCCTTCCCAACAGTTGCGCAGCCTGAATGGCGAATGCTAGAGCAGCTT
GAGCTTGGATCAGATTGTCGTTTCCCGCCTTCAGTTTAAACTATCAGTGTTTGACAGGATATATTGGCGGGTAAACCTAAGAG
AAAAGAGCGTTTA
```

FIGURE 16B

Schematic of construct 3674.

FIGURE 16C

Nucleic acid sequence of Construct 4153 from 2X35S promoter to NOS terminator (SEQ ID NO:71)

```
GTCAACATGGTGGAGCACGACACACTTGTCTACTCCAAAAATATCAAAGATACAGTCTCAGAAGACCAAAGGGCAATTGAGAC
TTTTCAACAAAGGGTAATATCCGGAAACCTCCTCGGATTCCATTGCCCAGCTATCTGTCACTTTATTGTGAAGATAGTGGAAA
AGGAAGGTGGCTCCTACAAATGCCATCATTGCGATAAAGGAAAGGCCATCGTTGAAGATGCCTCTGCCGACAGTGGTCCCAAA
GATGGACCCCACCCACGAGGAGCATCGTGGAAAAGAAGACGTTCCAACCACGTCTTCAAAGCAAGTGGATTGATGTGATAA
CATGGTGGAGCACGACACACTTGTCTACTCCAAAAATATCAAAGATACAGTCTCAGAAGACCAAAGGGCAATTGAGACTTTTC
AACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGG
ACCCCACCCACGAGGAGCATCGTGGAAAAGAAGACGTTCCAACCACGTCTTCAAAGCAAGTGGATTGATGTGATATCTCCA
CTGACGTAAGGGATGACGCACAATCCCACTATCCTTCGCAAGACCCTTCCTCTATATAAGGAAGTTCATTTCATTTGGAGAGG
ATAACAATTTAAACAAACAAAATCAACAAATATAGAAAATAACGCATTTCCAATTCTTTGAAATTTCTGCAACAATGAAGATG
GCTAGCTCAGACGCCAATCCAAGCGACGGTAGCGCTGCCAACCTCGTGCCCGAGGTCAACAACGAAGTTATGGCCCTTGAGCC
CGTGGTTGGAGCTGCTATAGCTGCTCCTGTTGCTGGGCAGCAGAACGTGATAGACCCATGGATACGTAACAACTTTGTTCAGG
CCCCCGGTGGAGAGTTTACAGTCAGCCCAAGAAACGCTCCTGGAGAGATACTGTGGAGCGCCCCACTCGGCCCCGACCTCAAC
CCCTATCTGTCACATCTCGCTCGCATGTATAACGGCTATGCTGGCGGTTTTGAAGTTCAGGTCATCCTTGCCGGAAACGCCTT
CACCGCTGGGAAGATAATCTTTGCTGCTGTCCCACCCAACTTTCCAACTGAGGGCCTGAGCCCAAGCCAGGTTACAATGTTTC
CACACATGATAGTTGATGTCAGACAGCTGGAGCCAGTCCTTATACCCCTGCCCGATGTCCGAAACAACTTCTACCACTATAAT
CAGAGCAACGACAGCACAATCAAGCTCATCGCTATGCTCTACACACCACTGAGAGCCAACAACGCAGGAGATGACGTGTTTAC
AGTGTCATGTAGAGTCCTCACAAGACCAAGCCCTGATTTTGATTTCATCTTCCTCGTGCCGCCAACTGTTGAGAGCAGAACTA
AGCCCTTTTCTGTTCCCGTGCTGACAGTTGAGGAAATGACAAATTCTAGATTTCCAATCCCCCTTGAAAAGCTGTTTACGGGA
CCAAGCTCTGCCTTCGTGGTGCAGCCACAGAATGGTCGATGTACAACAGACGGCGTCCTGCTCGGTACAACACAGCTCAGCCC
TGTTAACATATGCACTTTTAGGGGCGATGTTACACATATCACTGGTTCTCACAACTATACTATGAACCTGGCCAGCCAGAACT
GGAACAACTACGACCCAACAGAGGAGATCCCTGCTCCACTTGGGACACCCGACTTTGTTGGAAAGATCCAGGGCATGCTGACA
CAGACGACAAAGACCAGATGGTTCAACAAGAGGTCACAAAGCTACTGTTTACACCGGCTCTGCCGATTTCGCACCAAAACTCGG
TAGAGTGCAGTTTCAGACAGATACAGATCACGACTTTGAAGCCAACCAGAACACTAAGTTTACACCAGTCGGAGTTATCCAGG
ACGGCAACACAACACACAGAAACGAGCCACAGCAATGGGTCCTTCCAAGCTATAGCGGCCGGAACACACACAACGTTCACCTT
GCTCCCGCCGTTGCTCCAACATTTCCCGGGGAGCAGCTTCTTTTCTTCCGCTCTACAATGCCCGGGTGCTCTGGATACCCAAA
TATGGATCTGGACTGCCTCCTGCCGCAAGAATGGGTGCAGTATTTTTACCAAGAGGCAGCTCCAGCTCAGTCTGATGTTGCCC
TGCTCCGGTTTGTGAACCCCGATACTGGCCGGGTCCTTTTTGAGTGCAAGCTCCATAAGAGCGGATATGTGACAGTCGCTCAT
ACTGGCCAGCACGACCTCGTTATCCCTCCTAACGGTTACTTCCGATTTGATAGCTGGGTTAACCAGTTTTACACACTTGCCCC
TATGGGCAACGGTACAGGCCGCAGGAGAGCCGTGTAGAGGCCTATTTTCTTTAGTTTGAATTTACTGTTATTCGGTGTGCATT
TCTATGTTTGGTGAGCGGTTTTCTGTGCTCAGAGTGTGTTTATTTTATGTAATTTAATTTCTTTGTGAGCTCCTGTTTAGCAG
GTCGTCCCTTCAGCAAGGACACAAAAAGATTTTAATTTTATTATCGTTCAAACATTTGGCAATAAAGTTTCTTAAGATTGAAT
CCTGTTGCCGGTCTTGCGATGATTATCATATAATTTCTGTTGAATTACGTTAAGCATGTAATAATTAACATGTAATGCATGAC
GTTATTTATGAGATGGGTTTTTATGATTAGAGTCCCGCAATTATACATTTAATACGCGATAGAAAACAAAATATAGCGCGCAA
ACTAGGATAAATTATCGCGCGCGGTGTCATCTATGTTACTAGAT
```

FIGURE 16D

Nucleic acid sequence of construct 4154 from 2X35S promoter to NOS terminator (SEQ ID NO:72)

```
GTCAACATGGTGGAGCACGACACACTTGTCTACTCCAAAAATATCAAAGATACAGTCTCAGAAGACCAAAGGGCAATTGAGAC
TTTTCAACAAAGGGTAATATCCGGAAACCTCCTCGGATTCCATTGCCCAGCTATCTGTCACTTTATTGTGAAGATAGTGGAAA
AGGAAGGTGGCTCCTACAAATGCCATCATTGCGATAAAGGAAAGGCCATCGTTGAAGATGCCTCTGCCGACAGTGGTCCCAAA
GATGGACCCCACCCACGAGGAGCATCGTGGAAAAGAAGACGTTCCAACCACGTCTTCAAAGCAAGTGGATTGATGTGATAA
CATGGTGGAGCACGACACACTTGTCTACTCCAAAAATATCAAAGATACAGTCTCAGAAGACCAAAGGGCAATTGAGACTTTTC
AACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGG
ACCCCACCCACGAGGAGCATCGTGGAAAAGAAGACGTTCCAACCACGTCTTCAAAGCAAGTGGATTGATGTGATATCTCCA
CTGACGTAAGGGATGACGCACAATCCCACTATCCTTCGCAAGACCCTTCCTCTATATAAGGAAGTTCATTTCATTTGGAGAGG
ATAACAATTTAAACAAACAAAATCAACAAATATAGAAAATAACGCATTTCCAATTCTTTGAAATTTCTGCAACAATGAAGATG
GCTAGCTCAGACGCCAATCCAAGCGACGGTAGCGCTGCCAACCTCGTGCCCGAGGTCAACAACGAAGTTATGGCCCTTGAGCC
CGTGGTTGGAGCTGCTATAGCTGCTCCTGTTGCTGGGCAGCAGAACGTGATAGACCCATGGATACGTAACAACTTTGTTCAGG
CCCCCGGTGGAGAGTTTACAGTCAGCCCAAGAAACGCTCCTGGAGAGATACTGTGGAGCGCCTCCCTCGGCCCCGACCTCAAC
CCCTATCTGTCACATCTCGCTCGCATGTATAACGGCTATGCTGGCGGTTTTGAAGTTCAGGTCATCCTTGCCGGAAACGCCTT
```

Figure 16D (continued)

```
CACCGCTGGGAAGATAATCTTTGCTGCTGTCCCACCCAACTTTCCAACTGAGGGCCTGAGCCCAAGCCAGGTTACAATGTTTC
CACACATGATAGTTGATGTCAGACAGCTGGAGCCAGTCCTTATACCCCTGCCCGATGTCCGAAACAACTTCTACCACTATAAT
CAGAGCAACGACAGCACAATCAAGCTCATCGCTATGCTCTACACACCACTGAGAGCCAACAACGCAGGAGATGACGTGTTTAC
AGTGTCATGTAGAGTCCTCACAAGACCAAGCCCTGATTTTGATTTCATCTTCCTCGTGCCGCCAACTGTTGAGAGCAGAACTA
AGCCCTTTTCTGTTCCCGTGCTGACAGTTGAGGAAATGACAAATTCTAGATTTCCAATCCCCCTTGAAAAGCTGTTTACGGGA
CCAAGCTCTGCCTTCGTGGTGCAGCCACAGAATGGTCGATGTACAACAGACGGCGTCCTGCTCGGTACAACACAGCTCAGCCC
TGTTAACATATGCACTTTTAGGGGCGATGTTACACATATCACTGGTTCTCACAACTATACTATGAACCTGGCCAGCCAGAACT
GGAACAACTACGACCCAACAGAGGAGATCCCTGCTCCACTTGGGACACCCGACTTTGTTGGAAAGATCCAGGGCATGCTGACA
CAGACGACAAAGACAGATGGTTCAACAAGAGGTCACAAAGCTACTGTTTACACCGGCTCTGCCGATTTCGCACCAAAACTCGG
TAGAGTGCAGTTTCAGACAGATACAGATCACGACTTTGAAGCCAACCAGAACACTAAGTTTACACCAGTCGGAGTTATCCAGG
ACGGCAACACAACACACAGAAACGAGCCACAGCAATGGGTCCTTCCAAGCTATAGCGGCCGGAACACACACAACGTTCACCTT
GCTCCCGCCGTTGCTCCAACATTTCCCGGGGAGCAGCTTCTTTTCTTCCGCTCTACAATGCCCGGGTGCTCTGGATACCCAAA
TATGGATCTGGACTGCCTCCTGCCGCAAGAATGGGTGCAGTATTTTTACCAAGAGGCAGCTCCAGCTCAGTCTGATGTTGCCC
TGCTCCGGTTTGTGAACCCCGATACTGGCCGGGTCCTTTTTGAGTGCAAGCTCCATAAGAGCGGATATGTGACAGTCGCTCAT
ACTGGCCAGCACGACCTCGTTATCCCTCCTAACGGTTACTTCCGATTTGATAGCTGGGTTAACCAGTTTTACACACTTGCCCC
TATGGGCAACGGTACAGGCCGCAGGAGAGCCGTGTAGAGGCCTATTTTCTTTAGTTTGAATTTACTGTTATTCGGTGTGCATT
TCTATGTTTGGTGAGCGGTTTTCTGTGCTCAGAGTGTGTTTATTTTATGTAATTTAATTTCTTTGTGAGCTCCTGTTTAGCAG
GTCGTCCCTTCAGCAAGGACACAAAAAGATTTTAATTTTATTATCGTTCAAACATTTGGCAATAAAGTTTCTTAAGATTGAAT
CCTGTTGCCGGTCTTGCGATGATTATCATATAATTTCTGTTGAATTACGTTAAGCATGTAATAATTAACATGTAATGCATGAC
GTTATTTATGAGATGGGTTTTTATGATTAGAGTCCCGCAATTATACATTTAATACGCGATAGAAAACAAAATATAGCGCGCAA
ACTAGGATAAATTATCGCGCGCGGTGTCATCTATGTTACTAGAT
```

MODIFIED NOROVIRUS VP1 PROTEINS AND VLPS COMPRISING MODIFIED NOROVIRUS VP1 PROTEINS

CROSS REFERENCE TO RELATED APPLICATIONS

This application is a National Stage of International Application No. PCT/CA2018/051529 filed Nov. 30, 2018, claiming priority based on U.S. Application No. 62/697,770 filed Jul. 13, 2018.

FIELD OF INVENTION

The present invention relates to modified norovirus VP1 proteins, VLPs comprising modified norovirus VP1 proteins, and methods of producing the same.

BACKGROUND OF THE INVENTION

The global disease burden attributed to norovirus infection is high, being associated with an estimated 20% of all worldwide diarrheal cases and causing over 200,000 deaths annually. Noroviruses are the primary cause of foodborne disease outbreaks in North America and are the causative agent for the majority of healthcare-associated outbreaks amongst the elderly. Norovirus strains are also recognized as being the leading cause of pediatric gastrointestinal illness worldwide.

Noroviruses comprise one of a number of genera of the family Caliciviridae. The human norovirus genome is a single-stranded, positive-sense RNA molecule encoding three open reading frames (ORFs) and capped on its 5' end by a VPg protein. ORF1 encodes six non-structural viral proteins, including VPg, an RNA-dependent RNA polymerase, and a viral protease. ORF2 encodes the major structural capsid protein (VP1). ORF3 encodes a minor capsid protein (VP2).

VP1 is comprised of 2 domains: a shell (S) domain, and a protruding (P) domain. The S domain, located at the N-terminal end of the protein, contains structural elements necessary for capsid assembly and the formation of the viral icosahedron. The P domain comprises the remainder of the VP1 protein and is further comprised of a P1 sub-domain and a P2 sub-domain. The P2 sub-domain is referred to as the hypervariable domain and is thought to play an important role in receptor binding and immune reactivity.

VP1 proteins form dimers via P domain-mediated protein interactions. Dimerization increases the stability of the virion capsid and results in formation of the protrusions extending from the base core of the norovirus particle formed by S domains. When expressed, norovirus VP1 proteins can automatically assemble to form 2 virion structures: a 180-mer capsid structure with T=3 icosahedral symmetry having a 38-40 nm diameter; and a 60-mer capsid structure with T=1 icosahedral symmetry having a 23 nm diameter.

VP2, the minor structural protein, has a molecular weight (MW) of approximately 21-24 kDa. Studies suggest that VP2 is highly basic and located inside the capsid. The function of VP2 is not yet fully understood but it is generally believed to play a role in capsid stability by protecting the virions from disassembly and degradation (Bertolotti-Ciarlet A., Crawford S. E., Hutson A. M., Estes M. K. 2003, J. Virol. 77:11603-11615). VP2 may also have a function during RNA genome packaging. The amount of VP2 minor structural protein in virions is relatively low with 1.5 to 8 copies incorporated into the mature virion. Bertolotti-Ciarlet et. al. (2003) report that in insect and mammalian cells, VLPs composed of VP1/VP2 are more resistant to protease cleavage than those with only VP1, and that expression of VP2 in cis, results in an increase in VP1 protein production. In addition, the presence of the 3'UTR downstream of the ORF2 gene increases the steady-state levels of NV ORF2 mRNA. The greatest increase in VP1 expression was observed when ORF2+ORF3+3'UTR, residing on the same construct and under regulation of one promoter, was expressed. Expression of VP2 in trans did not result in any increase in VP1 expression, indicating that the subgenomic organization of ORF2-ORF2-3'UTR was required for the observed increase in VP1 production.

Noroviruses are classified according to their phylogenetic clustering of the VP1 amino acid sequence. Seven genogroups have been classified to date (G1 through GVII) with only genogroups GI, GII, and GIV known to infect humans. Of the 32 specific genotypes currently associated with human infections, GII.4 noroviruses have been responsible for the majority of recent norovirus outbreaks. New strains of GII.4 emerge every two to three years, evolving by a process driven by mutations in epitope determining regions of the hypervariable P2 domain of VP1. This process allows the norovirus to escape humoral immune responses acquired by previous exposure to earlier strains.

While faced with the difficulty of rapidly evolving and genetically diverse norovirus strains, the development of effective norovirus vaccines has been exacerbated by additional challenges. For instance, until recently, human norovirus could not be grown in cell culture and even now, robust cell culture systems for both VLPs and live attenuated noroviruses are lacking.

An additional challenge in vaccine development is that immunity to norovirus infection is strain and genotype specific with minimal cross-immunity conferred against other genogroups. Furthermore, immunity to a norovirus strain is not life-long and is estimated to persist from anywhere between six months and nine years.

Globally, Norovirus GII strains are dominant, and GII.4 has been the predominant Norovirus genotype. Genetically distinct novel GII.4 variants have emerged every two to three years and spread rapidly around the world. GII.4 variants US95/96, Farmington Hills 2002, Hunter 2004, Den Haag 2006b (2006b), New Orleans 2009, and Sydney 2012 are recognized as pandemic variants, while some variants, such as Asia 2003 and Yerseke 2006a, have been reported only in limited regional epidemics. Moreover, it has been reported that GII.4 causes a more severe gastroenteritis than other genotypes Various approaches have been undertaken to develop a suitable vaccine against norovirus infection including the production of recombinant norovirus proteins in insect and plant expression systems.

Huo et al. (*Virus Research*, 2015, 204:1-5) demonstrated that an M27G mutant capsid protein, of norovirus VP1 VLPs produced in insect SF9 cells, resulted in the production of 38 nm and 21 nm VLPs, comprising proteins of 58 kDa and 55 kDa. The 55 kDa protein was a result of degradation or cleavage of the full-length P1 capsid protein as opposed to the translated product of an internal start codon. N-terminal deletion mutants comprising 26 or 38 deleted amino acid residues of the VP1 protein, resulted in the production of 21 nm VLPs. The 26 amino acid deletion mutants produced low numbers of 38 nm VLPs whereas 38 amino acid deletion mutants did not result in formation of 38 nm VLPs.

US 2013/0273105 teaches the production of norovirus formulations comprising antigenic peptides, proteins or VLPs derived from genogroup I (G1), genogroup II (GII), or consensus viral sequences. The norovirus antigens may include variants of the capsid proteins expressed in the VLPs.

US 2015/0023995 provides a vaccine formulation comprising VLPs produced in insect Sf9 cells, the VLPs comprising a composite amino acid sequence derived from at least two viral protein sequences. For Example, a composite GII.4 VP1 VLP, comprising a VP1 sequence from GII.4 Minerva 2006-a, and GII.4 Laurens 2006-b and GII.4 Houston 2002 norovirus strains, is described. Composite sequences derived from GII.1, GII.2 Snow Mountain and GII.3, as well as GI composite sequences derived from Norwalk GI.1, Southampton GI.1, and Chiba GI.1 are also described.

Mason et al. (*Proc Natl Acad Sci USA.*, 1996, 93(11): 5335-40) teach the use of genetically engineered tobacco plants and potato tubers to express GI.1 norovirus VLPs from native VP1 protein. The plant produced norovirus VLPs are morphologically and physically similar to the 38 nm Norwalk VLPs produced in insect cells. Oral administration of purified tobacco-produced Norwalk VLPs from native capsid protein, or potato tubers expressing GI.1 capsid protein induced a humoral immune response in mice and humans (Tacket et al., *J. Infect. Dis.*, 2000, 182(1):302-5).

Huang et al. (*Biotechnol. Bioeng.*, 2009, 103(4):706-14) describe a geminivirus-derived DNA replicon vector for production of GI.1 norovirus VLP in plants. Co-delivery of bean yellow dwarf virus-derived vector and Rep/RepA-supplying vector in *Nicotiana benthamiana* resulted in rapid and robust protein production.

SUMMARY OF THE INVENTION

The present invention relates to modified norovirus proteins, virus like particles (VLPs) comprising modified norovirus proteins, and methods of producing norovirus proteins, and virus like particles (VLPs) comprising modified norovirus proteins.

It is an object of the invention to produce modified norovirus proteins, VLPs comprising modified norovirus proteins, and to produce VLPs comprising modified norovirus proteins in plants.

As described herein, there is provided a nucleic acid comprising a nucleotide sequence encoding a modified norovirus VP1, the modified norovirus VP1 comprising, an S domain and a P domain, the S domain comprising a substitution at one or more than one amino acid corresponding to amino acids 39, 53 or 80 of norovirus VP1 GII.4/2012 (SEQ ID NO:1);
the P domain comprising a substitution at one or more than one amino acids corresponding to amino acids 333 or 368 of norovirus VP1 GII.4/2012 (SEQ ID NO:1), or a combination thereof.

Also provided is the nucleic acid as described above, wherein the nucleotide sequence encoding the modified norovirus VP1 protein may be derived from any norovirus GII.4 strain. For example, which is not to be considered limiting, the norovirus GII.4 strain may be selected from the group of GII.4/Sydney/NSW0514/2012/AU (SEQ ID NO:1), Hu/GII.4/Sydney/2015 (SEQ ID NO:3), US96/GII.4/Dresden174/1997/DE_AY741811 (SEQ ID NO:5), FH02/GII.4/FarmingtonHills/2002/US_AY502023 (SEQ ID NO:6), Hnt04:GII.4/Hunter-NSW504D/2004/AU_DQ07-8814 (SEQ ID NO:7), 2006b: GII.4/Shellharbour-NSW69-6T/2006/AU_EF684915 (SEQ ID NO:8), and NO09: G11.4/Orange-NSW001P/2008/AU_GQ845367 (SEQ ID NO:9).

Furthermore, the S domain may be derived from norovirus genotype Hu/GII.4/Sydney/NSW0514/2012/AU or Hu/GII.4/Sydney/2015, and the P domain may be derived from norovirus genotype Hu/GII.4/Sydney/2015.

The recombinant nucleic acid described above may encode a modified VP1 protein comprising one or more than one amino acid substitutions, independently selected from the following:

1) an S domain derived from norovirus strain Hu/GII.4/Sydney/NSW0514/2012/AU or Hu/GII.4/Sydney/2015 that comprises an amino acid substitution at a position in sequence alignment, or corresponding, with amino acid 80 of norovirus VP1 genotype GII.4/2012 (SEQ ID NO:1). The modified VP1 protein as just described may also comprise a P domain that comprises an amino acid substitution at a position in sequence alignment, or corresponding, with amino acid 333, 368, or amino acids 333 and 368 of norovirus VP1 genotype GII.4/2012 (SEQ ID NO:1).

2) an S domain derived from norovirus strain Hu/GII.4/Sydney/NSW0514/2012/AU, or Hu/GII.4/Sydney/2015 that comprises two amino acid substitutions at positions in sequence alignment, or corresponding, with amino acids 39 and 80 of norovirus VP1 genotype GII.4/2012 (SEQ ID NO:1). The modified VP1 protein as just described may also comprise a P domain that comprises an amino acid substitution at a position in sequence alignment, or corresponding, with amino acids 333, 368, or amino acids 333 and 368 of norovirus VP1 genotype GII.4/2012 (SEQ ID NO:1).

3) an S domain derived from norovirus strain Hu/GII.4/Sydney/NSW0514/2012/AU, or Hu/GII.4/Sydney/2015 that comprises two amino acid substitutions at positions in sequence alignment, or corresponding, with amino acid 53 and 80 of norovirus VP1 genotype GII.4/2012 (SEQ ID NO:1). The modified VP1 protein as just described may also comprise a P domain that comprises an amino acid substitution at a position in sequence alignment, or corresponding, with amino acid 333, 368, or amino acids 333 and 368 of norovirus VP1 genotype GII.4/2012 (SEQ ID NO:1).

4) an S domain derived from norovirus strain Hu/GII.4/Sydney/NSW0514/2012/AU, or Hu/GII.4/Sydney/2015 that comprises three amino acid substitutions at positions in sequence alignment, or corresponding, with amino acid 39, 53 and 80 of norovirus VP1 genotype GII.4. The modified VP1 protein as just described may also comprise a P domain that comprises an amino acid substitution at a position in sequence alignment, or corresponding, with amino acid 333, 368, or amino acids 333 and 368 of norovirus VP1 genotype GII.4/2012 (SEQ ID NO:1).

The nucleic acid described above may further encode a modified norovirus GII.4 VP1 protein comprising one or more than one substitution at the amino acid residue corresponding to:

amino acid 39, wherein the amino acid is substituted to valine, isoleucine, leucine or methionine;
amino acid 80, wherein the amino acid is substituted to serine, asparagine, cysteine or threonine;
amino acid 53, wherein the amino acid is substituted to isoleucine, leucine, valine, alanine or methionine;
amino acid 333, wherein the amino acid is substituted to valine, isoleucine or leucine;
amino acid 368, wherein the amino acid is substituted to glutamate, asparagine or aspartate.

Any of the nucleic acids described above may also be optimized for human codon usage, increased GC content, or a combination thereof.

A vector comprising the any one of the nucleic acid as described above is also provided herein.

A modified norovirus VP1 protein encoded by any one of the nucleic acid described above is also described herein. The modified VP1 protein may comprise from about 80 to about 100% amino acid sequence similarity with Hu/GII.4/Sydney/2015 (SEQ ID NO:3), or GII.4/Sydney/NSW0514/2012/AU (SEQ ID NO:1), provided that the modified norovirus VP1 protein comprises one or more substitutions at amino acid position 39, 53, 80, 333 and 368. Furthermore, a VLP comprising the modified norovirus VP1 protein encoded by any one of the recombinant nucleic acid described above, is also disclosed. The VLP comprising the modified norovirus VP1 protein encoded by any one of the nucleic acid described above, may further comprise a norovirus VP2 protein.

A method for producing a modified norovirus VP1 in a plant, portion of a plant or plant cell is also provided herein. The modified norovirus VP1 may be encoded by any one of the nucleic acid described above. The method comprises introducing one or more than one of the nucleic acid described above into the plant, the portion of the plant or the plant cell, and incubating the plant, the portion of the plant or the plant cell under conditions that permit expression of the one or more than one modified norovirus VP1 protein. The method provided herein may further comprise a step of harvesting the plant, portion of the plant, or the plant cell. Additionally, the method may comprise a step of extracting, purifying, or both extracting and purifying the one or more than one modified norovirus VP1 protein from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the one or more than one modified norovirus VP1 protein and the norovirus VP2 protein in the plant, portion of the plant or the plant cell.

Also described is a method for producing a norovirus virus like particle (VLP) in a plant, portion of a plant or plant cell, wherein the VLP comprises one or more than one of the modified norovirus VP1 proteins encoded by one or more of the nucleic acid described above. The method comprises introducing one or more than one of the nucleic acid described above into the plant, the portion of the plant or the plant cell, and incubating the plant, the portion of the plant or the plant cell under conditions that permit expression of the one or more than one modified norovirus VP1 protein, thereby producing the norovirus VLP. The method provided herein may further comprise a step of harvesting the plant, portion of the plant, or the plant cell. Additionally, the method may comprise a step of extracting, purifying, or both extracting and purifying the norovirus VLP from the plant, the portion of the plant or the plant cell. Furthermore, in the step of introducing, the method may further comprise introducing a second nucleic acid sequence encoding a norovirus VP2 protein into the plant, the portion of the plant, or the plant cell, and in the step of incubating, the conditions permit co-expression and co-production of both the modified norovirus VP1 protein and the norovirus VP2 protein in the plant, portion of the plant or the plant cell thereby producing the norovirus VLP. The norovirus VLP produced by the method described herein may have a diameter of about 15 nm to 50 nm. Alternatively, the VLP may have a diameter of about 23 nm (for T=1 icosahedral symmetry) or about 38 nm (for T=3 icosahedral symmetry).

A method of producing an antibody or antibody fragment is provided herein, wherein the method comprises administering one or more than one of the modified norovirus VP1 proteins encoded by one or more than one of the nucleic acid described above, or the norovirus VLP comprising one or more than one of the modified norovirus VP1 protein, to a subject or a host animal, thereby producing the antibody or the antibody fragment.

Also provided herein is a plant, portion of the plant, or plant cell comprising the nucleic acid described above, the modified norovirus VP1 encoded by one or more than one of the recombinant nucleic acid, or the norovirus VLP comprising one or more than one the modified norovirus VP1 protein.

A composition for inducing an immune response is also described herein. The composition comprises, an effective dose of one or more than one of the modified norovirus VP1 protein encoded by one or more than one of the nucleic acid described above, or the norovirus VLP comprising one or more than one of the modified norovirus VP1 protein, and a pharmaceutically acceptable carrier, adjuvant, vehicle or excipient.

The present disclosure also provides a vaccine for inducing an immune response, wherein the vaccine comprises an effective dose of one or more than one of the modified norovirus VP1 proteins encoded by one or more than one of the nucleic acid described above, or the VLP comprising one or more than one of the modified norovirus VP1 protein.

An antibody or antibody fragment is provided herein, wherein the antibody or antibody fragment is prepared by administering one or more than one of the modified norovirus VP1 encoded by one or more than one of the nucleic acid described above, or the norovirus VLP comprising one or more than one of the modified norovirus VP1, to a subject or host animal.

Also described herein is a method of inducing immunity to a norovirus infection in a subject, wherein the method comprises administering one or more than one of the modified norovirus VP1 protein encoded by one or more than one of the nucleic acid described above, or the norovirus VLP comprising one or more than one of the modified norovirus VP1 protein. The one or more than one of the modified norovirus VP1 protein, or the norovirus VLP may be administered to the subject orally, intranasally, intramuscularly, intraperitoneally, intravenously subcutaneously, rectally, or intravaginally.

A method of increasing the yield of a norovirus virus like particle (VLP) in a plant, portion of a plant or a plant cell, is provided. The method comprises, introducing the nucleic acid as described above in a plant, portion of the plant, or a plant cell, and incubating the plant, portion of the plant or the plant cell under conditions that permit expression of the modified norovirus VP1 protein thereby producing the norovirus VLP, wherein the yield of the norovirus VLP comprising the modified norovirus VP1 protein is greater than the yield of a norovirus VLP comprising wild type norovirus VP1 protein produced in the plant, portion of the plant or the plant cell, under the same conditions.

This summary of the invention does not necessarily describe all features of the invention.

BRIEF DESCRIPTION OF THE DRAWINGS

These and other features of the invention will become more apparent from the following description in which reference is made to the appended drawings wherein.

2015_A39V+R53I+P80S+Q368E VP1 (Construct #: 4254), mut GII.4/2015_A39V+R53I+P80S+M333V Q368E VP1 (Construct #: 4255).

"GII.4/2015" refers to norovirus strain GII.4/Sydney/2015 (SEQ ID NO:3). Amino acids substitutions in the VP1 are indicated by wild type amino acid residue followed by the residue number and the substituted amino acid residue. FIG. 4B shows a series of transmission electron micrographs (TEM; 15,000× magnification; scale bar=500 nm) of virus like particles (VLPs) purified from iodixanol density gradient fractions of crude protein extracts prepared from *N. benthamiana* leaves expressing, upper panel from left to right: mut GII.4/2015_P80S+M333V VP1 (Construct #: 4241), mut GII.4/2015_P80S+Q368E VP1 (Construct #: 4242), mut GII.4/2015_P80S+M333V+Q368E VP1 (Construct #: 4243); upper middle panel: mut GII.4/2015_A39V+P80S VP1 (Construct #: 4244); mut GII.4/2015_A39V+P80S+M333V VP1 (Construct #: 4245), mut GII.4/2015_A39V+P80S+Q368E VP1 (Construct #: 4246), mut GII.4/2015_A39V+P80S+M333V+Q368E VP1 (Construct #: 4247); lower middle panel: mut GII.4/2015_R53I+P80S VP1 (Construct #: 4248), mut GII.4/2015_R53I+P80S+M333V VP1 (Construct #: 4249, mut GII.4/2015_R53I+P80S+Q368E VP1 (Construct #: 4250), mut GII.4/2015_R53I+P80S+M333V+Q368E VP1 (Construct #: 4251); lower panel: mut GII.4/2015_A39V+R53I+P80S VP1 (Construct #: 4252), mut GII.4/2015_A39V+R53I+P80S+M333V VP1 (Construct #: 4253), mut GII.4/2015_A39V+R53I+P80S+Q368E VP1 (Construct #: 4254), mut GII.4/2015_A39V+R53I+P80S+M333V Q368E VP1 (Construct #: 4255).

"GII.4/2015" refers to norovirus strain GII.4/Sydney/2015 (SEQ ID NO:3). Amino acids substitutions in the VP1 are indicated by wild type amino acid residue followed by the residue number and the substituted amino acid residue.

FIG. 5A shows the amino acid sequence of VP1 Hu/GII.4_Sydney_2012_K4LM89 (also termed GII.4/Sydney/NSW0514/2012/AU, or GII.4/2012; SEQ ID NO: 1); FIG. 5B shows the nucleic acid sequence human codon-optimized VP1 Hu/GII.4_Sydney_2012_K4LM89 (SEQ ID NO:2). FIG. 5C shows the amino acid sequence of VP1 GII.4/Sydney/2015 (GII.4/2015; SEQ ID NO: 3); FIG. 5D shows the nucleic acid sequence of human codon-optimized (Hu cod) VP1 GII.4/Sydney/2015 (GII.4/2015; SEQ ID NO:4; sequence kindly provided by Miranda de Graaf, Erasmus University Medical Center, Rotterdam) (SEQ ID NO:4).

FIG. 6A shows the amino acid sequence of VP1 US96: GII.4/Dresden174/1997/DE_AY741811 (SEQ ID NO: 5); FIG. 6B shows the amino acid sequence of VP1 of VP1 FH02: GII.4/FarmingtonHills/2002/US_AY502023 (SEQ ID NO: 6); FIG. 6C shows the amino acid sequence of VP1 Hnt04:GII.4/Hunter-NSW504D/2004/AU_DQ078814 (SEQ ID NO: 7); FIG. 6D shows the amino acid sequence of VP1 2006b: GII.4/Shellharbour-NSW696T/2006/AU_EF684915 (SEQ ID NO: 8); FIG. 6E shows the amino acid sequence of VP1 NO09: GII.4/Orange-NSW001P/2008/AU_GQ845367 (SEQ ID NO: 9).

FIG. 7A shows the nucleic acid sequence of human codon optimized (Hu cod) VP1 GII.4/2012_P80S (SEQ ID NO:10). FIG. 7B shows the amino acid sequence of VP1 GII.4/2012_P80S (SEQ ID NO:11). FIG. 7C shows a schematic representation of construct 4152 (VP1 GII.4/2012_P80S). FIG. 7D shows the nucleic acid sequence of human codon optimized (Hu cod) VP1 GII.4/2015_P80S (SEQ ID NO:12). FIG. 7E shows the amino acid sequence of VP1 GII.4/2015_P80S (SEQ ID NO:13). FIG. 7F shows a schematic representation of construct 4154 (VP1 GII.4/2015_P80S). FIG. 7G shows the nucleic acid sequence of human codon optimized (Hu cod) VP1 S(GII.4/2012_P80S)+P(GII.4/2015; SEQ ID NO:14). FIG. 7H shows the amino acid sequence of VP1 S(GII.4/2012_P80S)+P(GII.4/2015) (SEQ ID NO:15).

FIG. 7I shows a schematic representation of construct 4171 (VP1 S(GII.4/2012_P80S)+P(GII.4/2015)).

FIG. 8A shows the nucleic acid sequence of human codon optimized (Hu cod) VP1 S(GII.4/2012_P80S)+P(GII.4/2015_M333V) (SEQ ID NO:16). FIG. 8B shows the amino acid sequence of VP1 S(GII.4/2012_P80S)+P(GII.4/2015_M333V) (SEQ ID NO:17). FIG. 8C shows the schematic representation of construct 4174 (VP1 S(GII.4/2012_P80S)+P(GII.4/2015_M333V)). FIG. 8D shows the nucleic acid sequence of human codon optimized (Hu cod) VP1 S(GII.4/2012_P80S)+P(GII.4/2015_Q368E); SEQ ID NO:18). FIG. 8E shows the amino acid sequence of VP1 S(GII.4/2012_P80S)+P(GII.4/2015_Q368E) (SEQ ID NO:19). FIG. 8F shows a schematic representation of construct 4176 (VP1 S(GII.4/2012_P80S)+P(GII.4/2015_Q368E)). FIG. 8G shows the nucleic acid sequence of human codon optimized (Hu cod) VP1 S(GII.4/2012_P80S)+P(GII.4/2015 M333V+Q368E); SEQ ID NO: 20). FIG. 8H shows the amino acid sequence of VP1 S(GII.4/2012_P80S)+P(GII.4/2015_M333V+Q368E) (SEQ ID NO:21). FIG. 8I shows a schematic representation of construct 4187 (VP1 S(GII.4/2012_P80S)+P(GII.4/2015_M333V+Q368E)).

FIG. 9A shows the nucleic acid sequence of human codon optimized (Hu cod) VP1 S(GII.4/2012_A39V+P80S)+P(GII.4/2015_M333V); SEQ ID NO:22). FIG. 9B shows the amino acid sequence of VP1 S(GII.4/2012_A39V+P80S)+P(GII.4/2015_M333V) (SEQ ID NO:23). FIG. 9C shows a schematic representation of construct 4188 (VP1 S(GII.4/2012_A39V+P80S)+P(GII.4/2015_M333V)). FIG. 9D shows the nucleic acid sequence of human codon optimized (Hu cod) VP1 S(GII.4/2012_A39V+P80S)+P(GII.4/2015_Q368E); SEQ ID NO:24). FIG. 9E shows the amino acid sequence of VP1 S(GII.4/2012_A39V+P80S)+P(GII.4/2015_Q368E) (SEQ ID NO:25). FIG. 9F shows a schematic representation of construct 4194 (VP1 S(GII.4/2012_A39V+P80S)+P(GII.4/2015_Q368E)). FIG. 9G shows the nucleic acid sequence of human codon optimized (Hu cod) VP1 S(GII.4/2012_A39V+P80S)+P(GII.4/2015_M333V+Q368E; SEQ ID NO:26). FIG. 9H shows the amino acid sequence of VP1 S(GII.4/2012_A39V+P80S)+P(GII.4/2015_M333V+Q368E (SEQ ID NO:27). FIG. 9I shows a schematic representation of construct 4191 (VP1 S(GII.4/2012_A39V+P80S)+P(GII.4/2015_M333V+Q368E).

FIG. 10A shows the nucleic acid sequence of human codon optimized (Hu cod) VP1 S(GII.4/2012_R53I+P80S)+P(GII.4/2015_M333V); SEQ ID NO:28). FIG. 10B shows the amino acid sequence of VP1 S(GII.4/2012_R53I+P80S)+P(GII.4/2015_M333V) (SEQ ID NO:29). FIG. 10C shows a schematic representation of construct 4189 (VP1 S(GII.4/2012_R53I+P80S)+P(GII.4/2015_M333V)). FIG. 10D shows the nucleic acid sequence of human codon optimized (Hu cod) VP1 S(GII.4/2012_R53I+P80S)+P(GII.4/2015_Q368E); SEQ ID NO:30).

FIG. 10E shows the amino acid sequence of VP1 S(GII.4/2012_R53I+P80S)+P(GII.4/2015_Q368E) (SEQ ID NO:31). FIG. 10F shows a schematic representation of construct 4195 (VP1 S(GII.4/2012_R53I+P80S)+P(GII.4/2015_Q368E)). FIG. 10G shows the nucleic acid sequence of human codon optimized (Hu cod) VP1 S(GII.4/

2012_R53I+P80S)+P(GII.4/2015_M333V+Q368E); SEQ ID NO:32). FIG. 10H shows the amino acid sequence of VP1 S(GII.4/2012_R53I+P80S)+P(GII.4/2015_M333V+Q368E) (SEQ ID NO:33). FIG. 10I shows a schematic representation of construct 4192 VP1 S(GII.4/2012_R53I+P80S)+P(GII.4/2015_M333V+Q368E).

Figures 11C, 11D:
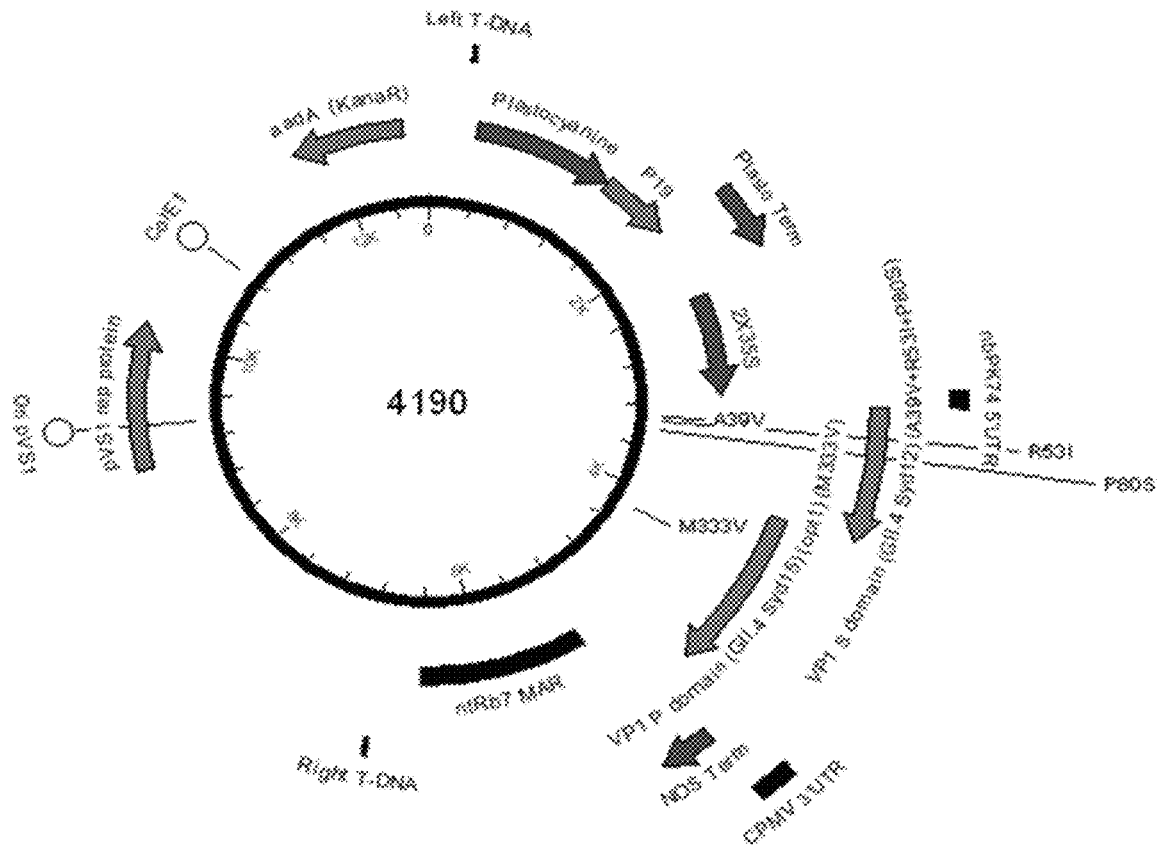

FIG. 11A shows the nucleic acid sequence of human codon optimized (Hu cod) VP1 S(GII.4/2012_A39V+R53I+P80S)+P(GII.4/2015_M333V); SEQ ID NO:34). FIG. 11B shows the amino acid sequence of VP1 S(GII.4/2012_A39V+R53I+P80S)+P(GII.4/2015_M333V) (SEQ ID NO:35). FIG. 11C shows a schematic representation of construct 4190)VP1 S(GII.4/2012_A39V+R53I+P80S)+P(GII.4/2015_M333V)). FIG. 11D shows the nucleic acid sequence of human codon optimized (Hu cod) VP1 S(GII.4/2012_A39V+R53I+P80S)+P(GII.4/2015_Q368E); SEQ ID NO:36). FIG. 11E shows the amino acid sequence of VP1 S(GII.4/2012_A39V+R53I+P80S)+P(GII.4/2015_Q368E) (SEQ ID NO:37). FIG. 11F shows a schematic representation of construct 4196 (VP1 S(GII.4/2012_A39V+R53I+P80S)+P(GII.4/2015_Q368E)). FIG. 11G shows the nucleic acid sequence of human codon optimized (Hu cod) VP1 S(GII.4/2012_A39V+R53I+P80S)+P(GII.4/2015_M333V+Q368E); SEQ ID NO:38). FIG. 11H shows the amino acid sequence of VP1 S(GII.4/2012_A39V+R53I+P80S)+P(GII.4/2015_M333V+Q368E) (SEQ ID NO:39). FIG. 11I shows a schematic representation of construct 4193 (VP1 S(GII.4/2012_A39V+R53I+P80S)+P(GII.4/2015_M333V+Q368E)).

FIG. 12A shows the nucleic acid sequence of human codon optimized (Hu cod) VP1 GII.4/2015_P80S+M333V; SEQ ID NO:40). FIG. 12B shows the amino acid sequence of VP1 GII.4/2015_P80S+M333V (SEQ ID NO:41). FIG. 12C shows a schematic representation of construct 4241 (VP1 GII.4/2015_P80S+M333V). FIG. 12D shows the nucleic acid sequence of human codon optimized (Hu cod) VP1 GII.4/2015_P80S+Q368E; SEQ ID NO:42). FIG. 12E shows the amino acid sequence of VP1 GII.4/2015_P80S+Q368E (SEQ ID NO:43). FIG. 12F shows a schematic representation of construct 4242 (VP1 GII.4/2015_P80S+Q368E). FIG. 12G shows the nucleic acid sequence of human codon optimized (Hu cod) VP1 GII.4/2015_P80S+M333V+Q368E; SEQ ID NO:44). FIG. 12H shows the amino acid sequence of VP1 GII.4/2015_P80S+M333V+Q368E (SEQ ID NO:45). FIG. 12I shows a schematic representation of construct 4243 (VP1 GII.4/2015_P80S+M333V+Q368E).

FIG. 13A shows the nucleic acid sequence of human codon optimized (Hu cod) VP1 GII.4/2015_A39V+P80S; SEQ ID NO:46). FIG. 13B shows the amino acid sequence of VP1 GII.4/2015_A39V+P80S (SEQ ID NO:47). FIG. 13C shows a schematic representation of construct 4244 (VP1 GII.4/2015_A39V+P80S). FIG. 13D shows the nucleic acid sequence of human codon optimized (Hu cod) VP1 GII.4/2015_A39V+P80S+M333V; SEQ ID NO:48). FIG. 13E shows the amino acid sequence of VP1 GII.4/2015_A39V+P80S+M333V (SEQ ID NO:49). FIG. 13F shows a schematic representation of construct 4245 (VP1 GII.4/2015_A39V+P80S+M333V).

FIG. 13G shows the nucleic acid sequence of human codon optimized (Hu cod) VP1 GII.4/2015_A39V+P80S+Q386E; SEQ ID NO:50). FIG. 13H shows the amino acid sequence of VP1 GII.4/2015_A39V+P80S+Q386E (SEQ ID NO:51). FIG. 13I shows a schematic representation of construct 4246 (VP1 GII.4/2015_A39V+P80S+Q386E). FIG. 13J shows the nucleic acid sequence of human codon optimized (Hu cod) VP1 GII.4/2015_A39V+P80S+M333V+Q386E; SEQ ID NO:52). FIG. 13K shows the amino acid sequence of VP1 GII.4/2015_A39V+P80S+M333V+Q386E (SEQ ID NO:53). FIG. 13L shows a schematic representation of construct 4247 (VP1 GII.4/2015_A39V+P80S+M333V+Q386E).

FIG. 14A shows the nucleic acid sequence of human codon optimized (Hu cod) VP1 GII.4/2015_R53I+P80S; SEQ ID NO:54). FIG. 14B shows the amino acid sequence of VP1 GII.4/2015_R53I+P80S (SEQ ID NO:55). FIG. 14C shows a schematic representation of construct 4248 (VP1 GII.4/2015_R53I+P80S). FIG. 14D shows the nucleic acid sequence of human codon optimized (Hu cod) VP1 GII.4/2015_R53I+P80S+M333V; SEQ ID NO:56). FIG. 14E shows the amino acid sequence of VP1 GII.4/2015_R53I+P80S+M333V (SEQ ID NO:57). FIG. 14F shows a schematic representation of construct 4249 (VP1 GII.4/2015_R53I+P80S+M333V). FIG. 14G shows the nucleic acid sequence of human codon optimized (Hu cod) VP1 GII.4/2015_R53I+P80S+Q386E; SEQ ID NO:58). FIG. 14H shows the amino acid sequence of VP1 GII.4/2015_R53I+P80S+Q386E (SEQ ID NO:59).

FIG. 14I shows a schematic representation of construct 4250 (VP1 GII.4/2015_R53I+P80S+Q386E). FIG. 14J shows the nucleic acid sequence of human codon optimized (Hu cod) VP1 GII.4/2015_R53I+P80S+M333V+Q386E; SEQ ID NO:60). FIG. 14K shows the amino acid sequence of VP1 GII.4/2015_R53I+P80S+M333V+Q386E (SEQ ID NO:61). FIG. 14L shows a schematic representation of construct 4251 (VP1 GII.4/2015_R53I+P80S+M333V+Q386E).

FIG. 15A shows the nucleic acid sequence of human codon optimized (Hu cod) VP1 GII.4/2015_A39V+R53I+P80S; SEQ ID NO:62). FIG. 15B shows the amino acid sequence of VP1 GII.4/2015_A39V+R53I+P80S (SEQ ID NO:63). FIG. 15C shows a schematic representation of construct 4252 (VP1 GII.4/2015_A39V+R53I+P80S). FIG. 15D shows the nucleic acid sequence of human codon optimized (Hu cod) VP1 GII.4/2015_A39V+R53I+P80S+M333V; SEQ ID NO:64). FIG. 15E shows the amino acid sequence of VP1 GII.4/2015_A39V+R53I+P80S+M333V (SEQ ID NO:65). FIG. 15F shows a schematic representation of construct 4253 (of VP1 GII.4/2015_A39V+R53I+P80S+M333V). FIG. 15G shows the nucleic acid sequence of human codon optimized (Hu cod) VP1 GII.4/2015_A39V+R53I+P80S+Q386E; SEQ ID NO:66). FIG. 15H shows the amino acid sequence of VP1 GII.4/2015_A39V+R53I+P80S+Q386E (SEQ ID NO:67).

FIG. 15I shows a schematic representation of construct 4254 (VP1 GII.4/2015_A39V+R53I+P80S+Q386E). FIG. 15J shows the nucleic acid sequence of human codon optimized (Hu cod) VP1 GII.4/2015_A39V+R53I+P80S+M333V+Q386E; SEQ ID NO:68). FIG. 15K shows the amino acid sequence of VP1 GII.4/2015_A39V+R53I+P80S+M333V+Q386E (SEQ ID NO:69). FIG. 15L shows a schematic representation of construct 4255 (VP1 GII.4/2015_A39V+R53I+P80S+M333V+Q386E).

FIG. 16A shows the nucleic acid sequence of cloning vector 3674 from left to right T-DNA (SEQ ID NO:70). FIG. 16B shows a schematic of construct 3674. FIG. 16C shows the nucleic acid sequence of construct 4153 from 2×35S promoter to NOS terminator (SEQ ID NO:70). FIG. 16D shows the nucleic acid sequence of Construct 4154 from 2×35S promoter to NOS terminator (SEQ ID NO:70).

DETAILED DESCRIPTION

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion", "plant matter", "plant biomass", "plant material", plant extract", or "plant leaves", as used herein, may comprise an entire plant, tissue (e.g. leaves, stem, root) cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, agricultural crops including for example canola, *Brassica* spp., maize, *Nicotiana* spp., (tobacco) for example, *Nicotiana benthamiana, Nicotiana rustica, Nicotiana, tabacum, Nicotiana alata, Arabidopsis thaliana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The term "plant portion", as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein suprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term "nucleic acid segment" as used herein refers to a sequence of nucleic acids that encodes a protein of interest. In addition to the sequence of nucleic acids, the nucleic acid segment comprise a regulatory region and a terminator that are operatively linked to the sequence of nucleic acids. The regulatory region may for example comprise a promoter, and optionally, an enhancer element operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The term "vector" or "expression vector", as used herein, refers to a recombinant nucleic acid for transferring exogenous nucleic acid sequences into host cells (e.g. plant cells) and directing expression of the exogenous nucleic acid sequences in the host cells. "Expression cassette" refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active in the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1,5-bisphosphate carboxylase gene (ssRUBISCO; U.S. Pat. No. 4,962,028; which is incorporated herein by reference), the terminator used in regulating plastocyanin expression.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004); the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to the amino acid sequence of the wild type protein or domain. Native proteins or domains may be encoded by nucleotide sequences having 100% sequence similarity to the wild type sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

When it is stated that an amino acid, an amino acid sequence, or a protein is "modified" it is meant that the amino acid, amino acid sequence, or protein is altered in some manner when compared to the corresponding native or wild type amino acid, amino acid sequence, or protein from which the modified amino acid, amino acid sequence, or protein is derived. For example, a modified amino acid, amino acid sequence, or protein may include the replacement of one or more amino acids by substitution (i.e. replacement) or mutation. A modified amino sequence or a modified protein may also comprise one or more deleted amino acids, or there may be one or more inserted amino acids. Techniques to carry out such modification are well known to one of skill in the art.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC content (when compared to the wild type nucleotide sequence) exhibits increased expression within a plant, portion of a plant, or a plant cell, when compared to expression of the non-human optimized (or lower GC content) nucleotide sequence.

Norovirus VP1 mutant proteins (also termed modified VP1 protein, modified norovirus VP1 protein, variants of norovirus VP1 protein, GII.4 VP1 mutant protein, modified GII.4 VP1 protein, modified norovirus GII.4 VP1 protein, variants of norovirus GII.4 VP1 protein, and the like) and methods of producing norovirus modified VP1 proteins in plants are described herein. Several of the modified norovirus VP1 proteins comprise specific modifications, for example substitutions or mutations, in the S domain and/or P domain of GII.4 VP1's, and are variants of the norovirus GII.4 genotype VP1 protein. Furthermore, the modified norovirus VP1 protein may be norovirus VP1 fusion protein, wherein the S-domain is derived from a first norovirus genotype variant fused to a P domain, or a portion of the P domain, derived from a second norovirus genotype variant. It has been observed that in norovirus GII.4 genotypes, modifying specific amino acids results in improved VP1 characteristics as compared to the wild type VP1. Examples of improved characteristics of the VP1 include, increased VP1 protein yield when expressed in plant cells as compared to the wild type VP1 of the same genotype that does not comprise the modification or substitution(s); increased density of VLPs comprised of the modified VP1 proteins (for example as determined using density gradient separation, and optionally SDS-PAGE and/or Western analysis) as compared to the wild type VP1 of the same genotype that does not comprise the modification or substitution(s); improved integrity, stability, or both integrity and stability, of VLPs that are comprised of the modified VP1 proteins as compared to the integrity, stability or both of VLPs comprising wild type VP1 of the same genotype that does not comprise the modification or substitution(s); increased VLP yield when expressed in plant cells as compared to the wild type level of VLP production of the same genotype that does not comprise the modification or substitution(s); a greater proportion of VLPs that assemble into 38 nm VLPs as opposed to 23 nm VLPs as compared to the wild type VP1 of the same genotype that does not comprise the modification or substitution(s); and a combination thereof.

Figure 1A:
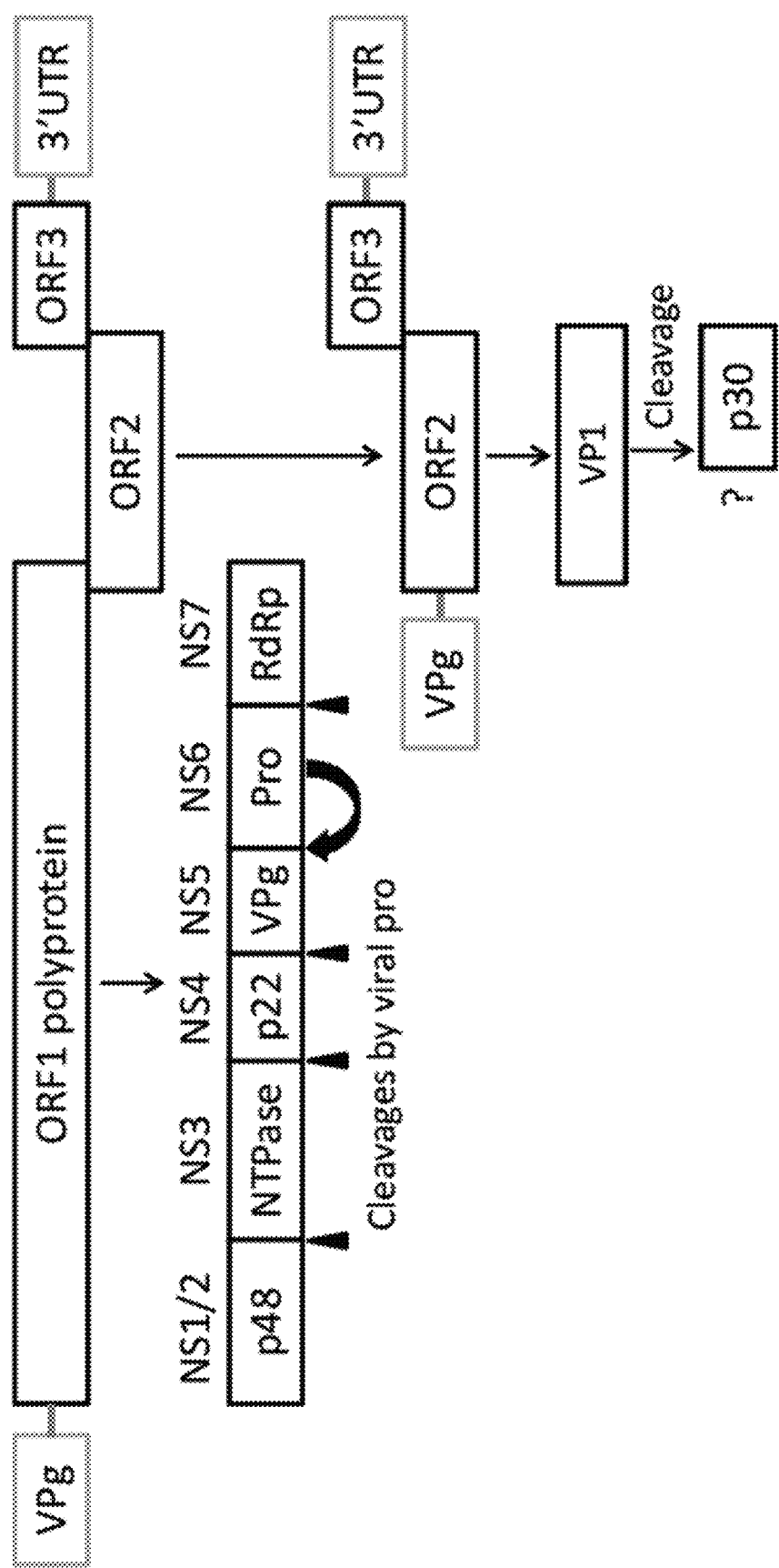
FIG. 1A shows a schematic representation of the linear structure of the norovirus genome and the polyprotein and proteins translated therefrom.
Figure 1C:
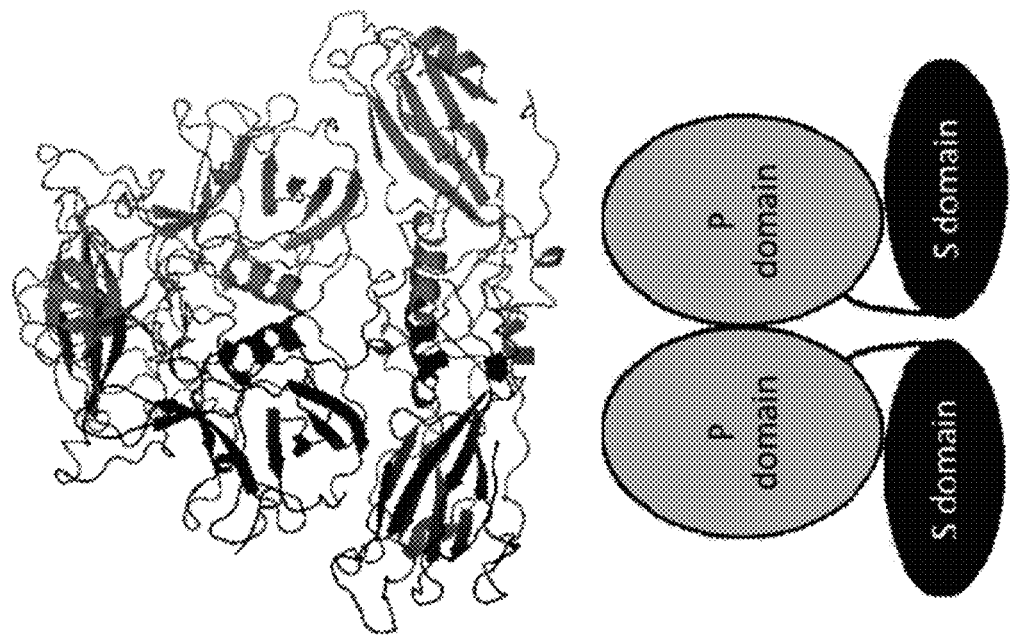
FIG. 1C shows a ribbon diagram representation of the 3-dimensional structure of a norovirus VP1 protein dimer comprising of two S domains (S), two P domains (P).
Figure 1B:
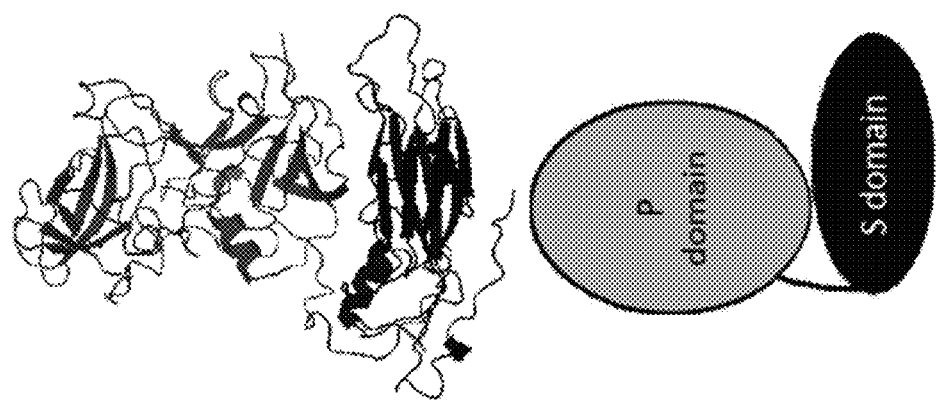
FIG. 1B shows a ribbon diagram representation of the 3-dimensional structure of the norovirus VP1 protein comprising a shell (S) domain, a protruding (P) domain comprising a P1 and a P2 subdomain.
Figure 1D:
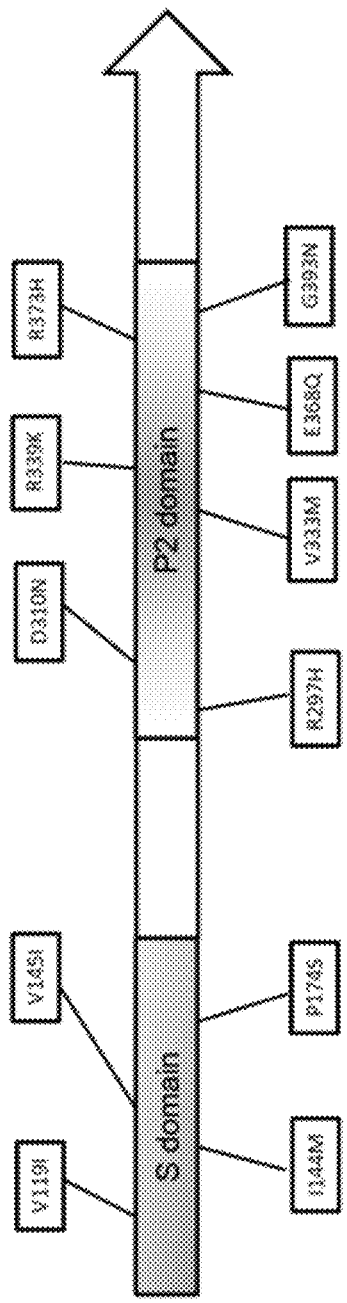
FIG. 1D shows a schematic representation of the linear structure of the norovirus VP1 protein showing the shell (S) domain and the P2 subdomain. Amino acid differences between the two norovirus genotype GII.4/Sydney/2012/K4LM89 (SEQ ID NO:1; also referred to as GII.4/2012, or GII.4/Sydney/NSW0514/2012/AU) and norovirus genotype GII.4/Sydney/2015 (SEQ ID NO:3; also referred to as GII.4/2015; sequence kindly provided by Miranda de Graaf, Erasmus University Medical Center, Rotterdam) are indicated. Single letter amino acid code for the GII.4 2012 amino acid is followed by its position and the single letter amino acid code of the corresponding amino acid in GII.4/2015. There are four amino acid differences in the S-domain (V119I, I144M, V145I and P174S) and seven differences in the P2 domain (R297H, D310N, V333M, R339K, E368Q, R373H and G393N).
Figure 1E:
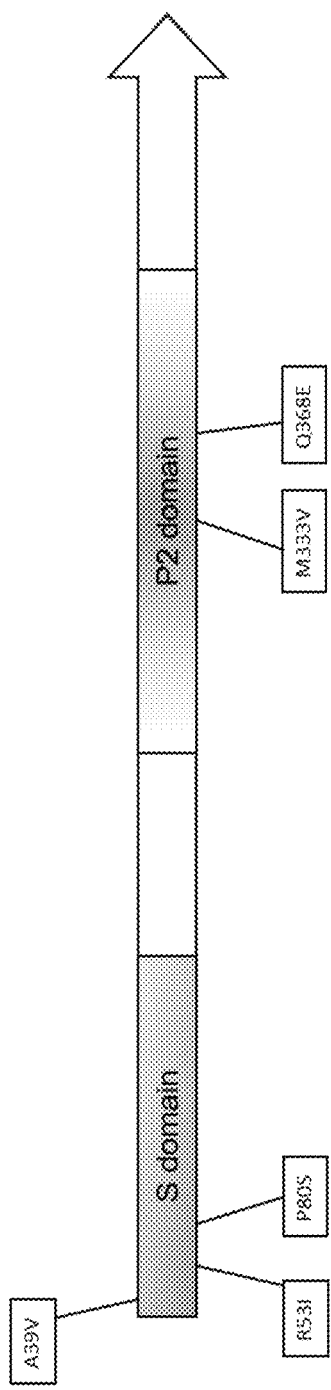
FIG. 1E shows a schematic representation of the linear structure of an example of a modified norovirus VP1 protein of GII.4/2015, showing the shell (S) domain, P2 subdomain. Modifications of the VP1 protein at amino acid positions 39, 53, 80, 333 and 368 are indicated. The numbering of the amino acid residues is in accordance with the numbering of native norovirus genotype GII.4 (GII.4/2012; SEQ ID NO:1). Native amino acid residue is followed by the residue number and the new or substituted amino acid residue.

As shown in FIG. 1D, and Table 1 below, there are 11 differences between GII.4/Sydney/2012/K4LM89 (GII.4/2102; SEQ ID NO:1; FIG. 5A; also referred to as GII.4/Sydney/NSW0514/2012/AU), and GII.4/Sydney/2015 (GII.4/2015; SEQ ID NO:3; FIG. 5C; sequence kindly provided by Miranda de Graaf, Erasmus University Medical Center, Rotterdam). Four of the differences are located in the S domain at positions 119, 144, 145 and 174, and 7 differences are located in the P domain at positions 297, 310, 333, 339, 368, 373 and 393:

TABLE 1

Amino acid differences between GII.4/Sydney/2012/K4LM89 (GII.4/2012; SEQ ID NO:1; FIG. 5A) and GII.4/Sydney/2015 (GII.4/2015; SEQ ID NO:3; FIG. 5C)

| | S domain | | | | P Domain | | | | | | |
|---|---|---|---|---|---|---|---|---|---|---|---|
| aa | 119 | 144 | 145 | 174 | 297 | 310 | 333 | 339 | 368 | 373 | 393 |
| 2012 | V | I | V | P | R | D | V | R | E | R | G |
| 2015 | I | M | I | S | H | N | M | K | Q | H | N |

S Domain Equivalents

One of skill in the art would understand that the S domain of GII.4/2012, comprising an isoleucine at positions 119 and 145, a methionine at position 144, and a serine at position 174 (V119I, I144M, V145I and P174S) is structurally and functionally equivalent to the S domain from GII.4/2015, and for example, that a GII.4/2012 S domain comprising a serine at position 80 (P80S) is structurally and functionally equivalent to a GII.4/2015 S domain comprising P80S, I119V, M144I, I145V and S174P substitutions. As a result:

- GII.4/2012 (P80S) S domain may be used as short hand for GII.4/2015 (P80S, I119V, M144I, I145V, S174P) S domain as these S domains comprise the same sequence;
- GII.4/2012 (A39V, P80S) S domain may be used as short hand for GII.4/2015 (A39V, P80S, I119V, M144I, I145V, S174P) S domain as these S domains comprise the same sequence;
- GII.4/2012 (R53I, P80S) S domain may be used as short hand for "GII.4/2015 (R53I, P80S, I119V, M144I, I145V, S174P) S domain as these S domains comprise the same sequence; and
- GII.4/2012 (A39V, R53I, P80S) S domain may be used as short hand for GII.4/2015 (A39V, R53I, P80S, I119V, M144I, I145V, S174P) S domain as these S domains comprise the same sequence.

P Domain Equivalents

In a similar manner, one of skill in the art would understand that the P domain of GII.4/2012 comprising substitutions R297H, D310N, V333M, R339K, E368Q, R373H, G393N is structurally and functionally equivalent to the P domain from GII.4/2015, and for example, that a GII.4/2015 P domain comprising an M333V substitution is the same as stating a GII.4/2012 P domain comprising the following substitutions: H297R, N310D, K339R, Q368E, H373R, N393G (the amino acid at position 333 is already "V" in GII.4/2012, see Table 1). As a result:

- GII.4/2015 (M333V) P domain may be used as short hand for GII.4/2012 (R297H, D310N, R339K, E368Q, R373H, G393N) P domain as these P domains comprise the same sequence;
- GII.4/2015 (Q368E) P domain may be used as short hand for "GII.4/2012 (R297H, D310N, V333M, R339K, R373H, G393N)" P domain (the amino acid at position 368 is already "E" in GII.4/2012) as these P domains comprise the same sequence; and
- GII.4/2015 (M333V, Q368E) P domain may be used as shorthand for "GII.4/2012 (R297H, D310N, R339K, R373H, G393N)" P domain as these P domains comprise the same sequence.

S+P Domain Equivalents

As one of skill would appreciate, the modified GII.4 VP1 proteins described herein may be obtained by making the appropriate amino acid substitutions to achieve the defined GII.4 VP1 modifications, or for example, the S domain from a GII.4/2012 may be fused to a P domain from a GII.4/2015 along with the desired amino acid substitutions to produce the modified GII.4 VP1 protein described herein. For example, the following modified GII.4 VP1 proteins are structurally and functionally equivalent:

i) GII.4/2012 (P80S) S domain+GII.4/2015(M333V) P domain (a fusion GII.4 VP1);

ii) GII.4/2015 (P80S, I119V, M144I, I145V, S174P) S domain+GII.4/2015 (M333V) P domain (using a GII.4/2015 reference sequence); and iii) GII.4/2012 (P80S) S domain+GII.4/2012 (R297H, D310N, R339K, E368Q, R373H, G393N) P domain (using a GII.4/2012 reference sequence).

Other modified GII.4 VP1 proteins described herein may also be produced, defined, or both produced and defined, in a manner analogous to that as outlined above using a GII.4/2012, a GII.4/2015, or a GII.4/2012+G11.4/2015 fusion, as a reference sequence.

Therefore, the present disclosure provides modified norovirus GII.4 VP1 proteins, and methods of producing the modified norovirus GII.4 VP1 proteins. The modified GII.4 VP1 protein may include a nucleotide sequence encoding a GII.4 VP1 protein comprising:

- an S domain substitution, mutation, or modification, at any one or more amino acid residues 39, 53 and 80 of norovirus VP1 genotype GII.4/Sydney/2012/K4LM89 (GII.4/2012; SEQ ID NO:1; see FIG. 5A; also referred to as Hu/GII.4/Sydney/NSW0514/2012/AU);
- an S domain substitution, mutation, or modification, at any one or more amino acid residues in sequence alignment, or corresponding, with positions 39, 53 and 80 of norovirus VP1 genotype GII.4/2015; or
- an S domain substitution, mutation, or modification, at any one or more amino acid residues in sequence alignment, or corresponding, with positions 39, 53 and 80 of a VP1 of a norovirus genotype GII.4/2012, for example, but not limited to US96/GII.4/Dresden174/1997/DE_AY741811 (SEQ ID NO:5; FIG. 6A), FH02/GII.4/FarmingtonHills/2002/US_AY502023 (SEQ ID NO:6; FIG. 6B), Hnt04:GII.4/Hunter-NSW504D/2004/AU_DQ078814 (SEQ ID NO:7; FIG. 6C), 2006b: GII.4/Shellharbour-NSW696T/2006/AU_EF684915 (SEQ ID NO:8; FIG. 6D) and NO09: GII.4/Orange-NSW001P/2008/AU_GQ845367 (SEQ ID NO:9; FIG. 6E) and,
- a substitution, mutation or modification of P domain at any one or more amino acid residues 333 and 368 of norovirus VP1 genotype GII.4/Sydney/2015 (GII.4/2015; SEQ ID NO:3; FIG. 5C);
- a substitution, mutation or modification of the P domain at any one or more amino acid residues in sequence alignment, or corresponding, with positions 333 and 368 of norovirus VP1 genotype GII.4/2012; or
- a substitution, mutation or modification of the P domain at any one or more amino acid residues in sequence alignment, or corresponding, with positions 333 and 368 of norovirus VP1 genotype GII.4/2015, or a GII.4 VP1 protein having from about 80 to about 100% amino acid sequence similarity, or any amount therebetween, with the sequence defined by SEQ ID NO:3.

The sequence encoding the modified norovirus GII.4 VP1 protein as described above may be optimized for human codon usage, for increased GC content, or a combination thereof.

As described herein, amino acids in the GII.4 VP1 proteins may be substituted, mutated or modified to produce a modified GII.4 VP1 protein. The substitutions, modifications, or mutations at specific positions are not limited to the amino acid substitutions exemplified herewith or as given in the examples as one of skill in the art would understand that amino acids with similar properties may be substituted for the amino acids at the identified positions. For example, the modified GII.4 VP1 protein may contain conserved or conservative substitutions of the amino acid.

The term "residue" refers to an amino acid, and this term may be used interchangeably with the term "amino acid" and "amino acid residue".

As used herein, the term "conserved substitution" or "conservative substitution" refers to the presence of an amino acid residue in the sequence of the GII.4 VP1 protein that is different from, but it is in the same class of amino acid as the described substitution. For example, a nonpolar amino acid may be used to replace a nonpolar amino acid, an aromatic amino acid to replace an aromatic amino acid, a polar-uncharged amino acid to replace a polar-uncharged amino acid, and/or a charged amino acid to replace a charged amino acid). In addition, conservative substitutions can encompass an amino acid having an interfacial hydropathy value of the same sign and generally of similar magnitude as the amino acid that is replacing the corresponding wild type amino acid.

As used herein, the term "nonpolar amino acid" refers to glycine (G, Gly), alanine (A, Ala), valine (V, Val), leucine (L, Leu), isoleucine (I, Ile), and proline (P, Pro); the term Further information about conservative substitutions can be found, for example, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988).

The Blosum matrices are commonly used for determining the relatedness of polypeptide sequences (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity sTable 2.elected. The following table shows examples of conservative amino acid substitutions: Table 2.

TABLE 2

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asa, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

"aromatic residue" (or aromatic amino acid) refers to phenylalanine (F, Phe), tyrosine (Y, Tyr), and tryptophan (W, Trp); the term "polar uncharged amino acid" refers to serine (S, Ser), threonine (T, Thr), cysteine (C, Cys), methionine (M, Met), asparagine (N, Asn) and glutamine (Q, Gln); the term "charged amino acid" refers to the negatively charged amino acids aspartic acid (D, Asp) and glutamic acid (E, Glu), as well as the positively charged amino acids lysine (K, Lys), arginine (R, Arg), and histidine (H, His). Other classification of amino acids may be as follows: amino acids with hydrophobic side chain (aliphatic): Alanine (A, Ala), Isoleucine (I, Ile), Leucine (L, Leu), Methionine (M, Met) and Valine (V, Val); amino acids with hydrophobic side chain (aromatic): Phenylalanine (F, Phe), Tryptophan (W, Trp), Tyrosine (Y, Tyr); amino acids with polar neutral side chain: Asparagine (N, Asn), Cysteine (C, Cys), Glutamine (Q, Gln), Serine (S, Ser) and Threonine (T, Thr); amino acids with electrically charged side chains (acidic): Aspartic acid (D, Asp), Glutamic acid (E, Glu); amino acids with electrically charged side chains (basic): Arginine (R, Arg); Histidine (H, His); Lysine (K, Lys), Glycine G, Gly) and Proline (P, Pro).

Conservative amino acid substitutions are likely to have a similar effect on the activity of the resultant modified GII.4 VP1 protein as the original substitution or modification.

For the modifications described herein, the amino acids may be substituted using very high conserved substitutions, highly conserved substitutions or conserved substitutions as outlined in Table 2, as well as aromatic, polar, polar uncharged, polar neutral, or non-polar, negatively charged, positively charged, hydrophobic amino acids as described above.

For example, the modification P80S, comprises substituting proline at position 80 with serine, an amino acid characterized as having a polar neutral side chain. The glutamine at this position may also be substituted with an alternate amino acid characterized as having a polar neutral side chain, for example either asparagine, cysteine, or threonine, i.e. P80X, where X=S, N, C or T.

The modification A39V that comprises substituting an alanine with valine (an amino acid characterized as having a hydrophobic side chain) at position 39, in addition to valine, alanine may also be substituted with amino acid characterized as having a hydrophobic side chain, for example, isoleucine, leucine, or methionine i.e. A39X, where X=V, I, L or M.

The modification R53I that comprises substituting an arginine with isoleucine (an amino acid characterized as having a hydrophobic side chain) at position 53, in addition to isoleucine, arginine may also be substituted with an amino acid characterized as having a hydrophobic side chain, for example, leucine, valine, alanine or methionine i.e. R53X, where X=I, L, V, A or M.

The modification M333V that comprises substituting an methionine with a valine (an amino acid characterized as having a hydrophobic side chain) at position 333, in addition to valine, methionine may also be substituted with an amino acid characterized as having a hydrophobic side chain, for example, isoleucine or leucine i.e. M333V, where X=V, I L or A.

The modification Q368E that comprises substituting a glutamine at position 368 with glutamic acid (an amino acid characterized as having a polar side chain), in addition to glutamic acid, glutamine may also be substituted with an amino acid characterizes as having a polar side chain, for example asparagine or aspartate i.e. Q368X, where X=E, N or D.

The modified or variant norovirus GII.4 VP1 protein may further be a norovirus GII.4 VP1 fusion protein, comprising an S domain derived from a first norovirus genotype variant fused to a P domain derived from a second norovirus genotype variant, or a portion of the P domain, derived from a second norovirus genotype variant. For example, the S domain derived from a first norovirus genotype variant may be substituted, mutated or modified at any one or more amino acids, or in sequence alignment, or corresponding, with positions, 39, 53 and 80 of norovirus VP1 genotype GII.4/Sydney/2012/K4LM89 (SEQ ID NO:1; see FIG. 5A; also referred to as Hu/GII.4/Sydney/NSW0514/2012/AU), and may be fused to the P domain, or a portion of the P domain, derived from a second norovirus genotype variant, that is modified, substituted, or mutated, at any one or more amino acids, or in sequence alignment, or corresponding, with positions, 333 and 368 of norovirus VP1 genotype GII.4/Sydney/2015 (SEQ ID NO:3; FIG. 5C).

With reference to the sequence shown in FIG. 5A, the norovirus GII.4 sequence GII.4/Sydney/2012/K4LM89 (GII.4/2012; SEQ ID NO:1; also referred to as Hu/GII.4/Sydney/NSW0514/2012/AU) is used as a reference sequence against which the other norovirus VP1 sequences may be aligned.

It has been observed that expression of the modified GII.4 VP1 protein as described herein is increased when compared to the yield of the wild type or native GII.4 VP1 protein obtained from GII.4/Sydney/2015 (GII.4/2015; SEQ ID NO:3), when expressed in the same plant and under the same conditions (compare for example results presented in FIG. 2A with those of FIGS. 3A and 4A).

Additionally, expression of a GII.4 VP1 fusion protein comprising a modified S domain from a VP1 protein of a first norovirus genotype variant and a modified P domain from a VP1 protein obtained from a second (different) norovirus genotype variant, may increase the yield of the VP1 fusion protein, when compared to the yield of a native GII.4 VP1 protein obtained from either the first or from the second norovirus genotype, when expressed in the same plant and under the same conditions. For example, the first norovirus genotype variant may be GII.4/2012, and the second norovirus genotype variant may be GII.4/2015.

Also provided herein are methods of increasing production of GII.4 VLPs comprising modified norovirus GII.4 VP1 proteins, in plants. For example, a method may involve introducing a nucleic acid encoding a modified norovirus GII.4 VP1 protein, as described herein, into the plant, portion of the plant, or plant cell. One or more than one modified norovirus GII.4 VP1 protein may be expressed in a plant, portion of the plant, or plant cell, in order to produce a VLP comprising one or more than one modified norovirus GII.4 VP1 protein. Alternatively, the method may comprise providing a plant, portion of the plant, or plant cell that comprises the nucleic acid encoding the modified norovirus GII.4 VP1 protein as described herein, and expressing the nucleic acid encoding the modified norovirus GII.4 VP1 protein in order to produce a VLP comprising the one or more than one modified norovirus GII.4 VP1 protein.

The methods of producing a VLP comprising a GII.4 VP1 modified protein may also comprise a step of co-expressing a nucleic acid sequence encoding a VP2 protein in the plant, portion of the plant, or plant cell.

The term "single construct" or "single constructs", as used herein, refers to nucleic acid vectors comprising a single nucleic acid sequence. The term "dual construct" or "dual constructs", as used herein, refers to a nucleic acid vector comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumifaciens* suspensions permits co-expression of multiple transgenes.

The nucleic acid comprising encoding a norovirus GII.4 VP1 modified or mutant protein as described herein may further comprise sequences that enhance expression of the norovirus VP1 modified protein in the plant, portion of the plant, or plant cell. Sequences that enhance expression may include, a CPMV enhancer element, or a plant-derived expression enhancer, in operative association with the nucleic acid encoding the norovirus VP1 modified protein. The sequence encoding the VP1 modified or mutant protein may also be optimized for human codon usage, increased GC content, or a combination thereof. Furthermore, a nucleic acid encoding VP2 may be co-expressed along with the sequence encoding the VP1 mutant or modified protein. The co-expression of a nucleic acid encoding VP2 may lead to an increased yield, increased density, increased integrity, or combination thereof, of VLPs that comprise the one or more than one type of VP1 modified or mutant protein.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX (where X=160, 155, 150, 114), for example CPMV 160, CPMVX+ (where X=160, 155, 150, 114), for example CPMV 160+, CPMV-HT+, CPMV HT+[WT115], or CPMV HT+[511] (WO2015/143567; WO2015/103704 which are incorporated herein by reference). The CPMV expression enhancer may be used within a plant expression system comprising a regulatory region that is operatively linked with the CPMV expression enhancer sequence and a nucleotide sequence of interest.

The term "plant-derived expression enhancer", as used herein, refers to a nucleotide sequence obtained from a plant, the nucleotide sequence encoding a 5'UTR. Examples of a plant derived expression enhancer are described in U.S. Provisional Patent Application No. 62/643,053 (Filed Mar. 14, 2018; which is incorporated herein by reference) or in Diamos A. G. et. al. (2016, Front Plt Sci. 7:1-15; which is incorporated herein by reference). The plant-derived expression enhancer may be selected from nbMT78, nbATL75, nbDJ46, nbCHP79, nbEN42, atHSP69, atGRP62, atPK65, atRP46, nb30S72, nbGT61, nbPV55, nbPPI43, nbPM64, and nbH2A86 as described in U.S. 62/643,053). The plant derived expression enhancer may be used within a plant expression system comprising a regulatory region that is operatively linked with the plant-derived expression enhancer sequence and a nucleotide sequence of interest.

The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one type of the modified norovirus GII.4 VP1 protein is expressed in the plant, portion of the plant or the plant cell, the one or more than one modified GII.4 VP1 proteins self or auto-assemble into VLPs. The plant or portion of the plant may be harvested under suitable extraction and purification conditions to maintain the integrity of the VLP, and the VLP comprising the one or more than one type of VP1 mutant (modified) protein may be purified. The one or more than one GII.4 VP1 modified or mutant protein may also be co-expressed with nucleotide sequence encoding VP2, so that the VLP may comprise both modified GII.4 VP1 protein and VP2 protein. The present disclosure also provides for the production of one or more than one type of GII.4 VP1 modified or mutant protein as described herein within a plant, portion of a plant, or plant cell, and the extraction and purification of the one or more than one type of GII.4 VP1 modified or mutant protein from the plant, the portion of the plant, or the plant cell to produce plant matter, a plant extract, or a protein extract, comprising the modified or mutant GII.4 VP1 protein.

Plant matter, a plant extract, or a protein extract comprising the norovirus GII.4 VP1 modified or mutant protein as described herein is also provided. The plant matter, plant extract, or protein extract may be used to induce immunity to norovirus infection in a subject. Alternatively, the GII.4 VP1 modified or mutant protein, or the VLP comprising the GII.4 VP1 modified or mutant protein (and optionally VP2), may be purified or partially purified, and the purified or partially purified preparation may be used to induce immunity to a norovirus infection in a subject.

The present disclosure also provides a composition comprising an effective dose of one or more than one type of modified norovirus GII.4 VP1 protein, or VLPs comprising one or more than one modified norovirus GII.4 VP1 protein, and optionally VP2, for inducing an immune response, and a pharmaceutically acceptable carrier, adjuvant, vehicle, or excipient.

Also provided herein are methods of inducing immunity to a norovirus infection in a subject comprising of administering one or more than one type of mutant (modified) norovirus GII.4 VP1 protein or VLPs comprising one or more than one types of norovirus GII.4 VP1 modified or mutant proteins to a subject orally, intranasally, intramuscularly, intraperitoneally, intravenously, subcutaneously, rectally, or intravaginally.

The term "norovirus", as used herein, refers to a non-enveloped viral strain of the genus norovirus of the family Caliciviridae that is characterized as having a single-stranded, positive-sense RNA. The norovirus genome is 7,654 nucleotides in length. The ORF1 encodes a nonstructural polyprotein that is cleaved by viral 3C-like protease into 6 proteins, including an RNA-dependent RNA polymerase. ORF2 and ORF3 encode a major (VP1) and a minor (VP2) capsid protein, respectively (see FIG. 1A).

Norovirus strains as disclosed herein include any known norovirus strain of the genotype GII.4, but also modifications to known GII.4 norovirus strains that are known to develop on a regular basis over time. In this regard, the intra-genotypic variability of GII.4 is well known (see for example Parra G. I. et. al., 2017 PLOS Pathogens 13(1): e1006136, doi:10.371/journal.ppat.1006136; which is incorporated herein by reference). For example, norovirus strains may include (as described by their amino acids sequences), but are not limited to—GII.4/Sydney/2012/K4LM89 (GII.4/2012; SEQ ID NO:1; FIG. 5A; also referred to as GII.4/Sydney/NSW0514/2012/AU), GII/Sydney/2015 (GII.4/2015; SEQ ID NO:3; FIG. 5C; sequence kindly provided by Miranda de Graaf, Erasmus University Medical Center, Rotterdam), US96/GII.4/Dresden174/1997/DE_AY741811 (SEQ ID NO:5; FIG. 6A), FH02/GII.4/FarmingtonHills/2002/US_AY502023 (SEQ ID NO: 6; to FIG. 6B), Hnt04: GII.4/Hunter-NSW504D/2004/AU_DQ078814 (SEQ ID NO:7; FIG. 6C), 2006b: GII.4/Shellharbour-NSW696T/2006/AU_EF684915 (SEQ ID NO:8; FIG. 6D) and NO09: GII.4/Orange-NSW001P/2008/AU_GQ845367 (SEQ ID NO:9; FIG. 6E). Norovirus strains also include strains having from about 30-100% or any amount therebetween, amino acid sequence identity, to the VP1 protein with any of the above norovirus strains of the strains listed above, provided that the VP1 protein induces immunity to norovirus in a subject, when the VP1 protein is administered to the subject. For example, norovirus strains also include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, with any of the above norovirus strains of the strains listed above, provided that the VP1 protein induces immunity to norovirus in a subject, when the VP1 protein is administered to the subject. Norovirus strains also include strains having from about 80-100% or any amount therebetween, nucleotide sequence identity encoding the VP1 protein with any of the above norovirus strains of the strains listed above, provided that the encoded VP1 protein induces immunity to norovirus in a subject, when the VP1 protein is administered to the subject. For example, norovirus strains also include strains having 80, 82, 84, 86, 88, 90, 92, 94, 96, 98, 100%, or any amount therebetween, nucleotide sequence identity (sequence similarity; percent identity; percent similarity) to the sequence encoding the VP1 protein, with any of the above norovirus strains of the strains listed above, provided that the encoded VP1 protein induces immunity to norovirus in a subject, when the VP1 protein is administered to the subject.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and amino acids of the invention. For example, the BLASTN program (for nucleotide sequences) may use as defaults a wordlength (W) of 11, an expectation (E) of 10, M=5, N=-4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=-4, and a comparison of both strands. Software for performing BLAST analyses is publicly available through the National Center for Biotechnology Information (see URL: ncbi.nlm.nih.gov/).

The term "VP1", as used herein, refers to the norovirus major capsid protein or polypeptide comprising an amino acid sequence similar to the protein or polypeptide encoded by ORF2 of one or more strains of norovirus as described herein. The major capsid protein folds into two principal domains, a shell (S) domain and a protruding (P) domain (see FIG. 1B). The VP1 protein forms a dimer (FIG. 1C) when incorporated into a virion particle, or a VLP. The first portion of the N-terminal of VP1 comprise the S domain, with the remainder of the VP1 polypeptide comprising the P domain. Amino acids of the N-terminal VP1 protein comprise the S domain. When folded, the VP1 assumes a conformation as depicted in FIG. 1B, comprising of a globular S domain (bottom of ribbon structure) and a P domain (top of ribbon structure).

As shown in FIG. 1C, the VP1 protein dimerizes via P-domain interactions. These interactions stabilize the spontaneous assembly of norovirus capsid molecules.

The term "virus like particle", VLP, "virus like particles", or "VLPs", as used herein, refers to a norovirus virus like particle(s) that comprise one or more than one type of norovirus VP1 protein, one or more than one type of VP1 modified or mutant protein, or a combination thereof, and that self-assemble into non-replicating, non-enveloped, non-infectious viral capsid structures lacking all parts of the norovirus genome. For example, the VLP may comprise one type of a modified VP1 protein as described herein, or the VLP may comprise two or more different modified VP1 proteins described herein. Furthermore, the VLP may comprise a VP2 protein. VLPs comprising VP1 protein, VP1+ VP2 protein, modified VP1 protein, or modified VP1 protein+VP2 protein are of the size from about 15 nm to 50 nm or any amount therebetween, for example 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nm, or any amount therebetween. For example, for T=1 icosahedral symmetry, VLPs may be about 23 nm, or for T=3 icosahedral symmetry, VLPs may be from about 38 to about 40 nm.

Figure 3A:
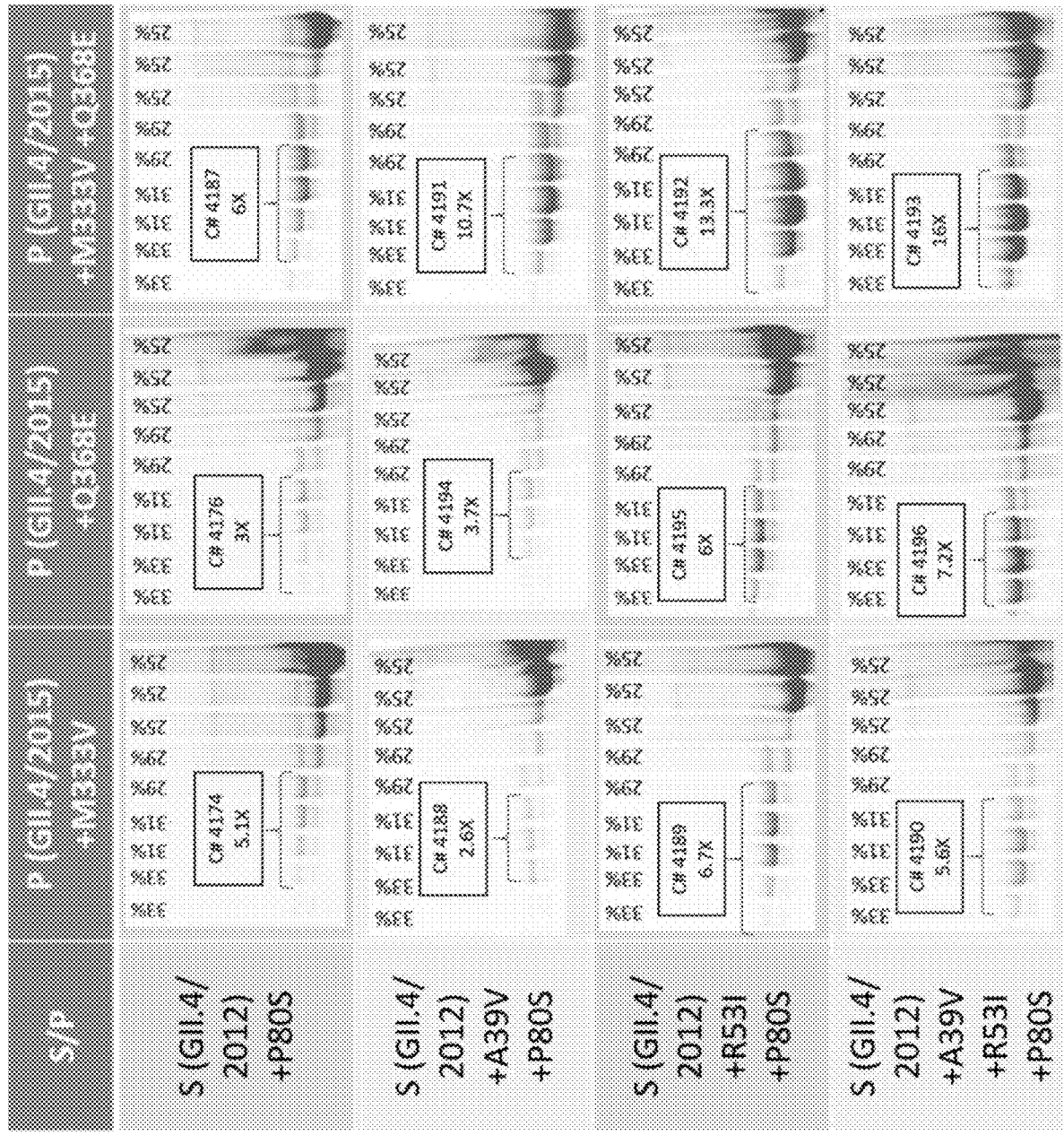
Figure 3B:
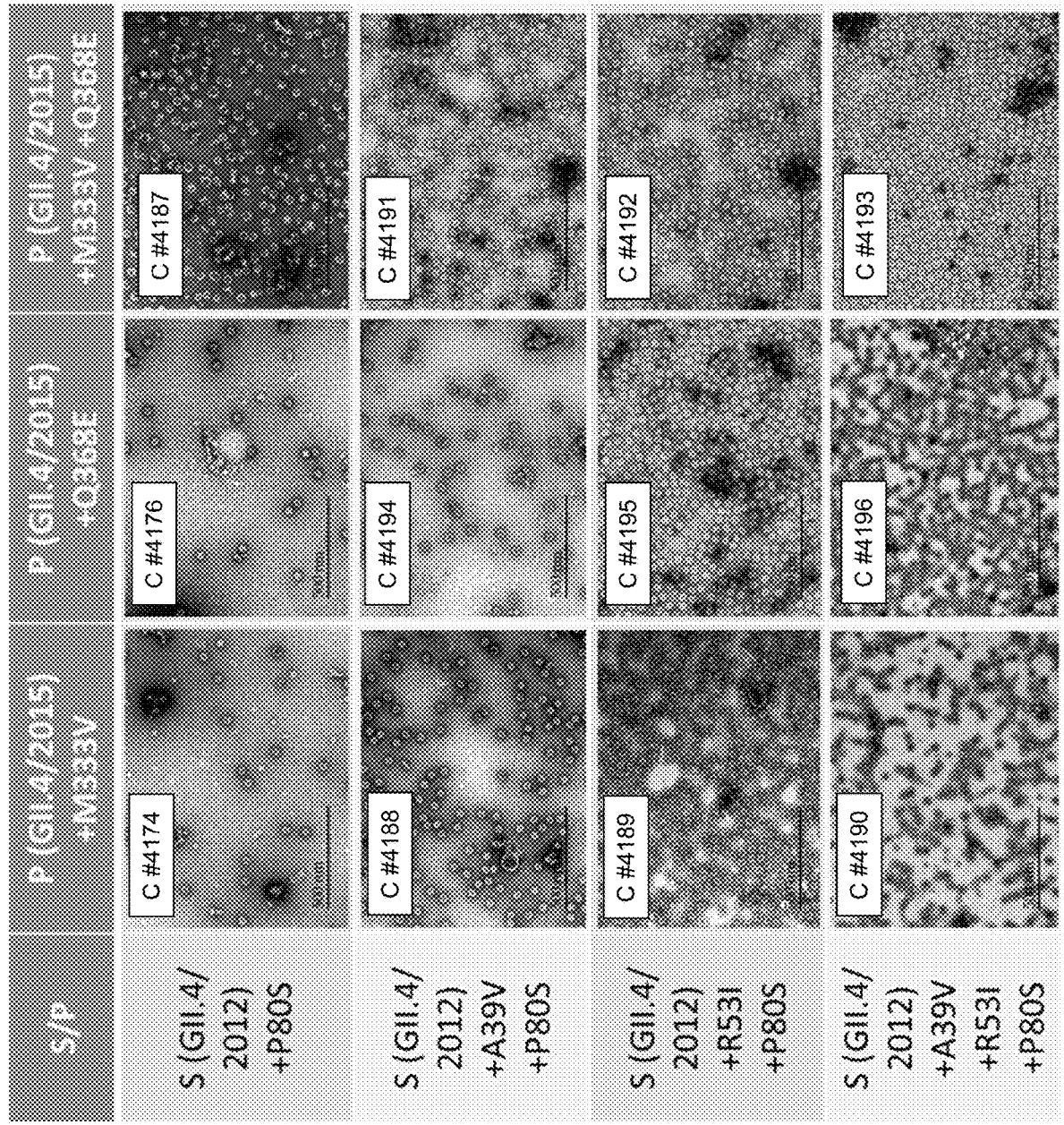

As shown in the electron micrographs of FIGS. 3B and 4B plant produced VP1 proteins and modified VP1 proteins derived from several norovirus GII.4 genotypes self-assemble into VLPs.

Norovirus GII.4 VP1 Protein Production in Plants

The VP1 protein includes any VP1 protein comprising an amino acid sequence having from about 30 to about 100%, from about 40 to about 100%, from about 50 to about 100%, from about 60 to about 100%, from about 70 to about 100%, from about 80 to about 100%, from about 85 to about 100% from about 90 to about 100%, or from about 95 to about 100% from about 98 to about 100%, or any amount therebetween, sequence identity (which may be also termed sequence similarity) with a VP1 amino acid sequence from a norovirus GII.4/Sydney/2012/K4LM89 (GII.4/2012; SEQ ID NO:1; FIG. 5A; also referred to as Hu/GII.4/Sydney/ NSW0514/2012/AU), GII.4/Sydney2015 (SEQ ID NO:3; FIG. 5C), US96/GII.4/Dresden174/1997/DE_AY741811 (SEQ ID NO:5; FIG. 6A), FH02/GII.4/FarmingtonHills/ 2002/US_AY502023 (SEQ ID NO:6; FIG. 6B), Hnt04: GII.4/Hunter-NSW504D/2004/AU_DQ078814 (SEQ ID NO:7 FIG. 6C), 2006b: GII.4/Shellharbour-NSW696T/ 2006/AU_EF684915 (SEQ ID NO:8; FIG. 6D) and NO09: GII.4/Orange-NSW001P/2008/AU_GQ845367 (SEQ ID NO:9; FIG. 6E), provided that the VP1 protein induces immunity to norovirus when administered to a subject.

The modified GII.4 VP1 protein may include a nucleotide sequence encoding a GII.4 VP1 protein comprising, an S domain substitution, mutation, or modification, at any one or more amino acids 39, 53 and 80 of norovirus VP1 protein GII.4/Sydney/2012/K4LM89 (GII.4/2012; SEQ ID NO:1; see FIG. 5A; also referred to as Hu/GII.4/Sydney/ NSW0514/2012/AU); an S domain substitution, mutation, or modification, at any one or more amino acid residues in sequence alignment, or corresponding, with positions 39, 53 and 80 of norovirus VP1 protein GII.4/2015; or an S domain substitution, mutation, or modification, at any one or more amino acids in sequence alignment, or corresponding, with positions 39, 53 and 80 of a VP1 of a norovirus protein GII.4/2012; and a substitution, mutation or modification of P domain at any one or more amino acids 333 and 368 of norovirus VP1 protein GII.4/Sydney/2015 (GII.4/2015; SEQ ID NO:3; FIG. 5C); a substitution, mutation or modification of the P domain at any one or more amino acids in sequence alignment, or corresponding, with positions 333 and 368 of norovirus VP1 protein GII.4/2012; or a substitution, mutation or modification of the P domain at any one or more amino acids in sequence alignment, or corresponding, with positions 333 and 368 of norovirus VP1 protein GII.4/2015.

The modified or variant norovirus GII.4 VP1 protein may further be a norovirus GII.4 VP1 fusion protein, comprising an S domain derived from a first norovirus genotype variant fused to a P domain derived from a second norovirus genotype variant, or a portion of the P domain, derived from a second norovirus genotype variant. For example, the S domain derived from a first norovirus genotype variant may be substituted, mutated or modified at any one or more amino acids, or in sequence alignment, or corresponding, with positions, 39, 53 and 80 of norovirus VP1 genotype GII.4/Sydney/2012/K4LM89 (SEQ ID NO:1; see FIG. 5A; also referred to as Hu/GII.4/Sydney/NSW0514/2012/AU), and may be fused to the P domain, or a portion of the P domain, derived from a second norovirus genotype variant, that is substituted, mutated or modified at any one or more amino acids, or in sequence alignment, or corresponding, with positions, 333 and 368 of norovirus VP1 genotype GII.4/Sydney/2015 (SEQ ID NO:3; FIG. 5C).

The nucleotide sequence encoding the modified norovirus VP1 protein may be optimized for human codon usage, for increased GC content, or a combination thereof. The modified VP1 protein may be expressed in a plant, portion of a plant, or plant cell.

Relative to the hypervariable P domain, the primary amino acid sequence of the norovirus VP1 S domain is well conserved. Similarities of 85-100% were found in the shell domain, whereas the P1 and P2 domains were characterized by lower similarities (75-95%) (Montoya et al. "Molecular Evolution of the VP1 Gene in Human Norovirus GII.4 Variants in 1974-2015", Front. Microbiol. December 2017, Volume 8, Article 2399). These results indicated that the genetic divergence of the VP1 gene in the GII.4 strains differed among domains. For example, nucleic acid sequences described herein may exhibit from about 80 to about 99%, or any amount therebetween sequence identity to the S domain of GII.4 VP1. For example, nucleic acid sequences described herein may exhibit from about 80, 81, 82, 83, 84, 85, 86, 87, 88, 89, 90, 91, 92, 93, 94, 95, 96, 97, 98, 99% or any amount therebetween, sequence identity to the S domain of GII.4 VP1 (GII.4/Sydney/2012/K4LM89; SEQ ID NO:1; also referred to as Hu/GII.4/Sydney/NSW0514/2012/AU). One or more amino acids in sequence alignment, or corresponding, with positions 39, 53 and 80 of norovirus VP1 protein GII.4 (GII.4/Sydney/2012/K4LM89; SEQ ID NO:1) may be modified. Furthermore, the nucleic acid sequences described herein may exhibit from about 80 to about 99%, or any amount therebetween sequence identity to the P domain of GII.4 VP1 (GII.4/Sydney/2012/K4LM89; SEQ ID NO:1). For example, nucleic acid sequences described herein may exhibit from about 80, 81, 82, 83, 84, 85, 86, 87, 88, 89, 90, 91, 92, 93, 94, 95, 96, 97, 98, 99% or any amount therebetween, sequence identity to the P domain of GII.4 VP1 (GII.4/Sydney/2012/K4LM89; SEQ ID NO:1). Furthermore, one or more amino acids in sequence alignment, or corresponding, with positions 333 and 368 of norovirus VP1 protein GII.4/2012 (SEQ ID NO:1) may be modified.

As previously shown (PCT/CA2018/050352, filed Mar. 23, 2018; which is incorporated herein by reference) wild type (also termed native) norovirus VP1 protein may be produced in plants and VLPs comprising the VP1 protein may also be produced. Vacuum infiltration of leaves (from *N. benthamiana*) with *Agrobacterium tumefaciens* comprising expression vectors encoding GI.1 VP1 as a single nucleic acid construct, GI.1 VP2 as a single nucleic acid construct, both GI.1 VP1 and VP2, with VP1 and VP2 nucleic acid sequences introduced in separate vectors ("VP1+VP2"; dual constructs), or on the same vector ("VP1/VP2" or "VP1/VP2/3'UTR"; single nucleic acid constructs) to permit co-expression of the VP1 and/or VP2 sequences and the leaves examined for VP1 and VP2 production. After 6 or 9 days post infiltration (6 DPI and 9 DPI, respectively), total crude protein extracts were prepared from leaf homogenates, separated by SDS-PAGE, and stained with Coomassie Brilliant Blue dye. Leaves infiltrated with expression vectors comprising nucleotide sequences that correspond to wild type GI.1 ORF2, encoding the VP1 protein, produced low or non-detectable levels of GI.1 VP1 as determined using Coomassie stained gels. In contrast, leaves infiltrated with expression vectors comprising GI.1 VP1 nucleotide sequences that were codon optimized for human expression (hCod), or enriched for GC content when compared to the GC content of the wild type VP1 nucleic acid sequence, produced increased amounts of GI.1 VP1 protein in Coomassie stained gels, demonstrating that hCod GI.1 VP1 may be produced in plants when VP1 is expressed on its own.

Furthermore, as described in PCT/CA2018/050352 (filed Mar. 23, 2018; which is incorporated herein by reference), leaves infiltrated with vectors comprising either wild type GI.1 VP1 and VP2 or human codon optimized GI.1 VP1 and VP2 produced low levels of GI.1 VP1 protein in Coomassie stained gels, suggesting that expression of VP1 is not enhanced by the presence of VP2 when co-expressed in cis on the same vector, using the same organization as found in the viral genome (using one promoter to control expression). However, when VP1 or human codon optimized VP1 was co-expressed in trans (on a separate construct) along with VP2 or hCod VP2 (hCod VP1+VP2), respectively, an increase in VP1 protein was observed. Each of the VP1 and VP2 nucleic acid segments comprised a regulatory region and a terminator, and the constructs were introduced into the plants as a nucleic acid complex, and this resulted in a corresponding increase in VP1 protein yield.

This observation is in contrast to that reported in insect and mammalian cells (Bertolotti-Ciarlet A., Crawford S. E., Hutson A. M., Estes M. K. 2003, J. Virol. 77:11603-11615), who reported that an increase in VP1 expression was only observed when VP1 and VP2 (or VP1+VP2+3'UTR) resided in cis, and were co-expressed using the same organization as that found in the viral genome, under the control of one promoter and terminator. No increase in VP1 expression was observed by Bertolotti-Ciarlet (2003) in insect or mammalian cells, when VP1 and VP2 were co-expressed in trans.

The modified VP1 proteins, as described herein, can be co-expressed in plants along with VP2. Co-expression of VP2 protein may involve separate expression systems, for example, if co-expressed on separate plasmids. Alternatively, VP1 and VP2 may be expressed on the same vector but each of the sequences encoding VP1 and VP2 should be under the control of separate promoter and terminator sequences, so that they have a separate expression system.

The yield, or amount of extracted, norovirus GII.4 VP1 protein and the production of VLPs comprising norovirus GII.4 VP1 proteins in a plant, may be improved by modifying one or more than one amino acid in sequence alignment, or corresponding, with amino acid 39, 53, 80, 333 or 368 of norovirus VP1 protein GII.4/2012 (SEQ ID NO:1). The norovirus VP1 proteins with modifications in amino acids 39, 53, 80, 333 and/or 368 as indicated above, formed high density VLPs, having well-formed capsids that are predominantly 38 nm in diameter (See for example FIGS. 3B and 4B).

Figure 2A:
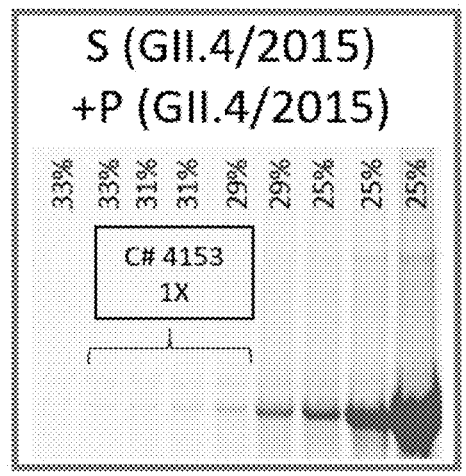
FIG. 2A shows a Coomassie-stained SDS-PAGE analysis of iodixanol density gradient fractions of crude protein extracts prepared from *N. benthamiana* leaves expressing wild type Hu/GII.4/Sydney/2015 (SEQ ID NO:4; kindly provided by Miranda de Graaf, Erasmus University Medical Center, Rotterdam; S(GII.4/2015)+P (GII.4/2015), Construct #: 4153). Protein yield set at "1×" as a reference for comparative protein yields presented in FIGS. 2B, 3A and 4A.
Figure 4A:
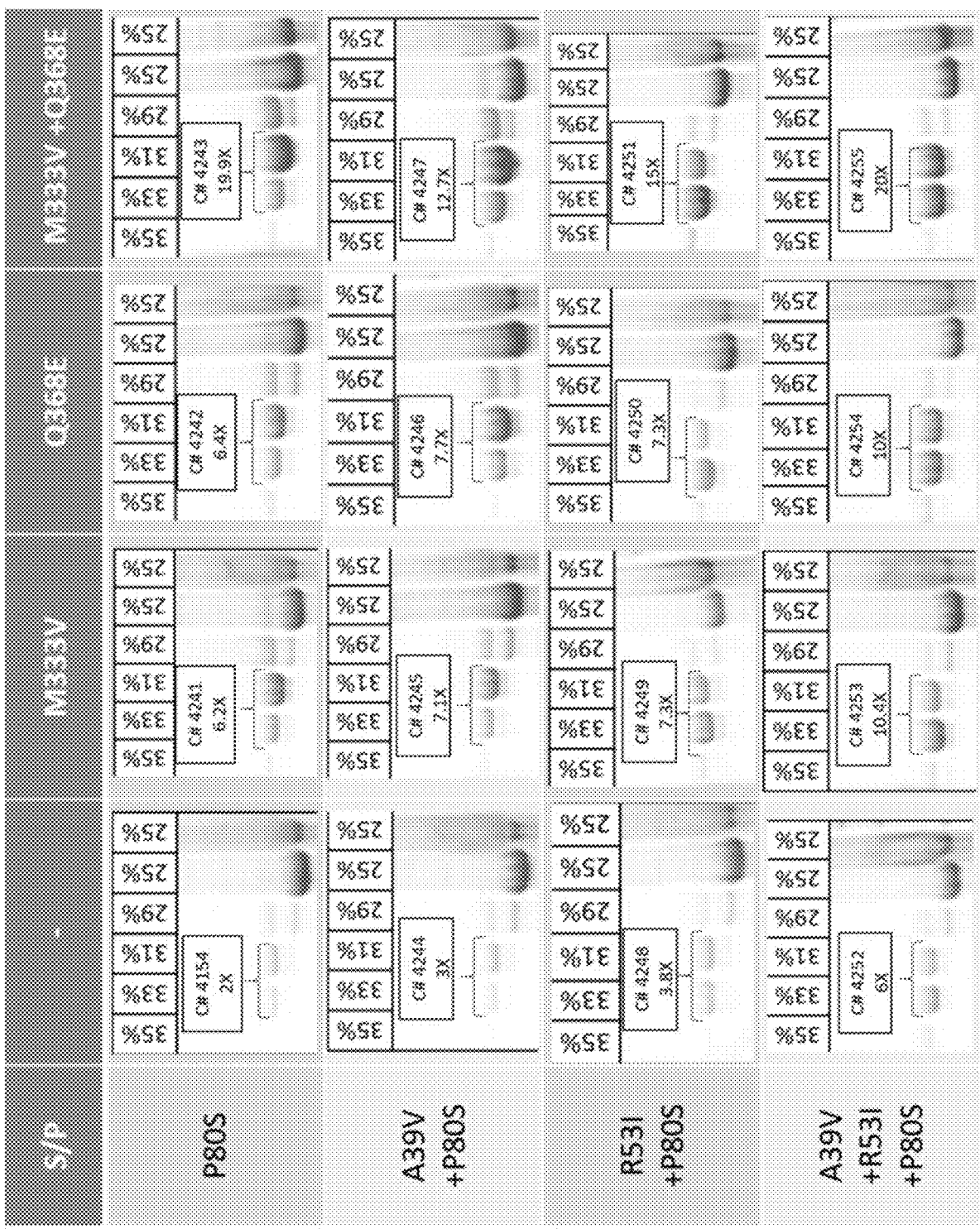
Figure 4B:
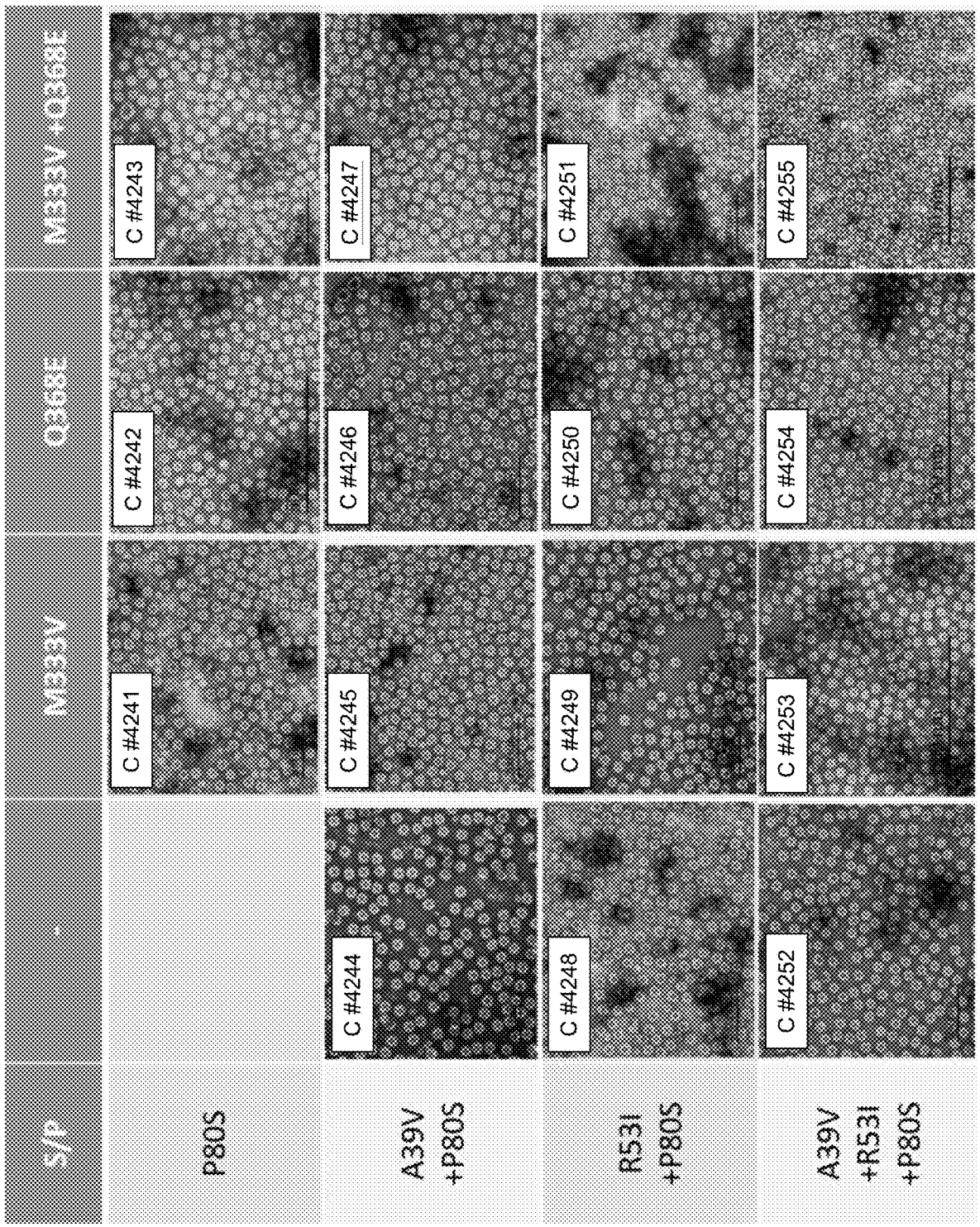

For example, as shown in FIGS. 3A and 4A, the expression of norovirus GII.4 VP1 with modifications of one or more than one amino acids at positions 39 (A39V), 53 (R53I), 80 (P80S), 333 (M333V) or 368 (Q368E) was robust with good protein yields (determined using SDS PAGE) ranging from 2 fold (e.g. construct #4154, FIG. 4A), to over 20 fold (construct #4255; FIG. 4A) when compared to expression of the wild type GII.4/2015 (construct #4153; FIG. 2A). For example, as seen in FIG. 4A, the expression of norovirus VP1 from the genotype variant G11.4/2015, comprising one or more modifications at position 39 (A39V), 53 (R53I) and 80 (P80S) in the S-domain and one or more modifications at positions 333 (M333V) and 368 (Q368E) in the P-domain (for example, but not limited to, construct #4255) was robust and showed higher yields (determined using SDS PAGE), when compared to wild type GII.4/2015 VP1 expression (see FIG. 2A, construct #4153). Furthermore, an increased yield of VP1 protein was produced using each of the constructs shown in FIGS. 3A and 4A (when compared to native GII.4/2015; FIG. 2A), including #4174, #4176, #4187, #4188, #4194, #4191, #4189, #4195, #4192, #4190, #4196, #4193, #4241, #4242, #4243, 4244, #4245, #4246, #4247, #4248, #4249, #4250, #4251, #4252, #4253, #4254, and #4255.

Furthermore, the norovirus VP1 proteins of the GII.4/2015 genotype variant with one or more modifications at position 39 (A39V), 53 (R53I), 80 (P80S), 333 (M333V) and Q368E), or combinations of these modifications, as indicated above, formed high density VLPs, having well-formed capsids that are predominantly 38 nm in diameter (FIG. 4B), see for example, VLP comprising VP1 proteins of the GII.4/2015 genotype variant (see construct #4253; FIG. 4B) with modifications at position 39 (A39V), 53 (R53I), 80 (P80S) and 333 (M333V), and VP1 proteins of the GII.4/2015 genotype variant (see construct #4254; FIG. 4B) with modifications at position 39 (A39V), 53 (R53I), 80 (P80S) and 368 (Q368E). However, VLPs were produced using each of the constructs shown in FIG. 4B, including #4241, #4242, #4243, 4244, #4245, #4246, #4247, #4248, #4249, #4259, #4251, #4252, #4253, #4254, and #4255. In a similar manner, VLPs, having well-formed capsids that are predominantly 38 nm in diameter, were also observed with reference to constructs #4174, #4176, #4187, #4188, #4194, #4191, #4189, #4195, #4192, #4190, #4196, and #4193, as shown in FIG. 3B.

Therefore, the yield, or amount of extracted, norovirus GII.4 VP1 protein and the production of VLPs comprising norovirus GII.4 VP1 proteins in a plant, may be improved by expressing a modified norovirus GII.4 VP1 protein, for example, a GII.4 VP1 fusion protein, comprises an S domain derived from a first norovirus genotype variant fused to a P domain, or a portion of the P domain, derived from a second norovirus genotype variant, wherein the S domain comprising one or more than one substitution, mutation, or modification at a position selected from amino acids in sequence alignment, or corresponding, with amino acid 39, 53 and 80 of norovirus VP1 protein GII.4 (SEQ ID NO:1); the P domain comprising one or more than one modification at a position selected from amino acids in sequence alignment, or corresponding, with amino acids 333 and 368 of norovirus VP1 protein GII.4 (SEQ ID NO:1), or a combination thereof.

However, as noted above (and with reference to Table 1) a GII.4 VP1 fusion protein comprising a modified S domain from a GII.4/2012 genotype and a modified P domain from a GII.4/2015 genotype is structurally and functional equivalent to either a GII.4/2012 genotype of a GII.4/2015 genotype, comprising the corresponding substitutions. For example, an S domain of GII.4/2012, comprising an isoleucine at positions 119 and 145, a methionine at position 144, and a serine at position 174 (V119I, I144M, V145I and P174S) is structurally and functionally equivalent to the S domain from GII.4/2015, and the P domain of GII.4/2012 comprising modifications R297H, D310N, V333M, R339K, E368Q, R373H, G393N is structurally and functionally equivalent to the P domain from GII.4/2015. Therefore, the S(GII.4/2012) nomenclature and defined substitution denoted in FIGS. 3A and 3B (P80S, A39V, and/or R53I) are structurally and functionally equivalent to a S(GII.4/2015 comprising V119I+I144M+V145I+P174S) and the defined substitutions, P80S, A39V, and/or R53I.

As shown in FIG. 3A the production of norovirus VLPs comprising modified VP1 proteins comprising an S-domain of norovirus genotype variant GII.4/Sydney/2012/K4LM89 (referred to as S (GII.4/2012) in FIG. 3A; which is equivalent to an S domain of GII.4/Sydney/2015 comprising I119V, M144I, I145V and S174P, with substitution at position 80 (P80S), positions 39 and 80 (A39V+P80S), positions 53 and 80 (R53I+P80S) or positions 39, 53 and 80 (A39V+R53I+P80S)) and a P-domain of norovirus genotype variant GII.4/Sydney/2015 (referred to as P (GII.4/2015)) with substitutions at position 333 (M333V), position 368 (Q368E) or positions 333 and 368 (M333V+Q368E), was robust with good protein yields that were greater than the yields of native GII.4/2015 (see FIG. 2A; determined using SDS PAGE following iodixanol density gradient centrifugation). The highest yields were obtained by expressing modified norovirus VP1 proteins comprising an GII.4/2012 S-domain (equivalent to GII.4/2015+I119V+M144I+I145V+S174P) with substitutions at (all with reference to FIG. 3A):

position 80 (P80S) and a GII.4/2015 P-domain with substitutions at positions 333 and 368 (M333V+Q368E; construct #4187);

positions 39 and 80 (A39V+P80S) and a GII.4/2015 P-domain with substitutions at positions 333 and 368 (M333V+Q368E; construct #4191);

positions 53 and 80 (R53I+P80S) and a GII.4/2015 P-domain with substitution at positon 333 (M333V; construct #4189);

positions 53 and 80 (R53I+P80S) and a GII.4/2015 P-domain with substitution at position 368 (Q368E; construct #4195);

positions 53 and 80 (R53I+P80S) and a GII.4/2015 P-domain with substitutions at positions 333 and 368 (M333V+Q368E; construct #4192);

positions 39, 53 and 80 (A39V+R53I+P80S) and a GII.4/2015 P-domain with substitution at position 333 (M333V; construct #4190);

positions 39, 53 and 80 (A39V+R53I+P80S) and a GII.4/2015 P-domain with substitution at position 368 (Q368E; construct #4196) and positions 39, 53 and 80 (A39V+R53I+P80S) and a GII.4/2015 P-domain with substitutions at position 333 and 368 (M333V+Q368E; construct #4193).

Furthermore, the modified norovirus GII.4 VP1 proteins with substitutions in amino acids 39, 53, 80, 333 and/or 368 as indicated in FIG. 3A formed high density VLPs, having well-formed capsids that are predominantly 38 nm in diameter (FIG. 3B).

Figure 2B:
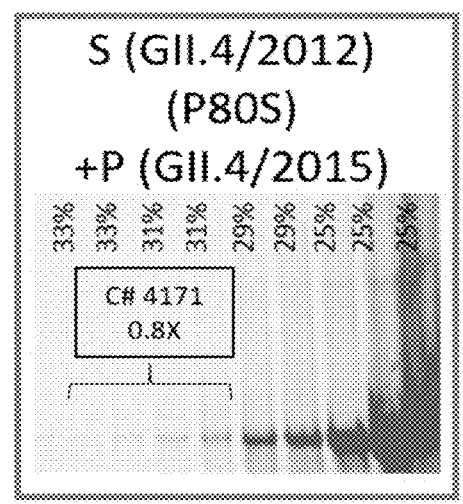
FIG. 2B shows a Coomassie-stained SDS-PAGE analysis of iodixanol density gradient fractions of crude protein extracts prepared from *N. benthamiana* leaves expressing mut GII.4 S/Sydney/2012_P80S_P/Sydney/2015 (S(GII.4/2012(P80S))+P (GII.4/2015)), which is equivalent to: GII.4/2015 (P80S, I119V, M144I, I145V, S174P); Construct #: 4171).

In contrast, wild type VP1 of norovirus GII.4 genotype variant GII.4/Sydney/2015 (GII.4/2015; FIG. 2A construct #4153), or modified norovirus GII.4 comprising S(GII.4/2012 (P80S)+P(GII.4/2015) (FIG. 2B, construct 4171;

equivalent to GII.4/2015 (P80S+I119V+M144I+I145V+S174P)) when expressed in plants exhibited a lower yield of VP1 protein as determined using SDS-PAGE analyses of fractions following gradient centrifugation.

The present disclosure provides nucleic acid sequences encoding modified norovirus GII.4 VP1 proteins, wherein the modified norovirus VP1 comprises one or more than one modification, substitution or mutation at a position selected from a group consisting of amino acids in sequence alignment, or corresponding, with amino acids 39, 53, 80, 333 and 368 of norovirus VP1 protein GII.4 (SEQ ID NO:1). For example, the nucleic acid sequence encoding the modified norovirus GII.4 VP1 protein may comprise an S-domain derived from a first norovirus genotype variant fused to a P domain, or a portion of the P domain, derived from a second norovirus genotype variant, wherein the S domain comprises one or more than one substitution mutation or modification at a position selected from amino acids in sequence alignment, or corresponding, with amino acid 39, 53 and 80 of norovirus VP1 protein GII4/2012 (SEQ ID NO:1); the P domain comprising one or more than one modification at a position selected from amino acids in sequence alignment, or corresponding, with amino acids 333 and 368 of norovirus VP1 protein G11.4/2015 (SEQ ID NO:3, or GII.4/2012, SEQ ID NO:1), or a combination thereof. Alternatively, the nucleic acid sequence may encode a modified GII.4/Sydney/2015 VP1 protein comprising I119V, M144I, I145V and S174P, with one or more than one substitution, mutation, or modification at positions 39, 53, 80, 333 and 368, or a combination thereof.

Plant expressing nucleic acid sequences encoding the modified norovirus G11.4 VP1 protein and comprising one or more than one substitution, mutation, or modification at a position selected from a group consisting of amino acids in sequence alignment, or corresponding, with amino acids 39, 53, 80, 333 and 368 of norovirus VP1 protein GII.4 exhibit improved VP1 characteristics as compared to the wild type GII.4 VP1 that does not comprise the one or more than one substitution, mutation, or modification for example wild type GII.4/Sydney/2015 (SEQ ID NO:3).

Examples of improved characteristics of the modified GII.4 VP1 include, increased modified GII.4 VP1 protein yield (determined for example using Coomassie stained SDS-PAGE and Western analysis) when expressed in plant cells as compared to the wild type VP1 that does not comprise the one or more than one substitution, mutation or modification. For example, increased yields of modified GII.4 VP1 protein may range from 1.5 to 20 fold, or any amount there between, over that of the corresponding wild type VP1 yield;

increased density of VLPs comprising the modified GII.4 VP1 proteins, for example as determined using iodixanol density gradient separation of protein extracts as compared to density gradient separation of the wild type GII.4 VP1 that does not comprise the one or more than one substitution, mutation or modification. For example, VLPs comprising modified GII.4 VP1 protein may be observed in the same or more dense fractions following density gradient centrifugation;

improved integrity of VLPs that are comprised of the modified GII.4 VP1 proteins compared to the wild type GII.4 VP1 that does not comprise the one or more than one substitution, mutation or modification. For example, the number of disrupted, or partially assembled, VLPs may be determined using TEM;

increased VLP yield when expressed in plant cells as compared to the wild type level of VLP production of the same genotype that does not comprise the substitution(s), mutation(s) or modification(s). VLP yield may be determined in washed samples obtained from VLP containing fractions following density gradient centrifugation using TEM. For example, increased yields of VLPs comprising modified GII.4 VP1 protein may range from 1.5 to 20 fold, or any amount there between, over that of the corresponding yield of VLPs comprising wild type VP1 protein;

a greater proportion of VLPs that assemble into 38 nm VLPs as opposed to 23 nm VLPs, compared to VLPs comprising the wild type GII.4 VP1 that does not comprise the one or more than one substitution, mutation or modification (determined using TEM); and a combination of these improved characteristics.

Without wishing to be bound by theory, VLPs that are observed in higher density fractions following density gradient centrifugation, as compared to wild type norovirus VLPs, indicates that the assembly of the VLPs comprising native GII.4 VP1 may be less stable when expressed in, and extracted from, plants, than VLPs comprising the modified VP1 protein. The native VLP may therefore be more susceptible to malformed capsid particles and the generation of fragmentation products. As a result, the VLPs comprising modified GII.4 VP1 protein that are characterized as having increased density may also exhibit greater structural integrity than VLPs produced using the corresponding wild type VP1.

The nucleic acid sequences encoding the modified GII.4 VP1 proteins as described herein may exhibit from about 80% to about 99% sequence similarity (or identity) with a nucleic acid sequences encoding GII.4 VP1, for example, nucleic acid sequences described herein may exhibit from about 80, 81, 82, 83, 84, 85, 86, 87, 88, 89, 90, 91, 92, 93, 94, 95, 96, 97, 98, 99% or any amount therebetween, sequence identity with a nucleic acid sequence encoding a norovirus GII.4 VP1, for example: GII.4/Sydney/2012/K4LM89 (GII.4/2012; SEQ ID NO:1; FIG. 5A; also referred to as GII.4/Sydney/NSW0514/2012/AU), GII/Sydney/2015 (GII.4/2015; SEQ ID NO:3; FIG. 5C), US96/GII.4/Dresden174/1997/DE_AY741811 (SEQ ID NO:5; FIG. 6A), FH02/GII.4/FarmingtonHills/2002/US_AY502023 (SEQ ID NO:6; FIG. 6B), Hnt04:GII.4/Hunter-NSW504D/2004/AU_DQ078814 (SEQ ID NO:7; FIG. 6C), 2006b: GII.4/Shellharbour-NSW696T/2006/AU_EF684915 (SEQ ID NO:8; FIG. 6D) and NO09: GII.4/Orange-NSW001P/2008/AU_GQ845367 (SEQ ID NO:9; FIG. 6E), provided that the modified GII.4 VP1 protein comprises a substitution, mutation or modification at position 39, 53, 80, 333, 368, or a combination thereof, and that the modified GII.4 protein induces immunity to norovirus in a subject, when the VP1 protein is administered to the subject.

Similarly, the present invention includes amino acid sequences that exhibit from about 30% to about 99% or any amount therebetween, sequence similarity with any GII.4 VP1 sequence for example, GII.4/Sydney/2012/K4LM89 (GII.4/2012; SEQ ID NO:1; FIG. 5A; also referred to as GII.4/Sydney/NSW0514/2012/AU), GII/Sydney/2015 (GII.4/2015; SEQ ID NO:3; FIG. 5C), US96/GII.4/Dresden174/1997/DE_AY741811 (SEQ ID NO:5; FIG. 6A), FH02/GII.4/FarmingtonHills/2002/US_AY502023 (SEQ ID NO:6; FIG. 6B), Hnt04:GII.4/Hunter-NSW504D/2004/AU_DQ078814 (SEQ ID NO:7; FIG. 6C), 2006b: GII.4/Shellharbour-NSW696T/2006/AU_EF684915 (SEQ ID NO:8; FIG. 6D) and NO09: GII.4/Orange-NSW001P/2008/

AU_GQ845367 (SEQ ID NO:9; FIG. 6E), provided that the GII.4 VP1 protein induces immunity to norovirus when administered to a subject. For example, the amino acid sequences described herein may have from about 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 91, 92, 93, 94, 95, 96, 97, 98, 99% or any amount therebetween, sequence similarity with any of the GII.4 VP1 amino acid sequences defined above, provided that the VP1 protein induces immunity to norovirus when administered to a subject.

By "VP1 mutant protein", "mutant VP1 protein", "modified VP1 protein", "modified norovirus VP1 protein" and the like, it is meant, a norovirus VP1 protein comprising one or more than one substitution, mutation, or modification, within the amino acid sequence. For example, a GII.4 VP1 modified or mutant protein may comprise one or more substitutions at positions in alignment with amino acids 39, 53, 80, 333 and 368 of norovirus VP1 protein GII.4/2015 (SEQ ID NO:1). The modified VP1 protein may further include a norovirus VP1 fusion protein, comprising an S domain derived from a first norovirus genotype variant fused to a P domain, or a portion of the P domain, derived from a second norovirus genotype variant. The S domain derived from the first norovirus genotype variant may be substituted, mutated or modified at any one or more amino acids in sequence alignment, or corresponding, with positions 39, 53 and 80 of norovirus VP1 protein GII.4/2012 (SEQ ID NO:1; see FIG. 5A). The P domain, or a portion of the P domain, derived from the second norovirus genotype variant may be substituted, mutated or modified at any one or more amino acids in sequence alignment, or corresponding, with positions 333 and 368 of norovirus VP1 protein GII.4/2015 (SEQ ID NO:3, or GII.4/2012, SEQ ID NO:1).

As described herein, modified VP1 proteins comprising one or more than one substitutions of amino acids at positions 39, 53, 80, 333 and 368 in GII.4 strains, resulted in an improved characteristic of the modified VP1 protein, or VLP produced using the modified VP1 protein. It is to be understood that the improved characteristic is not limited to substituting the specific amino acid at the specified sites, since as noted above, one of skill in the art would understand that amino acids with similar properties may be substituted for the amino acids at the identified positions. For example, the modification P80S, comprises substituting proline at position 80 with serine, an amino acid characterized as having a polar neutral side chain. The proline at this position may also be substituted with an alternate amino acid characterized as having a polar neutral side chain, for example either asparagine, cysteine, or threonine, i.e. P80X, where X=S, N, C or T.

The modification A39V that comprises substituting an alanine with valine (an amino acid characterized as having a hydrophobic side chain) at position 39, in addition to valine, alanine may also be substituted with amino acid characterized as having a hydrophobic side chain, for example, isoleucine, leucine, or methionine i.e. A39X, where X=V, I, L or M.

The modification R53I that comprises substituting an arginine with isoleucine (an amino acid characterized as having a hydrophobic side chain) at position 53, in addition to isoleucine, arginine may also be substituted with an amino acid characterized as having a hydrophobic side chain, for example, leucine, valine, alanine or methionine i.e. R53X, where X=I, L, V, A or M.

The modification M333V that comprises substituting a methionine with a valine (an amino acid characterized as having a hydrophobic side chain) at position 333, in addition to valine, methionine may also be substituted with an amino acid characterized as having a hydrophobic side chain, for example, isoleucine or leucine i.e. M333V, where X=V, I or L.

The modification Q368E that comprises substituting a glutamine at position 368 with glutamic acid (an amino acid characterized as having a polar side chain), in addition to glutamic acid, glutamine may also be substituted with an amino acid characterizes as having a polar side chain, for example asparagine or aspartate i.e. Q368X, where X=E, N or D.

Examples of VP1 modified or mutant proteins (modified VP1 proteins) include, but are not limited to, the following.

GII.4_P80S VP1 (GII.4_P80X, where X=S, N, C or T, VP1): wherein the proline corresponding to amino acid 80 of norovirus VP1 protein GII.4/2012 (SEQ ID NO:1, or GII.4/2015, SEQ ID NO:3) has been substituted, mutated, or modified for example, to serine (GII.4_P80S; SEQ ID NO:11, FIG. 7B, SEQ ID NO:13, FIG. 7E, or SEQ ID NO:15, FIG. 7H), or a sequence that exhibits from about 80-100% or any amount therebetween, sequence similarity with the amino acid sequence of the GII.4_P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S VP1 protein as defined in any of SEQ ID NO:11 (FIG. 7B), SEQ ID NO:13 (FIG. 17E), or SEQ ID NO:15 (FIG. 7H), provided that the substitution, mutation or modification at the position corresponding to amino acid 80 of norovirus VP1 protein GII.4 remains a S, N, C or T, for example serine, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_P80S+M333V VP1 (GII.4_P80X, where X=S, N, C or T+M333X, wherein X=V, I or L, VP1): wherein the proline and methionine corresponding to amino acids 80 and 333, respectively, of norovirus VP1 protein GII.4/2015 (SEQ ID NO:3) have been substituted, mutated or modified, for example, to serine and valine, respectively (GII.4_P80S+M333V; SEQ ID NO:17, FIG. 8B, or SEQ ID NO:41, FIG. 12B), or a sequence that exhibits from about 80-100% or any amount therebetween, sequence similarity with the amino acid sequence of GII.4_P80S+M333V VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+M333V VP1 protein as defined in SEQ ID NO:17 (FIG. 8B), or SEQ ID NO:41 (FIG. 12B), provided that the substitutions, mutations or modifications at the positions corresponding to amino acids 80 and 333 of norovirus VP1 protein GII.4 remain a S, N, C or T, for example serine, or a V, I or L for example valine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_P80S+Q368E VP1 (GII.4_P80X, where X=S, N, C or T+Q368E, wherein X=E, N or D, VP1): wherein the proline and glutamine corresponding to amino acids 80 and 368, respectively, of norovirus VP1 protein GII.4/2015 (SEQ ID NO:3) have been substituted, mutated, or modified, for example, to serine and glutamic acid, respectively (GII.4_P80S+Q368E; SEQ ID NO:19, FIG. 8E, or SEQ ID NO:43, FIG. 12E), or a sequence that exhibits from about 80-100% or any amount therebetween, sequence similarity with the amino acid sequence of GII.4_P80S+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+Q368E VP1 protein as defined in SEQ ID NO: 19 (FIG. 8E), or SEQ ID NO:43 (FIG. 12E), provided that the substitutions, mutations or modifications at the positions corresponding to amino acids 80 and 368 of norovirus VP1 protein GII.4 remain a S, N, C or T, for example serine, or a E, N or D for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_P80S+M333V+Q368E VP1 (GII.4_P80X, where X=S, N, C or T+M333X, wherein X=V, I or L +Q368X, wherein X=E, N or D, VP1): wherein the proline, methionine and glutamine corresponding to amino acids 80, 333, and 368 respectively, of norovirus VP1 protein GII.4/2015 (SEQ ID NO:3) have been substituted, mutated, or modified, for example, to serine, valine and glutamic acid, respectively (GII.4_P80S+M333V+Q368E; SEQ ID NO:21, FIG. 8H, or SEQ ID NO:45, FIG. 12H), or a sequence that exhibits from about 80-100% or any amount therebetween, sequence similarity with the amino acid sequence of GII.4_P80S+M333V+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_P80S+M333V+Q368E VP1 protein as defined in SEQ ID NO:21 (FIG. 8H) or SEQ ID NO:45 (FIG. 12H), provided that the substitutions, mutations or modifications at the positions corresponding to amino acids 80, 333 and 368 of norovirus VP1 protein GII.4 remain a S, N, C or T, for example serine, a V, I or L for example valine, or a E, N, D for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

Figure 13I:
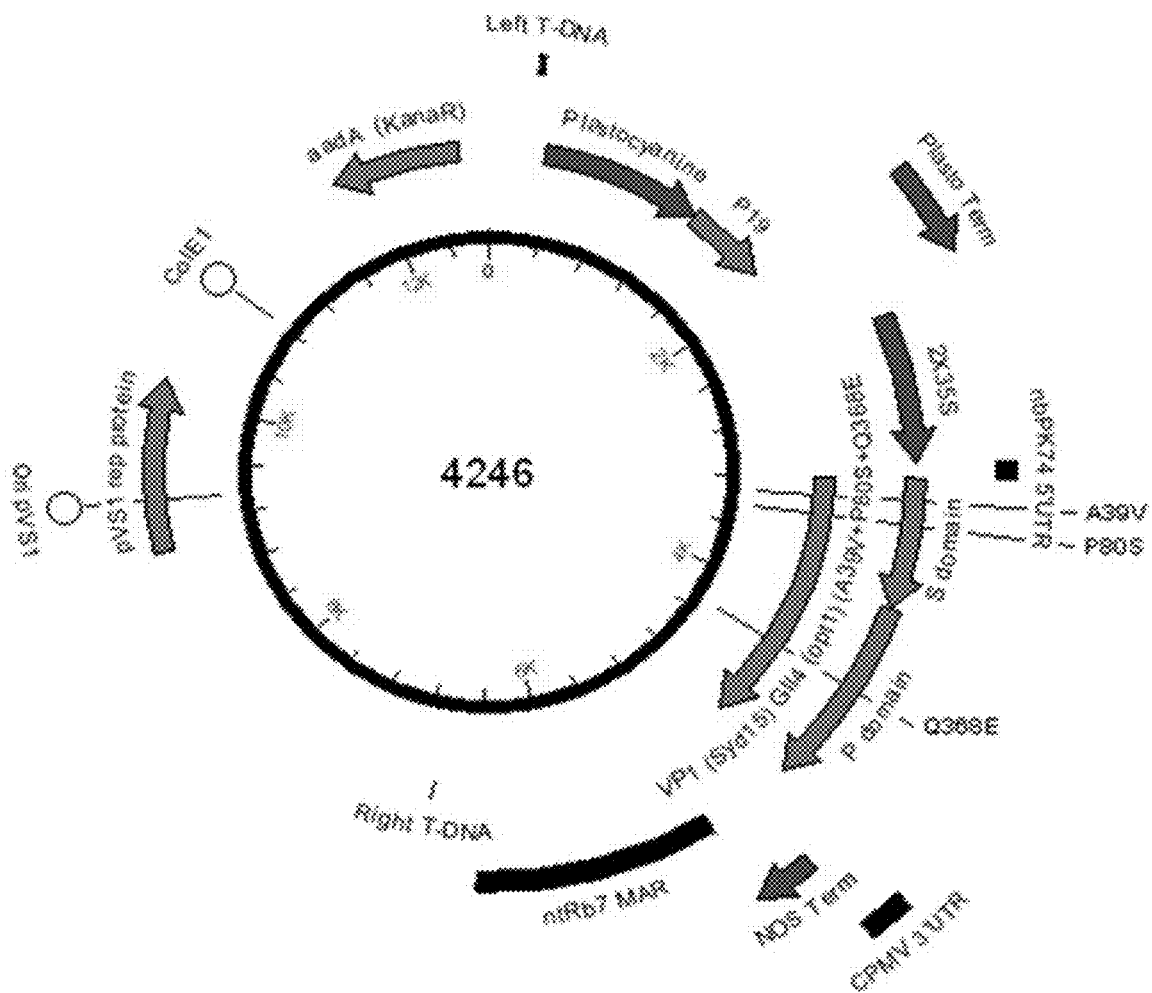

GII.4_A39V+P80S VP1 (GII.4_A39X, where X=V, I, L or M+P80X, where X=5, N, C or T, VP1): wherein the alanine and proline corresponding to amino acids 39 and 80, respectively, of norovirus VP1 protein GII.4/2015 (SEQ ID NO:3) have been substituted, mutated, or modified, for example, to valine and serine respectively (GII.4_A39V+P80S; SEQ ID NO:23, FIG. 9B, or SEQ ID NO:47, FIG. 13B), or a sequence that exhibits from about 80-100% or any amount therebetween, sequence similarity with the amino acid sequence of the GII.4_A39V+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4 A39V+P80S VP1 protein as defined in SEQ ID NO:23 (FIG. 9B), or SEQ ID NO:47 (FIG. 13B), provided that the substitutions, mutations or modifications at the positions corresponding to amino acids 39 and 80 of norovirus VP1 protein GI.4 remain a V, I, L or M, for example valine, and a S, N, C or T, for example serine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4 A39V+P80S+Q368E VP1 (GII.4 A39X, where X=V, I, L or M+P80X, where X=S, N, C or T+Q368X, wherein X=E, N or D, VP1): wherein the alanine, proline and glutamine corresponding to amino acids 39, 80 and 368, respectively, of norovirus VP1 protein GII.4/2015 (SEQ ID NO:3) have been substituted, mutated, or modified, for example, to valine, serine and glutamic acid respectively (GII.4 A39V+P80S+Q368E; SEQ ID NO:25, FIG. 9E, or SEQ ID NO:51, FIG. 13H), or a sequence that exhibits from about 80-100% or any amount therebetween, sequence similarity with the amino acid sequence of the GII.4_A39V+P80S+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4 A39V+P80S+Q368E VP1 protein as defined in SEQ ID NO:25 (FIG. 9E), or SEQ ID NO:51 (FIG. 13H), provided that the ss at the positions corresponding to amino acids 39, 80 and 368 of norovirus VP1 protein GI.4 remain a V, I, L or M, for example valine, a S, N, C or T, for example serine, and a E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4 A39V+P80S+M333V+Q368E VP1 (GII.4 A39X, where X=V, I, L or M+P80X, where X=S, N, C or T+M333X, wherein X=V, I or L+Q368X, wherein X=E, N or D, VP1): wherein the alanine, proline, methionine and glutamine corresponding to amino acids 39, 80, 333 and 368, respectively, of norovirus VP1 protein GII.4/2015 (SEQ ID NO:3) have been substituted, mutated, or modified, for example, to valine, serine, valine and glutamic acid respectively (GII.4 A39V+P80S+M333V+Q368E; SEQ ID NO:27, FIG. 9H, or SEQ ID NO:53, FIG. 13K), or a sequence that exhibits from about 80-100% or any amount therebetween, sequence similarity with the amino acid sequence of the GII.4_A39V+P80S+M333V+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+P80S+ M333V+Q368E VP1 protein as defined in SEQ ID NO:27 (FIG. 9H), or SEQ ID NO:53 (FIG. 13K), provided that the substitutions, mutations or modifications at the positions corresponding to amino acids 39, 80, 333 and 368 of norovirus VP1 protein GII.4 remain a V, I, L or M, for example valine, a S, N, C or T, for example serine, a V, I or L, for example valine, E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_R53I+P80S VP1 (GII.4_R53X, where X=I, L, V, A or M+P80X, where X=S, N, C or T, VP1): wherein the arginine and proline corresponding to amino acids 53 and 80, of norovirus VP1 protein GII.4/2012 (SEQ ID NO:1; or GII.4/2015, SEQ ID NO:3) have been substituted, mutated, or modified, for example, to an isoleucine, a serine and a valine, respectively (GII.4_R53I+P80S; SEQ ID NO:55, FIG. 14B), or a sequence that exhibits from about 80-100% or any amount therebetween, sequence similarity with the amino acid sequence of the GII.4_R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+P80S VP1 protein as defined in SEQ ID NO:55 (FIG. 14B), provided that the substitution, mutation or modification at the position corresponding to amino acids 53 and 80 of norovirus VP1 protein GII.4 remain an I, L, V, A or M, for example isoleucine, and a S, N, C or T, for example serine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_R53I+P80S+M333V VP1 (GII.4_R53X, where X=I, L, V, A or M+P80X, where X=S, N, C or T+M333X, wherein X=V, I or L, VP1): wherein the arginine, proline and methionine corresponding to amino acids 57, 80 and 333, of norovirus VP1 protein GII.4/2015 (SEQ ID NO:3) have been substituted, mutated, or modified, for example, to an isoleucine, a serine and a valine, respectively (GII.4_R53I+P80S+ M333V; SEQ ID NO:29, FIG. 10B, or SEQ ID NO:57, FIG. 14E), or a sequence that exhibits from about 80-100% or any amount therebetween, sequence similarity with the amino acid sequence of the GII.4_R53I+ P80S+M333V VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+ P80S+M333V VP1 protein as defined in SEQ ID NO:29 (FIG. 10B), or SEQ ID NO:57 (FIG. 14E), provided that the substitution, mutation or modification at the position corresponding to amino acids 53, 80 and 333 of norovirus VP1 protein GII.4 remain an I, L, V, A or M, for example isoleucine, a S, N, C or T, for example serine and a V, I or L, for example valine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_R53I+P80S+Q368E VP1 (GII.4_R53X, where X=I, L, V, A or M+P80X, where X=S, N, C or T+Q368X, wherein X=E, N or D, VP1): wherein the arginine, proline and glutamine corresponding to amino acids 57, 80 and 368, of norovirus VP1 protein GII.4/ 2015 (SEQ ID NO:3) have been substituted, mutated, or modified, for example, to an isoleucine, a serine and a glutamic acid, respectively (GII.4_R53I+P80S+ Q368E; SEQ ID NO:31, FIG. 10E, or SEQ ID NO:59, FIG. 14H), or a sequence that exhibits from about 80-100% or any amount therebetween, sequence similarity with the amino acid sequence of the GII.4_R53I+ P80S+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+P80S+ Q368E VP1 protein as defined in SEQ ID NO:31 (FIG. 10E), or SEQ ID NO:59 (FIG. 14H), provided that the substitution, mutation or modification at the position corresponding to amino acids 53, 80 and 368 of norovirus VP1 protein GII.4 remain an I, L, V, A or M, for example isoleucine, a S, N, C or T, for example serine and a E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_R53I+P80S+M333V+Q368E VP1 (GII.4_R53X, where X=I, L, V, A or M+P80X, where X=S, N, C or T+M333X, wherein X=V, I or L+Q368X, wherein X=E, N or D, VP1): wherein the arginine, proline, methionine and glutamine corresponding to amino acids 57, 80, 333 and 368, respectively, of norovirus VP1 protein GII.4/2015 (SEQ ID NO:3) have been substituted, mutated, or modified, for example, to an isoleucine, a serine, a valine and glutamic acid, respectively (GII.4_R53I+P80S+M333V+Q368E; SEQ ID NO:33, FIG. 10H, or SEQ ID NO:61, FIG. 14K), or a sequence that exhibits from about 80-100% or any amount therebetween, sequence similarity with the amino acid sequence of the GII.4_R53I+P80S+ M333V+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_R53I+ P80S+M333V+Q368E VP1 protein as defined in SEQ ID NO:33 (FIG. 10H), or SEQ ID NO:61 (FIG. 14K), provided that the substitution, mutation or modification at the position corresponding to amino acids 53, 80, 333 and 368 of norovirus VP1 protein GII.4 remain an I, L, V, A or M, for example isoleucine, a S, N, C or T, for example serine, a V, I or L, for example valine and a E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

Figure 15C:
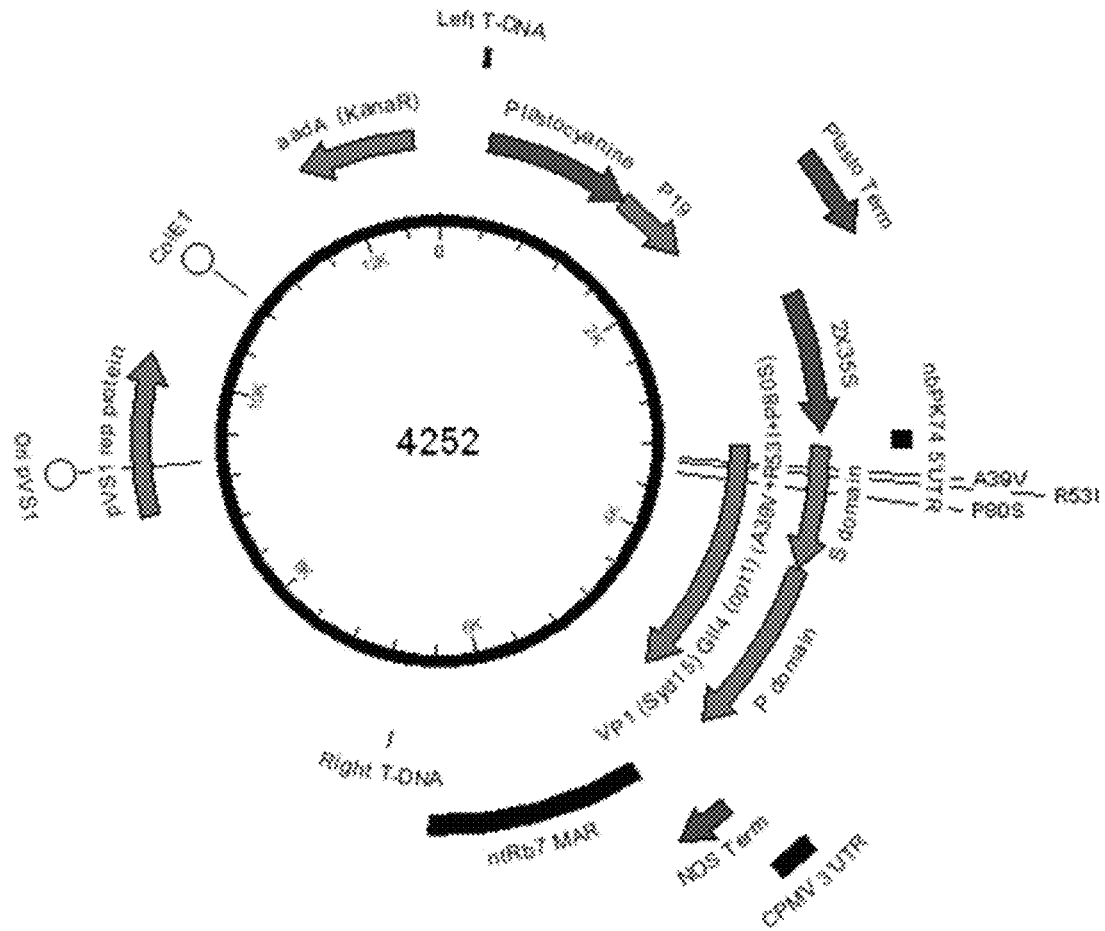
Figures 15F, 15G:
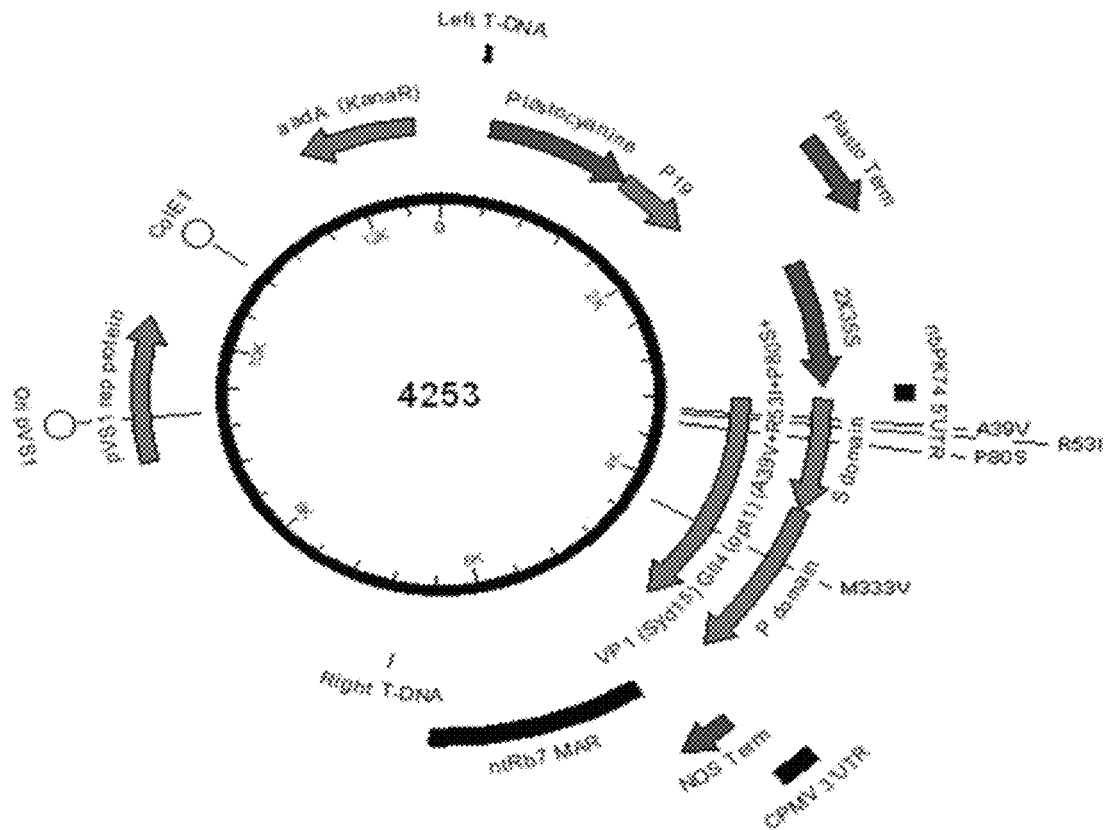

GII.4 A39V+R53I+P80S VP1 (GII.4_A39X, where X=V, I, L or M+R53X, wherein X=I, L, V, A or M+P80X, where X=S, N, C or T, VP1): wherein the alanine, arginine, and proline corresponding to amino acids 39, 53 and 80, respectively, of norovirus VP1 protein GII.4/2012 (SEQ ID NO:1, or GII.4/2015, SEQ ID NO:3) have been substituted, mutated, or modified, for example, to valine, isoleucine and serine, respectively (GII.4 A39V+R53I+P80S; SEQ ID NO:63, FIG. 15B), or a sequence that exhibits from about 80-100% or any amount therebetween, sequence similarity with the amino acid sequence of the GII.4 A39V+R53I+P80S VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S VP1 protein as defined in SEQ ID NO:63 (FIG. 15B), provided that the substitutions, mutations or modifications at the positions corresponding to amino acids 39, 53 and 80 of norovirus VP1 protein GII.4 remain a V, I, L or M, for example valine, an I, L, V, A or M, for example isoleucine, a S, N, C or T, for example serine, and a V, I or L, for example valine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4 A39V+R53I+P80S+M333V VP1 (GII.4 A39X, where X=V, I, L or M+R53X, wherein X=I, L, V, A or M+P80X, where X=5, N, C or T, +M333X, wherein X=V, I or L, VP1): wherein the alanine, arginine, proline and methionine corresponding to amino acids 39, 53, 80 and 333, respectively, of norovirus VP1 protein GII.4/2015 (SEQ ID NO:3) have been substituted, mutated, or modified, for example, to valine, isoleucine, serine and valine, respectively (GII.4 A39V+R53I+P80S+M333V; SEQ ID NO:35, FIG. 11B, or SEQ ID NO:65, FIG. 15E), or a sequence that exhibits from about 80-100% or any amount therebetween, sequence similarity with the amino acid sequence of the GII.4_A39V+R53I+P80S+M333V VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S+ M333V VP1 protein as defined in SEQ ID NO:35 (FIG. 11B), or SEQ ID NO:65 (FIG. 15E), provided that the substitutions, mutations or modifications at the positions corresponding to amino acids 39, 53, 80 and 333 of norovirus VP1 protein GII.4 remain a V, I, L or M, for example valine, an I, L, V, A or M, for example isoleucine, a S, N, C or T, for example serine, and a V, I or L, for example valine, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_A39V+R53I+P80S+Q368E VP1 (GII.4_A39X, where X=V, I, L or M+R53X, wherein X=I, L, V, A or M+P80X, where X=S, N, C or T, +Q368X, wherein X=E, N or D, VP1): wherein the alanine, arginine, proline and glutamine corresponding to amino acids 39, 53, 80 and 368, respectively, of norovirus VP1 protein GII.4/2015 (SEQ ID NO:3) have been substituted, mutated, or modified, for example, to valine, isoleucine, serine and glutamic acid, respectively (GII.4 A39V+R53I+P80S+Q368E; SEQ ID NO:37, FIG. 11E, or SEQ ID NO:67, FIG. 15H), or a sequence that exhibits from about 80-100% or any amount therebetween, sequence similarity with the amino acid sequence of the GII.4_A39V+R53I+P80S+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S+Q368E VP1 protein as defined in SEQ ID NO:37 (FIG. 11E), or SEQ ID NO:67 (FIG. 15H), provided that the substitutions, mutations or modifications at the positions corresponding to amino acids 39, 53, 80 and 368 of norovirus VP1 protein GII.4 remain a V, I, L or M, for example valine, an I, L, V, A or M, for example isoleucine, a S, N, C or T, for example serine, and a E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

GII.4_A39V+R53I+P80S+M333V+Q368E VP1 (GII.4_A39X, where X=V, I, L or M+R53X, wherein X=I, L, V, A or M+P80X, where X=5, N, C or T, +M333X, wherein X=V, I or L+Q368X, wherein X=E, N or D, VP1): wherein the alanine, arginine, proline methionine and glutamine corresponding to amino acids 39, 53, 80 333 and 368, respectively, of norovirus VP1 protein GII.4/2015 (SEQ ID NO:3) have been substituted, mutated, or modified, for example, to valine, isoleucine, serine, valine and glutamic acid, respectively (GII.4 A39V+R53I+P80S+M333V+ Q368E; SEQ ID NO:39, FIG. 11H, or SEQ ID NO:69, FIG. 15K), or a sequence that exhibits from about 80-100% or any amount therebetween, sequence similarity with the amino acid sequence of the GII.4_A39V+R53I+P80S+M333V+Q368E VP1 protein. For example, the GII.4 VP1 protein may have from about 80, 81, 82, 83, 84, 85, 86, 87, 88, 89, 90, 91, 92, 93, 94, 95, 96, 97, 98, 99, 100% or any amount therebetween, sequence similarity with the amino acid sequence of the GII.4_A39V+R53I+P80S+M333V+ Q368E VP1 protein as defined in SEQ ID NO:39 (FIG. 11H), or SEQ ID NO:69 (FIG. 15K), provided that the substitution, mutation or modifications at the positions corresponding to amino acids 39, 53, 80, 333 and 368 of norovirus VP1 protein GII.4 remain a V, I, L or M, for example valine, an I, L, V, A or M, for example isoleucine, a S, N, C or T, for example serine, a V, I or L, for example a valine and a E, N or D, for example glutamic acid, respectively, and provided that the VP1 protein induces immunity to norovirus when administered to a subject. The sequence encoding the GII.4 VP1 may be obtained from any GII.4 strain, for example, but not limited to GII.4/2015 (SEQ ID NO:3, amino acid; SEQ ID NO:4, nucleotide; FIGS. 5C and 5D).

VLP Yield

An example of an improved characteristic of VP1 may be observed comparing the yields of VLPs comprising modified VP1 proteins is shown with reference to FIGS. 3A and 4A. Expression of modified norovirus VP1 proteins comprising one or more than one substitutions of amino acids at positions 39, 53, 80, 333 and 368 in plants resulted in from about 2 to about 20 fold higher VLP yield, when compared to the yield of wild type GII.4/2015 VP1 (see FIG. 2A; yield set to "1").

Additionally, VLPs comprising modified VP1 protein with one or more than one substitution of an amino acid at position 39, 53, 80, 333 and 368 (or corresponding to, or in alignment with, position 39, 53, 80, 333 and 368 of GII.4 VP1) exhibited an increase in VLP yield when compared to the yield of VLPs comprising the corresponding wild type, or native, VP1 protein, for all modified VP1 proteins that were examined.

Increased VP1 protein yield (see FIGS. 3A, 4A) compared to wild type (GII.4/2015; FIG. 2A), and strong VLP production was for example observed in plant extracts expressing:

- mut GII.4 (S/2012_P80S_P/2015_M333V) VP1 (construct 4174; yield 5.1×);
- mut GII.4 (S/2012_P80S_P/2015_Q368E) VP1 (construct 4176; yield 3×);
- mut GII.4 (S/2012_P80S_P/2015_M333V+Q368E) VP1 (construct 4187; yield 6×);
- mut GII.4 (S/2012_A39V+P80S_P/2015_M333V) VP1 (construct 4188; yield 2.6×);
- mut GII.4 (S/2012_A39V+P80S_P/2015 Q368E) VP1 (construct 4194; yield 3.7×);
- mut GII.4 (S/2012_A39V+P80S_P/2015_M333V+Q368E) VP1 (construct 4191; yield 10.7×);
- mut GII.4 (S/2012_R53I+P80S_P/2015_M333V) VP1 (construct 4189; yield 6.7×);
- mut GII.4 (S/2012_R53I+P80S_P/2015_Q368E) VP1 (construct 4195; yield
- mut GII.4 (S/2012_R53I+P80S_P/2015_M333V+Q368E) VP1 (construct 4192; yield 13.3×);
- mut GII.4 (S/2012_A39V+R53I+P80S_P/2015_M333V) VP1 (construct 4190; yield 5.6×);
- mut GII.4 (S/2012_A39V+R53I+P80S_P/2015_Q368E) VP1 (construct 4196; yield 7.2×);
- mut GII.4 (S/2012_A39V+R53I+P80S_P/2015_M333V+Q368E) VP1 (construct 4193; yield 16×);
- mut VP1 GII.4/2015_P80S VP1 (construct 4154; yield 2×);
- mut VP1 GII.4/2015_P80S+M333V (construct 4241; yield 6.2×);
- mut VP1 GII.4/2015_P80S+Q386E (construct 4242; yield 6.4×);
- mut VP1 GII.4/2015_P80S+M333V+Q386E (construct 4243; yield 19.9×);
- mut VP1 GII.4/2015_A39V+P80S (construct 4244 yield 3×);
- mut VP1 GII.4/2015_A39V+P80S+M333V (construct 4245; yield 7.1×);
- mut VP1 GII.4/2015_A39V+P80S+Q386E (construct 4246; yield 7.7×);
- mut VP1 GII.4/2015_A39V+P80S+M333V+Q386E (construct 4247; yield 12.7×);
- mut VP1 GII.4/2015_R53I+P80S (construct 4248; yield 3.8×);
- mut VP1 GII.4/2015_R53I+P80S+M333V (construct 4249; yield 7.3×);
- mut VP1 GII.4/2015_R53I+P80S+Q386E (construct 4250; yield 7.3×);
- mut VP1 GII.4/2015_R53I+P80S+M333V+Q386E (construct 4251; yield 15×);
- mut VP1 GII.4/2015_A39V+R53I+P80S (construct 4252; yield 6×);
- mut VP1 GII.4/2015_A39V+R53I+P80S+M333V (construct 4253; yield 10.4×);
- mut VP1 GII.4/2015_A39V+R53I+P80S+Q386E (construct 4254; yield 10×);
- mut VP1 GII.4/2015_A39V+R53I+P80S+M333V+Q386E (construct 4255; yield 20×).

Size, Density, Stability and Quality of VLPs

As shown in FIGS. 3B and 4B, many of the modified norovirus GII.4 VP1 proteins exhibit the improved characteristic of VLPs having greater densities (determined by Coomassie stained SDS PAGE of iodixanol density gradient fractions of protein extracts), so that the VLPs are observed in higher density fractions, for example, fractions from 29 to 35%, as compared to wild type norovirus GII.4/2015 VP1 (FIG. 2A). Without wishing to be bound by theory, VLPs comprising modified GII.4 VP1 as described herein, may exhibit greater structural integrity than wild type GII.4/2015 VP1. It is also observed that VLPs comprising modified GII.4 VP1 generally comprise a greater relative proportion of 38 nm diameter VLPs vs. 23 nm diameter VLPs than wild type GII.4/2015 VLPs as determined using transmission electron micrography (TEM).

Induction of Immunity Against Norovirus Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-norovirus antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of norovirus.

The term "epitope" or "epitopes", as used herein, refers to a structural part of an antigen to which an antibody specifically binds.

It is also provided herein a method of producing an antibody or antibody fragment comprising, administering a modified norovirus VP1 protein, or a norovirus VLP comprising one or more than one modified VP1 protein to a subject, or a host animal, thereby producing the antibody or the antibody fragment. The modified norovirus VP1 protein comprising one or more than one substitution, mutation or modification at a position selected from amino acids in sequence alignment, or corresponding, with amino acids 39, 53, 80, 333 and 368 of norovirus VP1 genotype GII.4 (SEQ ID NO:1). The VLP may further comprise a norovirus VP2 protein.

There is also provided a composition for inducing an immune response comprising, an effective dose of the VLP comprising the modified norovirus VP1 protein, and a pharmaceutically acceptable carrier, adjuvant, vehicle or excipient.

Plant Expression

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebvre, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100: 247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al. (2987, *Nature* 327: 70-73); Freeman et al. (1984, *Plant Cell Physiol.* 29: 1353), Howell et al. (1980, *Science* 208: 1265), Horsch et al. (1985, *Science* 227: 1229-1231), DeBlock et al. (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth*, 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology, Vol* 483, *pages* 41-50; Liu and Lomonossoff, 2002, *Journal of Virological Methods*, 105:343-348; which is incorporated herein by reference). Alternatively, a vacuum-based transient expression method, as described by Kapila et al. (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy R R D ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

Therefore, there is provided herein, a plant, a portion of a plant, a plant cell, or a plant extract, comprising, one or more than one modified norovirus VP1 protein, or a norovirus VLP comprising one or more than one modified VP1 protein. The one or more than one modified norovirus VP1 protein comprising one or more than one substitution, mutation or modification at a position selected from amino acids in sequence alignment, or corresponding, with amino acids 39, 53, 80, 333 and 368 of norovirus VP1 protein GII.4/2015 (SEQ ID NO:3). The VLP may further comprise a norovirus VP2 protein.

Also provided herein is a plant, portion of a plant, a plant cell, or a plant extract comprising, a nucleic acid or polynucleotide sequence encoding one or more than one modified norovirus VP1 protein. The one or more than one modified norovirus VP1 protein comprising one or more than one substitution, mutation or modification at a position selected from amino acids in sequence alignment, or corresponding, with amino acids 39, 53, 80, 333 and 368 of norovirus VP1 protein GII.4/2015 (SEQ ID NO:3, or GII4/2012, SEQ ID NO:1).

TABLE 3

Norovirus strains and constructs.

| Norovirus VP1 | SEQ ID NO: | FIG. # | Const # | FIG. # |
|---|---|---|---|---|
| Wt GII.4 Syd12 (“GII.4/2012”) (aa) | 1 | 5A | — | — |
| Wt GII.4 Syd12 (“GII.4/2012”) hCod (nt) | 2 | 5B | 3760 | 20A |
| Wt GII.4 Syd15 (“GII.4/2015”) (aa) | 3 | 5C | — | — |
| Wt GII.4 Syd15 (“GII.4/2015”) hCod (nt) | 4 | 5D | 4153 | 5E |
| Wt GII.4 US96/GII.4/Dresden174/1997/DE_AY741811 (aa) | 5 | 6A | — | — |
| Wt GII.4 FH02/GII.4/FarmingtonHills/2002/US_AY502023 (aa) | 6 | 6B | — | — |
| Wt GII.4 Hnt04:GII.4/Hunter-NSW504D/2004/AU_DQ078814 (aa) | 7 | 6C | — | — |
| Wt GII.4 2006b: GII.4/Shellharbour-NSW696T/2006/AU_EF684915 (aa) | 8 | 6D | — | — |
| Wt GII.4 N009/GII.4/Orange-NSW001P/2008/AU_GQ845367 (aa) | 9 | 6E | — | — |
| Mut GII.4/2012 (P80S) hCod (nt) | 10 | 7A | 4152 | 7C |
| Mut GII.4/2012 (P80S) (aa) | 11 | 7B | — | — |
| Mut GII.4/2015 (P80S) hCod (nt) | 12 | 7D | 4154 | 7F |
| Mut GII.4/2015 (P80S) (aa) | 13 | 7E | — | — |
| Mut S(GII.4/2012_P80S) + P(GII.4/2015) hCod (nt) | 14 | 7G | 4171 | 7I |
| Mut S(GII.4/2012_P80S) + P(GII.4/2015) aa | 15 | 7H | — | — |
| Mut S(GII.4/2012_P80S) + P(GII.4/2015_M333V) hCod (nt) | 16 | 8A | 4174 | 8C |
| Mut S(GII.4/2012_P80S) + P(GII.4/2015_M333V) (aa) | 17 | 8B | — | — |
| Mut S(GII.4/2012_P80S) + P(GII.4/2015_Q368E) hCod (nt) | 18 | 8D | 4176 | 8F |
| Mut S(GII.4/2012_P80S) + P(GII.4/2015_Q368E) (aa) | 19 | 8E | — | — |
| Mut S(GII.4/2012_P80S) + P(GII.4/2015_ M333V + Q368E) hCod (nt) | 20 | 8G | 4187 | 8I |
| Mut S(GII.4/2012_P80S) + P(GII.4/2015_ M333V + Q368E) (aa) | 21 | 8H | — | — |
| Mut S(GII.4/2012_A39V + P80S) + P(GII.4/2015_M333V) hCod (nt) | 22 | 9A | 4188 | 9C |
| Mut S(GII.4/2012_A39V + P80S) + P(GII.4/2015_M333V) (aa) | 23 | 9B | — | — |
| Mut VP1 S(GII.4/2012_A39V + P80S) + P(GII.4/2015_Q368E) hCod (nt) | 24 | 9D | 4194 | 9F |
| Mut VP1 S(GII.4/2012_A39V + P80S) + P(GII.4/2015_Q368E) (aa) | 25 | 9E | — | — |
| Mut VP1 S(GII.4/2012_A39V + P80S) + P(GII.4/2015_M333V + Q368E hCod (nt) | 26 | 9G | 4191 | 9I |
| Mut VP1 S(GII.4/2012_A39V + P80S) + P(GII.4/2015_M333V + Q368E (aa) | 27 | 9H | — | — |
| Mut VP1 S(GII.4/2012_R53I + P80S) + P(GII.4/2015_M333V) hCod (nt) | 28 | 10A | 4189 | 10C |
| Mut VP1 S(GII.4/2012_R53I + P80S) + P(GII.4/2015_M333V) (aa) | 29 | 10B | — | — |
| Mut VP1 S(GII.4/2012_R53I + P80S) + P(GII.4/2015_Q368E) hCod (nt) | 30 | 10D | 4195 | 10F |
| Mut VP1 S(GII.4/2012_R53I + P80S) + P(GII.4/2015_Q368E) (aa) | 31 | 10E | — | — |
| Mut VP1 S(GII.4/2012_R53I + P80S) + P(GII.4/2015_M333V + Q368E) hCod (nt) | 32 | 10G | 4192 | 10I |
| Mut VP1 S(GII.4/2012_R53I + P80S) + P(GII.4/2015_M333V + Q368E) (aa) | 33 | 10H | — | — |
| Mut VP1 S(GII.4/2012_A39V + R53I + P80S) + P(GII.4/2015_M333V) hCod (nt) | 34 | 11A | 4190 | 11C |
| Mut VP1 S(GII.4/2012_A39V + R53I + P80S) + P(GII.4/2015_M333V) (aa) | 35 | 11B | — | — |
| Mut (P1 S(GII.4/2012_A39V + R53I + P80S) + P(GII.4/2015_Q368E) hCod (nt) | 36 | 11D | 4196 | 11F |
| Mut VP1 S(GII.4/2012_A39V + R53I + P80S) + P(GII.4/2015_Q368E) (aa) | 37 | 11E | — | — |
| Mut VP1 S(GII.4/2012_A39V + R53I + P80S) + P(GII.4/2015_M333V + Q368E) hCod (nt) | 38 | 11G | 4193 | 11I |
| Mut VP1 S(GII.4/2012_A39V + R53I + P80S) + P(GII.4/2015_M333V + Q368E) (aa) | 39 | 11H | — | — |
| Mut VP1 GII.4/2015_P80S + M333V hCod (nt) | 40 | 12A | 4241 | 12C |
| Mut VP1 GII.4/2015_P80S + M333V (aa) | 41 | 12B | — | — |
| Mut VP1 GII.4/2015_P80S + Q368E hCod (nt) | 42 | 12D | 4242 | 12F |
| Mut VP1 GII.4/2015_P80S + Q368E (aa) | 43 | 12E | — | — |
| Mut VP1 GII.4/2015_P80S + M333V + Q368E (hCod (nt) | 44 | 12G | 4243 | 12I |
| Mut VP1 GII.4/2015_P80S + M333V + Q368E (aa) | 45 | 12H | — | — |
| Mut VP1 GII.4/2015_A39V + P80S hCod (nt) | 46 | 13A | 4244 | 13C |
| Mut VP1 GII.4/2015_A39V + P80S m(aa) | 47 | 13B | — | — |
| Mut VP1 GII.4/2015_A39V + P80S + M333V hCod (nt) | 48 | 13D | 4245 | 13F |
| Mut VP1 GII.4/2015_A39V + P80S + M333V (aa) | 49 | 13E | — | — |
| Mut VP1 GII.4/2015_A39V + P80S + Q386E hCod (nt) | 50 | 13G | 4246 | 13I |

TABLE 3-continued Norovirus strains and constructs.

| Norovirus VP1 | SEQ ID NO: | FIG. # | Const # | FIG. # |
|---|---|---|---|---|
| Mut VP1 GII.4/2015_A39V + P80S + Q386E (aa) | 51 | 13H | — | — |
| Mut VP1 GII.4/2015_A39V + P80S + M333V + Q386E hCod (nt) | 52 | 13J | 4247 | 13L |
| Mut VP1 GII.4/2015_A39V + P80S + M333V + Q386E (aa) | 53 | 13K | — | — |
| Mut VP1 GII.4/2015_R53I + P80S hCod (nt) | 54 | 14A | 4248 | 14C |
| Mut VP1 GII.4/2015_R53I + P80S (aa) | 55 | 14B | — | — |
| Mut VP1 GII.4/2015_R53I + P80S + M333V hCod (nt) | 56 | 14D | 4249 | 14F |
| Mut VP1 GII.4/2015_R53I + P80S + M333V (aa) | 57 | 14E | — | — |
| Mut VP1 GII.4/2015_R53I + P80S + Q386E hCod (nt) | 58 | 14G | 4250 | 14I |
| Mut VP1 GII.4/2015_R53I + P80S + Q386E (aa) | 59 | 14H | — | — |
| Mut VP1 GII.4/2015_R53I + P80S + M333V + Q386E hCod (nt) | 60 | 14J | 4251 | 14L |
| Mut VP1 GII.4/2015_R53I + P80S + M333V + Q386E (aa) | 61 | 14K | — | — |
| Mut VP1 GII.4/2015_A39V + R53I + P80S hCod (nt) | 62 | 15A | 4252 | 15C |
| Mut VP1 GII.4/2015_A39V + R53I + P80S (aa) | 63 | 15B | — | — |
| Mut of VP1 GII.4/2015_A39V + R53I + P80S + M333V hCod (nt) | 64 | 15D | 4253 | 15F |
| Mut of VP1 GII.4/2015_A39V + R53I + P80S + M333V (aa) | 65 | 15E | — | — |
| Mut VP1 GII.4/2015_A39V + R53I + P80S + Q386E hCod (nt) | 66 | 15G | 4254 | 15I |
| Mut VP1 GII.4/2015_A39V + R53I + P80S + Q386E (aa) | 67 | 15H | — | — |
| Mut VP1 GII.4/2015_A39V + R53I + P80S + M333V + Q386E hCod (nt) | 68 | 15J | 4255 | 15L |
| Mut VP1 GII.4/2015_A39V + R53I + P80S + M333V + Q386E (aa) | 69 | 15K | — | — |
| Cloning vector 3674 from left to right T-DNA (nt) | 70 | 16A | 3674 | 16B |
| Construct 4153 from 2X35S promoter to NOS terminator (nt) | 71 | 16C | — | — |
| Construct 4154 from 2X35S promoter to NOS terminator (nt) | 72 | 16D | — | — |

'aa' refers to amino acid sequence;
'nt' refers to nucleotide sequence
Amino acids substitutions in the VP1 are indicated by wild type amino acid residue followed by the residue number and the substituted amino acid residue.

The present invention will be further illustrated in the following examples.

Example 1: Norovirus VP1 Constructs

Examples of candidate native sequences for GII.4 VP1 are publicly available, for example in Genbank. It is to be understood that the examples provided below are to be considered non-limiting, since norovirus strains are known to mutate and evolve on a regular basis over time, and the intra-genotypic variability of GII.4 is well known (see for example Parra G. I. et. al., 2017 PLOS Pathogens 13(1): e1006136, doi:10.371/journal.ppat.1006136; which is incorporated herein by reference). Non-limiting examples of native GII.4 VP1 sequences include:

Hu/GII.4/Sydney/NSW0514/2012/AU (also referred to as GII.4_Sydney_2012_K4LM89; GII.4/2012; SEQ ID NO's:1 and 2; FIGS. 5A and 5B);
Hu/GII.4/Sydney2015 (GII.4/2015; SEQ ID NO's:3 and 4; FIGS. 5C and 5D);
US96/GII.4/Dresden174/1997/DE_AY741811 (GII.4; SEQ ID NO:5; FIG. 6A);
FH02/GII.4/FarmingtonHills/2002/US_AY502023 (GII.4; SEQ ID NO:6; FIG. 6B);
Hnt04:GII.4/Hunter-NSW504D/2004/AU_DQ078814 (GII.4; SEQ ID NO:7; FIG. 6C);
2006b: GII.4/Shellharbour-NSW696T/2006/AU_EF68-4915 (GII.4; SEQ ID NO:8; FIG. 6D);
NO09: GII.4/Orange-NSW001P/2008/AU_GQ845367 (GII.4; SEQ ID NO:9; FIG. 6E).

The primers listed in Table 2 were used to prepare the constructs described below.

TABLE 4 primers used to prepare constructs defined herein.

| Primer | Sequence | SEQ ID NO |
|---|---|---|
| IF(nbPK74)GII.4Syd15(opt1).c | TCTTTGAAATTTCTGCAACAATGAAGATGGCTAGCTCAGACGCCAATCCAAGCG | 74 |
| IF-(Syd15)GII4(opt1).r | ACTAAAGAAAATAGGCCTCTACACGGCTCTCCTGCGGCCTGTACCGTTG | 74 |
| IF(nbPK74)GII.4Syd12.c | TCTTTGAAATTTCTGCAACAATGAAAATGGCCTCGAGTGACGCTAACCCTA | 75 |
| GII.4(P80S).r | GATCGGGTCCCAAGCTGGCCGACCACAGGATTTCTCCTGGCGCATTTCTC | 76 |
| GII.4(P80S).c | AATCCTGTGGTCGGCCAGCTTGGGACCCGATCTGAACCCCTATTTGTCAC | 77 |
| IF-GII4Syd12VP1.r | ACTAAAGAAAATAGGCCTTCAGACAGCCCTGCGTCTGCCAGTCCCATT | 78 |
| G11.4Syd15(opt1)(P80S).r | GTCGGGGCCGAGGGAGGCGCTCCACAGTATCTCTCCAGGAGCGTTTCT | 79 |

TABLE 4-continued primers used to prepare constructs defined herein.

| Primer | Sequence | SEQ ID NO |
|---|---|---|
| GII.4Syd15(opt1)(P80S).c | GATACTGTGGAGCGCCTCCCTCGGCCCCGACCTCAACCCCTATCTGT | 80 |
| GII.4Syd15(opt1) + GII.4Syd121 | GGCTTAGTTCTGCTCTCAACAGTGGGGGCACTAAGAAGATAAAGTCAA | 81 |
| GII.4Syd12 + GII.4Syd15(opt1).c | TGCCCCCCACTGTTGAGAGCAGAACTAAGCCCTTTTCTGTTCCCGTGCT | 82 |
| GII.4Syd15(opt1)(M333V).r | CGTCTGTGTCAGCACGCCCTGGATCTTTCCAACAAAGTCGGGTGTCCC | 83 |
| GII.4Syd15(opt1)(M333V).c | TGGAAAGATCCAGGGCGTGCTGACACAGACGACAAAGACAGATGGTTCA | 84 |
| GII.4Syd15(opt1)(Q368E).r | ATCTGTATCTGTCTCAAACTGCACTCTACCGAGTTTTGGTGCGAAATCG | 85 |
| GII.4Syd15(opt1)(Q368E).c | CGGTAGAGTGCAGTTTGAGACAGATACAGATCACGACTTTGAAGCCAAC | 86 |
| VP1_GII.4Syd12(A39V).r | GACCGGCCACGGGGACTGCTATGGCTGCGCCCACCACAGGCTCCAGGGCCATCA | 87 |
| VP1_GII.4Syd12(A39V).c | GGGCGCAGCCATAGCAGTCCCCGTGGCCGGTCAGCAGAATGTGATTGACCCGTG | 88 |
| VP1_GII.4Syd12(R53I).r | TGGACAAAATTGTTGATTATCCACGGGTCAATCACATTCTGCTGACCG | 89 |
| VP1_GII.4Syd12(R53I).c | GATTGACCCGTGGATAATCAACAATTTTGTCCAAGCCCCTGGTGGGAGT | 90 |
| VP1(Syd15)GII4(opt1)(A39V).r | TGCCCAGCAACAGGCACAGCTATAGCAGCTCCAACCACGGGCTCAAGG | 91 |
| VP1(Syd15)GII4(opt1)(A39V).c | TGGAGCTGCTATAGCTGTGCCTGTTGCTGGGCAGCAGAACGTGATAGA | 92 |
| VP1(Syd15)GII4(opt1)(R53I).r | CAAAGTTGTTGATTATCCATGGGTCTATCACGTTCTGCTGCCCAGCAACAG | 93 |
| VP1(Syd15)GII4(opt1)(R53I).c | TGATAGACCCATGGATAATCAACAACTTTGTTCAGGCCCCGGTGGAG | 94 |

2×35S/atPK74/VP1 GII.4-Sydney 2015 (hCod)/NOS+MAR (Construct number 4153)

A human codon-optimized sequence encoding VP1 from Norovirus strain GII.4/Sydney/2015 was cloned into 2×35S/nbPK74/CPMV 3'UTR/NOS expression system using the following PCR-based method. A fragment containing the GII.4 VP1 coding sequence was amplified using primers IF(nbPK74)GII.4Syd15(opt1).c (SEQ ID NO: 73) and IF-(Syd15)GII4(opt1).r (SEQ ID NO: 74), using human codon-optimized GII.4/Sydney 2015 VP1 gene sequence (SEQ ID NO: 4) as template. For sequence optimization, a GII.4/Sydney 2015 strain protein sequence (SEQ ID NO: 3) was backtranslated and optimized for human codon usage, GC content and mRNA structure. The PCR product was cloned in 2×35S/nbPK74/CPMV 3'UTR/NOS expression system using In-Fusion cloning system (Clontech, Mountain View, CA). Construct number 3674 (SEQ ID NO:70, FIG. 16A; construct schematic FIG. 16B) was digested with AatII and StuI restriction enzyme and the linearized plasmid was used for the In-Fusion assembly reaction. Construct number 3674 is an acceptor plasmid intended for "In Fusion" cloning of genes of interest in a 2×35S/nbPK74/CPMV 3'UTR/NOS-based expression cassette along with the MAR regulatory element. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is included in SEQ ID NO:70. The resulting construct was given number 4153 (SEQ ID NO:71). The amino acid sequence of native VP1 from Norovirus strain GII.4/Sydney 2015 is presented in SEQ ID NO: 3. A representation of plasmid 4153 is presented in FIG. 5E.

2×35S/nbPK74/GII.4-Sydney 2015_P80S (hCod)/CPMV 3'UTR/NOS+MAR (Construct Number 4154)

A human codon-optimized sequence encoding VP1 from strain GII.4/Sydney/2015 strain comprising a P80S substitution in the S domain was cloned into 2×35S/nbPK74/CPMV3'UTR/NOS+MAR expression system using the following PCR-based method. In a first round of PCR, a fragment containing the S domain with the modified P80S amino acid was amplified using primers IF(nbPK74)GII.4Syd15(opt1).c (SEQ ID NO:73) and GII.4Syd15(opt1)(P80S).r (SEQ ID NO:79), using human codon-optimized GII.4/Sydney 2015 VP1 gene sequence (SEQ ID NO:4) as template. A second fragment containing the P80S substitution with the remaining of the S and P domain was amplified using GII.4Syd15(opt1)(P80S).c (SEQ ID NO:80) and IF-(Syd15)GII4(opt1).r (SEQ ID NO:74), using human codon-optimized GII.4/Sydney 2015 VP1 gene sequence (SEQ ID NO:4) as template. For sequence optimization, a GII.4/Sydney 2015 strain protein sequence (SEQ ID NO:3) was backtranslated and optimized for human codon usage, GC content and mRNA structure. The PCR product was cloned in 2×35S/nbPK74/CPMV 3'UTR/NOS expression system using In-Fusion cloning system (Clontech, Mountain View, CA). Construct number 3674 (FIG. 16B) was digested with AatII and StuI restriction enzyme and the linearized plasmid was used for the In-Fusion assembly reaction. Construct number 3674 is an acceptor plasmid intended for "In Fusion" cloning of genes of interest in a 2×35S/nbPK74/CPMV 3'UTR/NOS-based expression cassette along with the MAR regulatory element. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is included in SEQ ID NO:70. The resulting construct was given number 4154 (SEQ ID NO:72). The amino acid sequence of modified GII.4/Sydney 2015_P80S is presented in SEQ ID NO:13. A representation of plasmid 4154 is presented in FIG. 7F.

A summary of the wildtype and modified VP1 proteins, primers, templates and products is provided in Tables 3 and 4. The modified VP1 proteins were assembled using the same methods as described above.

Example 2: Methods

*Agrobacterium tumefaciens* Transfection

*Agrobacterium tumefaciens* strain AGL1 was transfected by electroporation with the native norovirus VP1, native norovirus VP2, or norovirus VP1 modified protein expression vectors using the methods described by D'Aoust et al., 2008 (*Plant Biotech. J.* 6:930-40). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions Agrobacteria transfected with each native norovirus VP1, native norovirus VP2, or norovirus VP1 modified expression vector were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 2 volumes of cold 100 mM phosphate buffer pH 7.2+150 mM NaCl, 0.4 μg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, California) using bovine serum albumin as the reference standard. Proteins were separated by SDS-PAGE under reducing conditions using Criterion™ TGX Stain-Free™ precast gels (Bio-Rad Laboratories, Hercules, CA). Proteins were visualized by staining the gels with Coomassie Brilliant Blue. Alternatively, proteins were visualized with Gel Doc™ EZ imaging system (Bio-Rad Laboratories, Hercules, CA) and electrotransferred onto polyvinylene difluoride (PVDF) membranes (Roche Diagnostics Corporation, Indianapolis, Indiana) for immunodetection. Prior to immunoblotting, the membranes were blocked with 5% skim milk and 0.1% Tween-20 in Tris-buffered saline (TBS-T) for 16-18 h at 4° C.

Protein Analysis and Immunoblotting

Immunoblotting was performed with a first incubation with a primary mAb 242P antibody specific to VP1 from GI and GII genotypes, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection, diluted in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Analysis of VLP Formation/Iodixanol Gradients

Proteins were extracted from frozen biomass by mechanical extraction in a blender with 2 volumes of extraction buffer (100 mM phosphate buffer pH 7.2+150 mM NaCl). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%, 2 ml at 31%, 2 ml at 29% and 5 ml at 25% of iodixanol) were prepared and overlaid with 25 ml of the extracts containing the virus-like particles. The gradients were centrifuged at 175,000 g for 4 hours (4° C.). After centrifugation, 1 ml fractions were collected from the bottom to the top and fractions were analyzed by SDS-PAGE combined with protein staining or Western blot.

Electron Microscopy

Following centrifugation of partially clarified plant extracts on discontinuous iodixanol density gradients, as described above, fractions (1 ml/fraction) containing the samples are pooled, mixed with 100 mM PBS pH 7.2+150 mM NaCl buffer to completely fill the tube and centrifuged 120 minutes at 100000 g. The pellets were re-suspended in 300-1000 µl of buffer depending of the VP1 quantity. Protein content was analyzed by BCA.

Carbon-coated copper grids with a 200 nm mesh size. Pooled elution are made hydrophilic by placing the carbon side face up on a Whatman paper in a petri dish and incubated overnight at 4° C. 20 µl of pooled fractions from density gradient centrifugation to be observed by transmission electron microscopy (TEM) are deposited on a Parafilm and grids were floated with the carbon side facing down and incubated at room temperature for 5 minutes. Grids are then washed 4 times on 20 µl water droplet and the excess water from the last wash is drained by touching a Whatman paper with the side of the grid. Grids are then incubated 1 minute on a 20 µl droplet of 2% uranyl acetate in water. Grids are allowed to dry 5 minutes on a Whatman paper. Observation was performed under transmission electron microscopy at magnifications ranging from 10,000× to 150,000×.

Example 3: VP1 Protein and VLP Production in Plants

*N. benthamiana* leaves were, vacuum infiltrated, as described in Example 2, with *Agrobacterium tumefaciens* comprising expression vectors encoding wild type norovirus VP1s or modified norovirus VP1 constructs to permit expression of the VP1 sequences, and the leaves examined for VP1 protein and/or VLP production. After 9 days post infiltration (DPI), total crude protein extracts were prepared from leaf homogenates were separated by SDS-PAGE, and stained with Coomassie (VP1 production), or separated using discontinuous iodixanol density gradients as described in Example 2, above (VLP production). Fractions from the density gradients were examined using Coomassie-stained SDS-PAGE. Norovirus VP1 proteins appear at an approximate 55-60 kDa band. The occurrence of the VP1 protein within a fraction of the density gradients is indicative of the fraction(s) to which the VLPs equilibrate during density gradient centrifugation. The yield of VLPs obtained from peak fractions after density gradient centrifugation was also determined.

Wild type GII.4/2015 genotype variant Hu/GII.4_Sydney/2015 VP1 was poorly expressed in plants (FIG. 2A).

In contrast, modified norovirus VP1 proteins, wherein the GII.4 VP1 protein is substituted, mutated, or modified at any one or more amino acids in sequence alignment, or corresponding, with positions 39, 53, 80, 333 and 368 of norovirus VP1 protein GII.4 (SEQ ID NO:1), resulted in higher yield (FIGS. 3A and 4A) than the wild type GII.4/2015 VP1, and produced VLPs comprising the modified VP1 protein as shown in FIGS. 3B and 4B (the fold increase in yield presented in FIGS. 3A and 4B, and below, is relative to the yield obtained following expression of GII.4/2015 which is set at "1×"; FIG. 2A):

mut GII.4 (S/2012_P80S_P/2015_M333V) VP1 (construct 4174; yield 5.1×);
mut GII.4 (S/2012_P80S_P/2015_Q368E) VP1 (construct 4176; yield 3×);
mut GII.4 (S/2012_P80S_P/2015_M333V+Q368E) VP1 (construct 4187; yield 6×);
mut GII.4 (S/2012_A39V+P80S_P/2015_M333V) VP1 (construct 4188; yield 2.6×);
mut GII.4 (S/2012_A39V+P80S_P/2015_Q368E) VP1 (construct 4194; yield 3.7×);
mut GII.4 (S/2012_A39V+P80S_P/2015_M333V+Q368E) VP1 (construct 4191; yield 10.7×);
mut GII.4 (S/2012_R53I+P80S_P/2015_M333V) VP1 (construct 4189; yield 6.7×);
mut GII.4 (S/2012_R53I+P80S_P/2015_Q368E) VP1 (construct 4195; yield 6×);
mut GII.4 (S/2012_R53I+P80S_P/2015_M333V+Q368E) VP1 (construct 4192; yield 13.3×);
mut GII.4 (S/2012_A39V+R53I+P80S_P/2015_M333V) VP1 (construct 4190; yield 5.6×);
mut GII.4 (S/2012_A39V+R53I+P80S_P/2015_Q368E) VP1 (construct 4196; yield 7.2×);
mut GII.4 (S/2012_A39V+R53I+P80S_P/2015_M333V+Q368E) VP1 (construct 4193; yield 16×);
mut VP1 GII.4/2015_P80S VP1 (construct 4154; yield 2×);
mut VP1 GII.4/2015_P80S+M333V (construct 4241; yield 6.2×);
mut VP1 GII.4/2015_P80S+Q386E (construct 4242; yield 6.4×);
mut VP1 GII.4/2015_P80S+M333V+Q386E (construct 4243; yield 19.9×);
mut VP1 GII.4/2015_A39V+P80S (construct; 4244 yield 3×);
mut VP1 GII.4/2015_A39V+P80S+M333V (construct 4245; yield 7.1×);
mut VP1 GII.4/2015_A39V+P80S+Q386E (construct 4246; yield 7.7×);
mut VP1 GII.4/2015_A39V+P80S+M333V+Q386E (construct 4247; yield 12.7×);
mut VP1 GII.4/2015_R53I+P80S (construct 4248; yield 3.8×);
mut VP1 GII.4/2015_R53I+P80S+M333V (construct 4249; yield 7.3×);
mut VP1 GII.4/2015_R53I+P80S+Q386E (construct 4250; yield 7.3×);
mut VP1 GII.4/2015_R53I+P80S+M333V+Q386E (construct 4251; yield 15×);
mut VP1 GII.4/2015_A39V+R53I+P80S (construct 4252; yield 6×);
mut VP1 GII.4/2015_A39V+R53I+P80S+M333V (construct 4253; yield 10.4×);
mut VP1 GII.4/2015_A39V+R53I+P80S+Q386E (construct 4254; yield 10×);
mut VP1 GII.4/2015_A39V+R53I+P80S+M333V+Q386E (construct 4255; yield 20×).

All citations are hereby incorporated by reference.

The present invention has been described with regard to one or more embodiments. However, it will be apparent to persons skilled in the art that a number of variations and modifications can be made to the described subject matter. The scope of the claims should not be limited by the preferred embodiments set forth in the examples but should be given the broadest interpretation consistent with the description as a whole.

SEQUENCE LISTING

<160> NUMBER OF SEQ ID NOS: 94

<210> SEQ ID NO 1
<211> LENGTH: 540
<212> TYPE: PRT
<213> ORGANISM: Norovirus

<400> SEQUENCE: 1

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365
```

```
Thr Asp Thr Asp Arg Asp Phe Glu Ala Asn Gln Asn Thr Lys Phe Thr
370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
530                 535                 540

<210> SEQ ID NO 2
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/Sydney/2012/K4LM89

<400> SEQUENCE: 2
atgaaaatgg cctcgagtga cgctaaccct agtgacggca cgccgccaa tcttgtgcct        60 gaggttaata atgaggtgat ggccctggag cctgtggtgg gcgcagccat agcagtcccc      120
gtggccggtc agcagaatgt gattgacccg tggatacgca caatttttgt ccaagccct      180 ggtggggagt tcaccgttag cccgagaaat gcgccaggag aaatcctgtg gtcggcccca      240
ttgggacccg atctgaaccc ctatttgtca catctcgctc ggatgtacaa cgggtatgcc      300
ggcggatttg aagtgcaggt gattctggct gggaacgcgt tcactgctgg caaagtgatc      360
tttgcagcgg tgcctcccaa cttccccact gaaggactgt ctccaagcca ggtcacaatg      420
tttccacaca tcgtggtgga cgtacggcag ctagagcctg tcctgattcc cctccctgat      480
gtacgcaata atttctacca ctacaatcaa tccaatgatc cgaccattaa actcatcgcg      540
atgttgtaca cccctctgcg cgctaacaat gctggagacg acgtattcac cgtgtcatgc      600
agagtgctca ccagaccttc accagacttt gactttatct tcttagtgcc ccccactgtt      660
gagagccgaa ccaagccctt tagtgtcccc gtactcacag tcgaggagat gacaaatagc      720
cgctttccaa tccccttgaa aactgttc acaggacctt cctcggcatt cgtggttcag      780
ccacagaacg gacgctgcac aactgacggc gtgctgctcg aaccacccca gcttagccct      840
gttaatatct gtacgtttag aggcgacgta actcacataa ctggctcacg gaactatacc      900
atgaatctgg catcacagaa ttggaatgac tacgacccaa ccgaagagat tcccgcacct      960
cttgaacccc ccgactttgt gggaaaaata cagggcgtcc tgacacaaac caccagaacc     1020
gatggctcca cacggggaca caaggcaacc gtctacactg ctctgccga ttttgccccg     1080
```

```
aaactgggta gagtgcagtt tgagaccgac actgaccggg actttgaagc caatcagaat    1140
actaagttca cacctgtagg agtgattcag gacgggggca ccactcaccg gaacgagccg    1200
caacaatggg tcctgccctc ttatagcggg aggaatactc ataatgtgca tttggctcct    1260
gcagtggctc ccacgtttcc cggggaacaa ctgctctttt ttcgttcaac catgcctgga    1320
tgctccggat atcccaatat ggatctcgat tgcctgctcc cacaggaatg ggtgcagtat    1380 tttatcaag aggccgcacc agcccaatcc gacgtcgcac ttctgcggtt cgtgaatcca    1440
gacacaggcc gcgtgttgtt tgagtgcaaa ttgcacaaat caggatacgt tacagtggct    1500
catactggac agcatgacct ggtgatccca cccaacggat atttaggtt cgactcctgg    1560 gtgaatcagt tttatacatt agcccccatg gggaatggga ctggcagacg cagggctgtc    1620
tga                                                                 1623
```

<210> SEQ ID NO 3
<211> LENGTH: 540
<212> TYPE: PRT
<213> ORGANISM: Norovirus

<400> SEQUENCE: 3

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270
```

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 4
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 Hu/GII.4/Sydney/2015

<400> SEQUENCE: 4
atgaagatgg ctagctcaga cgccaatcca agcgacggta gcgctgccaa cctcgtgccc      60
gaggtcaaca cgaagttat ggcccttgag cccgtggttg gagctgctat agctgctcct     120
gttgctgggc agcagaacgt gatagaccca tggatacgta caactttgt tcaggccccc     180 ggtggagagt ttacagtcag cccaagaaac gctcctggag agatactgtg gagcgcccca     240
ctcggccccg acctcaaccc ctatctgtca catctcgctc gcatgtataa cggctatgct     300
ggcggttttg aagttcaggt catccttgcc ggaaacgcct tcaccgctgg aagataatc     360 tttgctgctg tccacccaa ctttccaact gagggcctga gcccaagcca ggttacaatg     420
tttccacaca tgatagttga tgtcagacag ctggagccag tccttatacc cctgcccgat     480

```
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca aactatact     900
atgaacctgg ccagccagaa ctggaacaac tacgacccaa cagaggagat ccctgctcca    960
cttgggacac ccgactttgt tggaaagatc cagggcatgc tgacacagac gacaaagaca   1020
gatggttcaa caagaggtca caaagctact gtttacaccg gctctgccga tttcgcacca   1080
aaactcggta gagtgcagtt tcagacagat acagatcacg actttgaagc caaccagaac   1140
actaagttta caccagtcgg agttatccga gacggcaaca caacacacag aaacgagcca   1200
cagcaatggg tccttccaag ctatagcggc cggaacacac acaacgttca ccttgctccc   1260
gccgttgctc caacatttcc cggggagcag cttctttct tccgctctac aatgcccggg    1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtccttt tgagtgcaag ctccataaga gcggatatgt gacagtcgct    1500
catactggcc agcacgacct cgttatccct cctaacggtt acttccgatt tgatagctgg   1560
gttaaccagt ttacacact gcccctatg ggcaacggta caggccgcag agagccgtg    1620
tag                                                                 1623
```

<210> SEQ ID NO 5
<211> LENGTH: 539
<212> TYPE: PRT
<213> ORGANISM: Norovirus

<400> SEQUENCE: 5

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile

```
                    165                 170                 175
Lys Leu Ile Ala Met Leu Tyr Thr Pro Leu Lys Ala Asn Asn Ala Gly
                180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
        210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Ala Leu
    530                 535

<210> SEQ ID NO 6
<211> LENGTH: 540
<212> TYPE: PRT
<213> ORGANISM: Norovirus

<400> SEQUENCE: 6
```

-continued

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Leu Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Met Leu Thr Gln
                325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
```

```
                    420             425             430
Phe Phe Arg Ser Thr Met Pro Gly Cys Ser Gly Tyr Pro Asn Met Asn
            435             440             445

Leu Asp Cys Leu Leu Pro Gln Glu Trp Val Gln His Phe Tyr Gln Glu
    450             455             460

Ala Ala Pro Ala Gln Ser Asp Val Ala Leu Leu Arg Phe Val Asn Pro
465             470             475             480

Asp Thr Gly Arg Val Leu Phe Glu Cys Lys Leu His Lys Ser Gly Tyr
                485             490             495

Val Thr Val Ala His Thr Gly Gln His Asp Leu Val Ile Pro Pro Asn
            500             505             510

Gly Tyr Phe Arg Phe Asp Ser Trp Val Asn Gln Phe Tyr Thr Leu Ala
            515             520             525

Pro Met Gly Asn Gly Thr Gly Arg Arg Arg Ala Leu
            530             535             540

<210> SEQ ID NO 7
<211> LENGTH: 540
<212> TYPE: PRT
<213> ORGANISM: Norovirus

<400> SEQUENCE: 7

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Val Leu Ser Pro Ser Gln Val Thr Met Phe Pro His Ile
130                 135                 140

Ile Val Asp Val Arg Gln Leu Glu Pro Val Leu Ile Pro Leu Pro Asp
145                 150                 155                 160

Val Arg Asn Asn Leu Tyr His Tyr Asn Gln Ser Asn Asp Pro Thr Ile
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255
```

```
Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Ala Gly Thr Gln Asn Tyr Thr Met Asn Leu Ala
        290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Arg Phe Thr
370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
450                 455                 460

Ser Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
530                 535                 540

<210> SEQ ID NO 8
<211> LENGTH: 540
<212> TYPE: PRT
<213> ORGANISM: Norovirus

<400> SEQUENCE: 8

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95
```

-continued

```
Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
            115                 120                 125

Pro Thr Glu Gly Leu Ser Pro Ser Gln Val Thr Met Phe Pro His Ile
            130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                    165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
            210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
            275                 280                 285

Asp Val Thr His Ile Ala Gly Ser Arg Asn Tyr Thr Met Asn Leu Ala
            290                 295                 300

Ser Leu Lys Trp Asn Lys Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Asp Gly Ser Thr Arg Gly His Lys Ala Thr Ile Tyr
            340                 345                 350

Thr Gly Ser Ala Pro Phe Thr Pro Lys Leu Gly Ser Val Gln Phe Ser
            355                 360                 365

Thr Asp Thr Glu Asn Asp Phe Glu Thr His Gln Asn Thr Lys Phe Thr
            370                 375                 380

Pro Val Gly Val Thr Gln Asp Gly Ser Thr Thr His Arg Asn Glu Pro
385                 390                 395                 400

Gln Gln Trp Val Leu Pro Ser Tyr Ser Gly Arg Asn Val His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln His Phe Tyr Gln Glu
            450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510
```

```
Gly Tyr Phe Arg Phe Asp Ser Trp Val Asn Gln Phe Tyr Thr Leu Ala
            515                 520                 525

Pro Met Gly Asn Gly Thr Gly Arg Arg Ala Leu
            530                 535                 540

<210> SEQ ID NO 9
<211> LENGTH: 540
<212> TYPE: PRT
<213> ORGANISM: Norovirus

<400> SEQUENCE: 9

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Met Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350
```

```
Thr Gly Ser Ala Asp Phe Ser Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540

<210> SEQ ID NO 10
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2012_P80S

<400> SEQUENCE: 10
atgaaaatgg cctcgagtga cgctaaccct agtgacggca gcgccgccaa tcttgtgcct      60
gaggttaata tgaggtgat ggccctggag cctgtggtgg gcgcagccat agcagcgccc      120
gtggccggtc agcagaatgt gattgacccg tggatacgca acaattttgt ccaagccct      180 ggtggggagt tcaccgttag cccgagaaat gcgccaggag aaatcctgtg gtcggccagc      240
ttgggacccg atctgaaccc ctatttgtca catctcgctc ggatgtacaa cgggtatgcc      300
ggcggatttg aagtgcaggt gattctggct gggaacgcgt tcactgctgg caaagtgatc      360
tttgcagcgg tgcctcccaa cttccccact gaaggactgt ctccaagcca ggtcacaatg      420
tttccacaca tcgtggtgga cgtacggcag ctagagcctg tcctgattcc cctccctgat      480
gtacgcaata atttctacca ctacaatcaa tccaatgatc cgaccattaa actcatcgcg      540
atgttgtaca cccctctgcg cgctaacaat gctggagacg acgtattcac cgtgtcatgc      600
agagtgctca ccagaccttc accagacttt gactttatct tcttagtgcc ccccactgtt      660
gagagccgaa ccaagccctt agtgtccccc gtactcacag tcgaggagat gacaaatagc      720
cgctttccaa tccccttga gaaactgttc acaggacctt cctcggcatt cgtggttcag      780
ccacagaacg gacgctgcac aactgacggc gtgctgctcg gaaccaccca gcttagccct      840
gttaatatct gtacgtttag gggcgacgta actcacataa ctggctcacg gaactatacc      900
atgaatctgg catcacagaa ttggaatgac tacgacccaa ccgaagagat tccgcacct      960
```

```
cttggaaccc ccgactttgt gggaaaaata cagggcgtcc tgacacaaac caccagaacc      1020
gatggctcca cacggggaca caaggcaacc gtctacactg gctctgccga ttttgccccg      1080
aaactgggta gagtgcagtt tgagaccgac actgaccggg actttgaagc caatcagaat      1140
actaagttca cacctgtagg agtgattcag gacgggggca ccactcaccg gaacgagccg      1200
caacaatggg tcctgccctc ttatagcggg aggaatactc ataatgtgca tttggctcct      1260
gcagtggctc ccacgtttcc cggggaacaa ctgctctttt ttcgttcaac catgcctgga      1320
tgctccggat atcccaatat ggatctcgat tgcctgctcc acaggaatg ggtgcagtat      1380 ttttatcaag aggccgcacc agcccaatcc gacgtcgcac ttctgcggtt cgtgaatcca      1440
gacacaggcc gcgtgttgtt tgagtgcaaa ttgcacaaat caggatacgt tacagtggct      1500
catactggac agcatgacct ggtgatccca cccaacggga tttaggtt cgactcctgg        1560 gtgaatcagt tttatacatt agcccccatg gggaatggga ctggcagacg cagggctgtc      1620
tga                                                                   1623
```

<210> SEQ ID NO 11
<211> LENGTH: 540
<212> TYPE: PRT
<213> ORGANISM: Norovirus

<400> SEQUENCE: 11

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
```

```
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 12
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_P80S

<400> SEQUENCE: 12

```
atgaagatgg ctagctcaga cgccaatcca agcgacggta gcgctgccaa cctcgtgccc     60
gaggtcaaca acgaagttat ggcccttgag cccgtggttg gagctgctat agctgctcct    120
gttgctgggc agcagaacgt gatagaccca tggatacgta acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
```

-continued

| | |
|---|---|
| tttgctgctg tcccacccaa ctttccaact gagggcctga gcccaagcca ggttacaatg | 420 |
| tttccacaca tgatagttga tgtcagacag ctggagccag tccttatacc cctgcccgat | 480 |
| gtccgaaaca acttctacca ctataatcag agcaacgaca gcacaatcaa gctcatcgct | 540 |
| atgctctaca caccactgag agccaacaac gcaggagatg acgtgtttac agtgtcatgt | 600 |
| agagtcctca caagaccaag ccctgatttt gatttcatct tcctcgtgcc gccaactgtt | 660 |
| gagagcagaa ctaagccctt ttctgttccc gtgctgacag ttgaggaaat gacaaattct | 720 |
| agatttccaa tcccccttga aaagctgttt acgggaccaa gctctgcctt cgtggtgcag | 780 |
| ccacagaatg gtcgatgtac aacagacggc gtcctgctcg gtacaacaca gctcagccct | 840 |
| gttaacatat gcacttttag gggcgatgtt acacatatca ctggttctca aactatact | 900 |
| atgaacctgg ccagccagaa ctggacaac tacgacccaa cagaggagat ccctgctcca | 960 |
| cttgggacac ccgactttgt tggaaagatc cagggcatgc tgacacagac gacaaagaca | 1020 |
| gatggttcaa caagaggtca caaagctact gtttacaccg gctctgccga tttcgcacca | 1080 |
| aaactcggta gagtgcagtt tcagacagat acagatcacg actttgaagc caaccagaac | 1140 |
| actaagtta caccagtcgg agttatccag gacggcaaca caacacacag aaacgagcca | 1200 |
| cagcaatggg tccttccaag ctatagcggc cggaacacac acaacgttca ccttgctccc | 1260 |
| gccgttgctc aacatttcc cggggagcag cttctttct tccgctctac aatgcccggg | 1320 |
| tgctctggat acccaaatat ggatctggac tgcctcctgc cgcaagaatg ggtgcagtat | 1380 |
| ttttaccaag aggcagctcc agctcagtct gatgttgccc tgctccggtt tgtgaacccc | 1440 |
| gatactggcc gggtccttt tgagtgcaag ctccataaga gcggatatgt gacagtcgct | 1500 |
| catactggcc agcacgacct cgttatccct cctaacggtt acttccgatt tgatagctgg | 1560 |
| gttaaccagt ttacacact tgcccctatg ggcaacggta caggccgcag agagccgtg | 1620 |
| tag | 1623 |

<210> SEQ ID NO 13
<211> LENGTH: 540
<212> TYPE: PRT
<213> ORGANISM: Norovirus

<400> SEQUENCE: 13

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140
```

-continued

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
            165                 170                 175

Lys Leu Ile Ala Met Leu Tyr Thr Pro Leu Arg Ala Asn Asn Ala Gly
        180                 185                 190

Asp Asp Val Phe Thr Val Ser Cys Arg Val Leu Thr Arg Pro Ser Pro
    195                 200                 205

Asp Phe Asp Phe Ile Phe Leu Val Pro Thr Val Glu Ser Arg Thr
210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
            245                 250                 255

Phe Val Val Gln Pro Gln Asn Gly Arg Cys Thr Thr Asp Gly Val Leu
        260                 265                 270

Leu Gly Thr Thr Gln Leu Ser Pro Val Asn Ile Cys Thr Phe Arg Gly
    275                 280                 285

Asp Val Thr His Ile Thr Gly Ser His Asn Tyr Thr Met Asn Leu Ala
290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
            325                 330                 335

Thr Thr Lys Thr Asp Gly Ser Thr Arg Gly His Lys Ala Thr Val Tyr
        340                 345                 350

Thr Gly Ser Ala Asp Phe Ala Pro Lys Leu Gly Arg Val Gln Phe Gln
    355                 360                 365

Thr Asp Thr Asp His Asp Phe Glu Ala Asn Gln Asn Thr Lys Phe Thr
370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
            405                 410                 415

His Leu Ala Pro Ala Val Ala Pro Thr Phe Pro Gly Glu Gln Leu Leu
        420                 425                 430

Phe Phe Arg Ser Thr Met Pro Gly Cys Ser Gly Tyr Pro Asn Met Asp
    435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
        500                 505                 510

Gly Tyr Phe Arg Phe Asp Ser Trp Val Asn Gln Phe Tyr Thr Leu Ala
    515                 520                 525

Pro Met Gly Asn Gly Thr Gly Arg Arg Ala Val
530                 535                 540

<210> SEQ ID NO 14
<211> LENGTH: 1623
<212> TYPE: DNA

<213> ORGANISM: Artificial Sequence
<220> FEATURE:
<223> OTHER INFORMATION: Synthetic sequence, nucleic acid sequence of Hu cod VP1 S(GII.4/2012_P80S) plus sign P(GII.4/2015)

<400> SEQUENCE: 14

```
atgaaaatgg cctcgagtga c

```
Asp Pro Trp Ile Arg Asn Asn Phe Val Gln Ala Pro Gly Gly Glu Phe
 50                  55                  60

Thr Val Ser Pro Arg Asn Ala Pro Gly Glu Ile Leu Trp Ser Ala Ser
 65                  70                  75                  80

Leu Gly Pro Asp Leu Asn Pro Tyr Leu Ser His Leu Ala Arg Met Tyr
                 85                  90                  95

Asn Gly Tyr Ala Gly Gly Phe Glu Val Gln Val Ile Leu Ala Gly Asn
                100                 105                 110

Ala Phe Thr Ala Gly Lys Val Ile Phe Ala Ala Val Pro Pro Asn Phe
            115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
    195                 200                 205

Asp Phe Asp Phe Ile Phe Leu Val Pro Pro Thr Val Glu Ser Arg Thr
210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
    275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
    355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
    435                 440                 445

Leu Asp Cys Leu Leu Pro Gln Glu Trp Val Gln Tyr Phe Tyr Gln Glu
450                 455                 460
```

-continued

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 16
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_P80S)  plus sign P(GII.4/2015_M333V)

<400> SEQUENCE: 16
atgaaaatgg cctcgagtga cgctaaccct agtgacggca gcgccgccaa tcttgtgcct     60
gaggttaata atgaggtgat ggccctggag cctgtggtgg gcgcagccat agcagcgccc    120
gtggccggtc agcagaatgt gattgacccg tggatacgca acaattttgt ccaagcccct    180
ggtggggagt tcaccgttag cccgagaaat gcgccaggag aaatcctgtg gtcggccagc    240
ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag ggcgatgtt acacatatca ctggttctca caactatact     900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tcagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttctttttct tccgctctac aatgcccggg  1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag gagagccgtg   1620
``` tag                                                                1623

<210> SEQ ID NO 17
<211> LENGTH: 540
<212> TYPE: PRT
<213> ORGANISM: Norovirus

<400> SEQUENCE: 17

| Met | Lys | Met | Ala | Ser | Ser | Asp | Ala | Asn | Pro | Ser | Asp | Gly | Ser | Ala | Ala |
|---|---|---|---|---|---|---|---|---|---|---|---|---|---|---|---|
| 1 | | | | 5 | | | | | 10 | | | | | 15 | |

| Asn | Leu | Val | Pro | Glu | Val | Asn | Asn | Glu | Val | Met | Ala | Leu | Glu | Pro | Val |
|---|---|---|---|---|---|---|---|---|---|---|---|---|---|---|---|
| | | | 20 | | | | | 25 | | | | | 30 | | |

| Val | Gly | Ala | Ala | Ile | Ala | Ala | Pro | Val | Ala | Gly | Gln | Gln | Asn | Val | Ile |
|---|---|---|---|---|---|---|---|---|---|---|---|---|---|---|---|
| | | 35 | | | | | 40 | | | | | 45 | | | |

| Asp | Pro | Trp | Ile | Arg | Asn | Asn | Phe | Val | Gln | Ala | Pro | Gly | Gly | Glu | Phe |
|---|---|---|---|---|---|---|---|---|---|---|---|---|---|---|---|
| | 50 | | | | | 55 | | | | | 60 | | | | |

| Thr | Val | Ser | Pro | Arg | Asn | Ala | Pro | Gly | Glu | Ile | Leu | Trp | Ser | Ala | Ser |
|---|---|---|---|---|---|---|---|---|---|---|---|---|---|---|---|
| 65 | | | | | 70 | | | | | 75 | | | | | 80 |

| Leu | Gly | Pro | Asp | Leu | Asn | Pro | Tyr | Leu | Ser | His | Leu | Ala | Arg | Met | Tyr |
|---|---|---|---|---|---|---|---|---|---|---|---|---|---|---|---|
| | | | | 85 | | | | | 90 | | | | | 95 | |

| Asn | Gly | Tyr | Ala | Gly | Gly | Phe | Glu | Val | Gln | Val | Ile | Leu | Ala | Gly | Asn |
|---|---|---|---|---|---|---|---|---|---|---|---|---|---|---|---|
| | | | | 100 | | | | | 105 | | | | | 110 | |

| Ala | Phe | Thr | Ala | Gly | Lys | Val | Ile | Phe | Ala | Ala | Val | Pro | Pro | Asn | Phe |
|---|---|---|---|---|---|---|---|---|---|---|---|---|---|---|---|
| | | | 115 | | | | | 120 | | | | | 125 | | |

| Pro | Thr | Glu | Gly | Leu | Ser | Pro | Ser | Gln | Val | Thr | Met | Phe | Pro | His | Ile |
|---|---|---|---|---|---|---|---|---|---|---|---|---|---|---|---|
| | | 130 | | | | | 135 | | | | | 140 | | | |

| Val | Val | Asp | Val | Arg | Gln | Leu | Glu | Pro | Val | Leu | Ile | Pro | Leu | Pro | Asp |
|---|---|---|---|---|---|---|---|---|---|---|---|---|---|---|---|
| 145 | | | | | 150 | | | | | 155 | | | | | 160 |

| Val | Arg | Asn | Asn | Phe | Tyr | His | Tyr | Asn | Gln | Ser | Asn | Asp | Pro | Thr | Ile |
|---|---|---|---|---|---|---|---|---|---|---|---|---|---|---|---|
| | | | | 165 | | | | | 170 | | | | | 175 | |

| Lys | Leu | Ile | Ala | Met | Leu | Tyr | Thr | Pro | Leu | Arg | Ala | Asn | Asn | Ala | Gly |
|---|---|---|---|---|---|---|---|---|---|---|---|---|---|---|---|
| | | | 180 | | | | | 185 | | | | | 190 | | |

| Asp | Asp | Val | Phe | Thr | Val | Ser | Cys | Arg | Val | Leu | Thr | Arg | Pro | Ser | Pro |
|---|---|---|---|---|---|---|---|---|---|---|---|---|---|---|---|
| | | 195 | | | | | 200 | | | | | 205 | | | |

| Asp | Phe | Asp | Phe | Ile | Phe | Leu | Val | Pro | Pro | Thr | Val | Glu | Ser | Arg | Thr |
|---|---|---|---|---|---|---|---|---|---|---|---|---|---|---|---|
| | 210 | | | | | 215 | | | | | 220 | | | | |

| Lys | Pro | Phe | Ser | Val | Pro | Val | Leu | Thr | Val | Glu | Glu | Met | Thr | Asn | Ser |
|---|---|---|---|---|---|---|---|---|---|---|---|---|---|---|---|
| 225 | | | | | 230 | | | | | 235 | | | | | 240 |

| Arg | Phe | Pro | Ile | Pro | Leu | Glu | Lys | Leu | Phe | Thr | Gly | Pro | Ser | Ser | Ala |
|---|---|---|---|---|---|---|---|---|---|---|---|---|---|---|---|
| | | | | 245 | | | | | 250 | | | | | 255 | |

| Phe | Val | Val | Gln | Pro | Gln | Asn | Gly | Arg | Cys | Thr | Thr | Asp | Gly | Val | Leu |
|---|---|---|---|---|---|---|---|---|---|---|---|---|---|---|---|
| | | | 260 | | | | | 265 | | | | | 270 | | |

| Leu | Gly | Thr | Thr | Gln | Leu | Ser | Pro | Val | Asn | Ile | Cys | Thr | Phe | Arg | Gly |
|---|---|---|---|---|---|---|---|---|---|---|---|---|---|---|---|
| | | 275 | | | | | 280 | | | | | 285 | | | |

| Asp | Val | Thr | His | Ile | Thr | Gly | Ser | His | Asn | Tyr | Thr | Met | Asn | Leu | Ala |
|---|---|---|---|---|---|---|---|---|---|---|---|---|---|---|---|
| | 290 | | | | | 295 | | | | | 300 | | | | |

| Ser | Gln | Asn | Trp | Asn | Asn | Tyr | Asp | Pro | Thr | Glu | Glu | Ile | Pro | Ala | Pro |
|---|---|---|---|---|---|---|---|---|---|---|---|---|---|---|---|
| 305 | | | | | 310 | | | | | 315 | | | | | 320 |

| Leu | Gly | Thr | Pro | Asp | Phe | Val | Gly | Lys | Ile | Gln | Gly | Val | Leu | Thr | Gln |
|---|---|---|---|---|---|---|---|---|---|---|---|---|---|---|---|
| | | | | 325 | | | | | 330 | | | | | 335 | |

| Thr | Thr | Lys | Thr | Asp | Gly | Ser | Thr | Arg | Gly | His | Lys | Ala | Thr | Val | Tyr |
|---|---|---|---|---|---|---|---|---|---|---|---|---|---|---|---|
| | | | 340 | | | | | 345 | | | | | 350 | | |

| Thr | Gly | Ser | Ala | Asp | Phe | Ala | Pro | Lys | Leu | Gly | Arg | Val | Gln | Phe | Gln |
|---|---|---|---|---|---|---|---|---|---|---|---|---|---|---|---|
| | | 355 | | | | | 360 | | | | | 365 | | | |

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
    530                 535                 540

<210> SEQ ID NO 18
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_P80S) plus sign P(GII.4/2015_Q368E)

<400> SEQUENCE: 18
atgaaaatgg cctcgagtga cgctaaccct agtgacggca gcgccgccaa tcttgtgcct      60
gaggttaata atgaggtgat ggccctggag cctgtggtgg cgcagccat agcagcgccc     120 gtggccggtc agcagaatgt gattgacccg tggatacgac acaattttgt ccaagcccct    180
ggtggggagt tcaccgttag cccgagaaat gcgccaggag aaatcctgtg gtcggccagc    240
ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagcagaa ctaagcccct ttctgttccc gtgctgacag ttgaggaaat gacaaattct    720
agatttccaa tccccttgaa aagctgtttt acgggaccaa gctctgcctt cgtggtgcag    780
ccacagaatg tcgatgtac aacagacggc gtcctgctcg gtacaacaca gctcagccct    840
gttaacatat gcactttag gggcgatgtt acacatatca ctggttctca aactatact     900 atgaacctgg ccagccagaa ctggaacaac tacgacccaa cagaggagat ccctgctcca    960
cttgggacac ccgactttgt tggaaagatc cagggcatgc tgacacagac gacaaagaca   1020

```
gatggttcaa caagaggtca caaagctact gtttacaccg gctctgccga tttcgcacca    1080
aaactcggta gagtgcagtt tgagacagat acagatcacg actttgaagc caaccagaac    1140
actaagttta caccagtcgg agttatccag gacggcaaca caacacacag aaacgagcca    1200
cagcaatggg tccttccaag ctatagcggc cggaacacac acaacgttca ccttgctccc    1260
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag agagccgtg    1620 tag                                                                  1623
```

<210> SEQ ID NO 19
<211> LENGTH: 540
<212> TYPE: PRT
<213> ORGANISM: Norovirus

<400> SEQUENCE: 19

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
```

260                 265                 270
Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
            290                 295                 300

Ser Gln Asn Trp Asn Asn Tyr Asp Pro Thr Glu Ile Pro Ala Pro
305                 310                 315                 320

Leu Gly Thr Pro Asp Phe Val Gly Lys Ile Gln Gly Met Leu Thr Gln
            325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
            355                 360                 365

Thr Asp Thr Asp His Asp Phe Glu Ala Asn Gln Asn Thr Lys Phe Thr
            370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
            405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
            530                 535                 540

<210> SEQ ID NO 20
<211> LENGTH: 1623
<212> TYPE: DNA
<213> ORGANISM: Norovirus

<400> SEQUENCE: 20
atgaaaatgg cctcgagtga cgctaaccct agtgacggca gcgccgccaa tcttgtgcct    60
gaggttaata atgaggtgat ggccctggag cctgtggtgg gcgcagccat agcagcgccc   120
gtggccggtc agcagaatgt gattgacccg tggatacgca acaattttgt ccaagccccg   180
ggtggggagt tcaccgttag cccgagaaat gcgccaggag aaatcctgtg gtcggccagc   240
ttgggacccg atctgaaccc ctatttgtca catctcgctc ggatgtacaa cgggtatgcc   300
ggcggatttg aagtgcaggt gattctggct gggaacgcgt tcactgctgg caaagtgatc   360
tttgcagcgg tgcctcccaa cttccccact gaaggactgt ctccaagcca ggtcacaatg   420
tttccacaca cgtggtgga cgtacggcag ctagagcctg tcctgattcc cctccctgat   480
gtacgcaata atttctacca ctacaatcaa tccaatgatc cgaccattaa actcatcgcg   540

```
atgttgtaca cccctctgcg cgctaacaat gctggagacg acgtattcac cgtgtcatgc      600
agagtgctca ccagaccttc accagacttt gactttatct tcttagtgcc ccccactgtt      660
gagagcagaa ctaagccctt ttctgttccc gtgctgacag ttgaggaaat gacaaattct      720
agatttccaa tcccccttga aaagctgttt acgggaccaa gctctgcctt cgtggtgcag      780
ccacagaatg gtcgatgtac aacagacggc gtcctgctcg gtacaacaca gctcagccct      840
gttaacatat gcactttag gggcgatgtt acacatatca ctggttctca caactatact      900
atgaacctgg ccagccagaa ctggaacaac tacgacccaa cagaggagat ccctgctcca      960
cttgggacac ccgactttgt tggaaagatc cagggcgtgc tgacacagac gacaaagaca     1020
gatggttcaa caagaggtca caaagctact gtttacaccg gctctgccga tttcgcacca     1080
aaactcggta gagtgcagtt tgagacagat acagatcacg actttgaagc caaccagaac     1140
actaagttta caccagtcgg agttatccag gacggcaaca caacacacag aaacgagcca     1200
cagcaatggg tccttccaag ctatagcggc cggaacacac acaacgttca ccttgctccc     1260
gccgttgctc aacatttcc cggggagcag cttctttct ccgctctac aatgcccggg     1320 tgctctggat acccaaatat ggatctggac tgcctcctgc cgcaagaatg ggtgcagtat     1380 tttaccaag aggcagctcc agctcagtct gatgttgccc tgctccggtt tgtgaacccc     1440
gatactggcc gggtcctttt tgagtgcaag ctccataaga gcggatatgt gacagtcgct     1500
catactggcc agcacgacct cgttatccct cctaacggtt acttccgatt tgatagctgg     1560
gttaaccagt tttacacact tgcccctatg ggcaacggta caggccgcag agagccgtg      1620 tag                                                                   1623
```

<210> SEQ ID NO 21
<211> LENGTH: 540
<212> TYPE: PRT
<213> ORGANISM: Norovirus

<400> SEQUENCE: 21

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175
```

```
Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 22
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
    cod VP1 S(GII.4/2012_A39V plus sign P80S) plus sign
    P(GII.4/2015_M333V)

<400> SEQUENCE: 22

```
atgaaaatgg cctcgagtga cgctaaccct agtgacggca gcgccgccaa tcttgtgcct      60
gaggttaata atgaggtgat ggccctggag cctgtggtgg gcgcagccat agcagtcccc     120
gtggccggtc agcagaatgt gattgacccg tggatacgca acaattttgt ccaagcccct     180
ggtggggagt tcaccgttag cccgagaaat gcgccaggag aaatcctgtg gtcggccagc     240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgg tgcctcccaa cttccccact gaaggactgt ctccaagcca ggtcacaatg     420
tttccacaca tcgtggtgga cgtacggcag ctagagcctg tcctgattcc cctccctgat     480
gtacgcaata atttctacca ctacaatcaa tccaatgatc cgaccattaa actcatcgcg     540
atgttgtaca cccctctgcg cgctaacaat gctggagacg acgtattcac cgtgtcatgc     600
agagtgctca ccagaccttc accagacttt gactttatct tcttagtgcc ccccactgtt     660
gagagcagaa ctaagccctt ttctgttccc gtgctgacag ttgaggaaat gacaaattct     720
agatttccaa tccccttgaa aaagctgttt acgggaccaa gctctgcctt cgtggtgcag     780
ccacagaatg gtcgatgtac aacagacggc gtcctgctcg gtacaacaca gctcagccct     840
gttaacatat gcacttttag gggcgatgtt acacatatca ctggttctca aactatact      900
atgaacctgg ccagccagaa ctggaacaac tacgacccaa cagaggagat ccctgctcca     960
cttgggacac ccgactttgt tggaaagatc cagggcgtgc tgacacagac gacaaagaca    1020
gatggttcaa caagaggtca caaagctact gtttacaccg gctctgccga tttcgcacca    1080
aaactcggta gagtgcagtt tcagacagat acagatcacg actttgaagc caaccagaac    1140
actaagttta caccagtcgg agttatccag gacggcaaca aacacacag aaacgagcca    1200
cagcaatggg tccttccaag ctatagcggc cggaacacac acaacgttca ccttgctccc    1260
gccgttgctc aacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgccctatg ggcaacggta caggccgcag agagccgtg     1620
tag                                                                 1623
```

<210> SEQ ID NO 23
<211> LENGTH: 540
<212> TYPE: PRT
<213> ORGANISM: Norovirus

<400> SEQUENCE: 23

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
```

```
                65                  70                  75                  80
Leu Gly Pro Asp Leu Asn Pro Tyr Leu Ser His Leu Ala Arg Met Tyr
                    85                  90                  95

Asn Gly Tyr Ala Gly Gly Phe Glu Val Gln Val Ile Leu Ala Gly Asn
                100                 105                 110

Ala Phe Thr Ala Gly Lys Val Ile Phe Ala Ala Val Pro Asn Phe
                115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
                195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
            290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
                340                 345                 350

Thr Gly Ser Ala Asp Phe Ala Pro Lys Leu Gly Arg Val Gln Phe Gln
            355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495
```

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 24
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_A39V+P80S) plus sign P(GII.4/2015_Q368E)

<400> SEQUENCE: 24

```
atgaaaatgg cctcgagtga cgctaaccct agtgacggca gcgccgccaa tcttgtgcct    60
gaggttaata atgaggtgat ggccctggag cctgtggtgg cgcagccat agcagtcccc    120 gtggccggtc agcagaatgt gattgacccg tggatacgca caatttgt ccaagcccct    180 ggtggggagt tcaccgttag cccgagaaat gcgccaggag aaatcctgtg gtcgccagc    240 ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagcagaa ctaagccctt ttctgttccc gtgctgacag ttgaggaaat gacaaattct    720
agatttccaa tccccctgaa aaagctgttt acgggaccaa gctctgcctt cgtggtgcag    780
ccacagaatg tcgatgtac aacagacggc gtcctgctcg gtacaacaca gctcagccct    840
gttaacatat gcacttttag gggcgatgtt acacatatca ctggttctca aactatact    900 atgaacctgg ccagccagaa ctggaacaac tacgacccaa cagaggagat ccctgctcca    960
cttgggacac ccgactttgt ggaaagatc cagggcatgc tgacacagac gacaaagaca   1020
gatggttcaa caagaggtca caaagctact gtttacaccg gctctgccga tttcgcacca   1080
aaactcggta gagtgcagtt tgagacagat acagatacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttctttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag agagccgtg   1620 tag                                                                 1623
```

<210> SEQ ID NO 25

<211> LENGTH: 540
<212> TYPE: PRT
<213> ORGANISM: Norovirus

<400> SEQUENCE: 25

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
```

```
                385                 390                 395                 400
        Gln Gln Trp Val Leu Pro Ser Tyr Ser Gly Arg Asn Thr His Asn Val
                        405                 410                 415

His Leu Ala Pro Ala Val Ala Pro Thr Phe Pro Gly Glu Gln Leu Leu
                        420                 425                 430

Phe Phe Arg Ser Thr Met Pro Gly Cys Ser Gly Tyr Pro Asn Met Asp
                        435                 440                 445

Leu Asp Cys Leu Leu Pro Gln Glu Trp Val Gln Tyr Phe Tyr Gln Glu
                        450                 455                 460

Ala Ala Pro Ala Gln Ser Asp Val Ala Leu Leu Arg Phe Val Asn Pro
        465                 470                 475                 480

Asp Thr Gly Arg Val Leu Phe Glu Cys Lys Leu His Lys Ser Gly Tyr
                        485                 490                 495

Val Thr Val Ala His Thr Gly Gln His Asp Leu Val Ile Pro Pro Asn
                        500                 505                 510

Gly Tyr Phe Arg Phe Asp Ser Trp Val Asn Gln Phe Tyr Thr Leu Ala
                        515                 520                 525

Pro Met Gly Asn Gly Thr Gly Arg Arg Arg Ala Val
                        530                 535                 540

<210> SEQ ID NO 26
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_A39V+P80S) + P(GII.4/2015_M333A+Q368E)

<400> SEQUENCE: 26
atgaaaatgg cctcgagtga cgctaaccct agtgacggca cgccgccaa tcttgtgcct      60 gaggttaata atgaggtgat ggccctggag cctgtggtgg gcgcagccat agcagtcccc     120
gtggccggtc agcagaatgt gattgacccg tggatacgca caattttgt ccaagccct     180 ggtggggagt tcaccgttag cccgagaaat gcgccaggag aaatcctgtg gtcggccagc     240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgt gcctcccaa cttcccact gaaggactgt ctccaagcca ggtcacaatg     420
tttccacaca tcgtggtgga cgtacggcag ctagagcctg tcctgattcc cctccctgat     480
gtacgcaata atttctacca ctacaatcaa tccaatgatc cgaccattaa actcatcgcg     540
atgttgtaca ccctctgcg cgctaacaat gctggagacg acgtattcac cgtgtcatgc     600
agagtgctca ccagaccttc accagactt gactttatct tcttagtgcc ccccactgtt     660
gagagcagaa ctaagccctt ttctgttccc gtgctgacag ttgaggaaat gacaaattct     720
agatttccaa tccccttga aaagctgttt acgggaccaa gctctgcctt cgtggtgcag     780
ccacagaatg gtcgatgtac aacagacggc gtcctgctcg gtacaacaca gctcagccct     840
gttaacatat gcactttag ggcgatgtt acacatatca ctggttctca aactatact     900 atgaacctgg ccagccagaa ctggaacaac tacgacccaa cagaggagat ccctgctcca     960
cttgggacac ccgactttgt tggaaagatc cagggcgtgc tgacacagac gacaaagaca    1020
gatggttcaa caagaggtca caaagctact gtttacaccg gctctgccga ttcgcacca    1080 aaactcggta gtgcagtt tgagacagat acagatcacg actttgaagc caaccagaac    1140
actaagttta caccagtcgg agttatccag gacggcaaca aacacacag aaacgagcca    1200
```

```
cagcaatggg tccttccaag ctatagcggc cggaacacac acaacgttca ccttgctccc   1260
gccgttgctc caacatttcc cggggagcag cttcttttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag agagccgtg   1620 tag                                                                 1623
```

<210> SEQ ID NO 27
<211> LENGTH: 540
<212> TYPE: PRT
<213> ORGANISM: Norovirus

<400> SEQUENCE: 27

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285
```

Asp Val Thr His Ile Thr Gly Ser His Asn Tyr Thr Met Asn Leu Ala
            290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
            355                 360                 365

Thr Asp Thr Asp His Asp Phe Glu Ala Asn Gln Asn Thr Lys Phe Thr
            370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
530                 535                 540

<210> SEQ ID NO 28
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_R53Iplus sign P80S) plus sign P(GII.4/2015_M333V)

<400> SEQUENCE: 28

```
atgaaaatgg cctcgagtga cgctaaccct agtgacggca gcgccgccaa tcttgtgcct      60
gaggttaata atgaggtgat ggccctggag cctgtggtgg gcgcagccat agcagcgccc     120
gtggccggtc agcagaatgt gattgacccg tggataatca acaattttgt ccaagcccct     180
ggtggggagt tcaccgttag cccgagaaat gcgccaggag aaatcctgtg gtcggccagc     240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgg tgcctcccaa cttccccact gaaggactgt ctccaagcca ggtcacaatg     420
tttccacaca tcgtggtgga cgtacggcag ctagagcctg tcctgattcc cctccctgat     480
gtacgcaata atttctacca ctacaatcaa tccaatgatc cgaccattaa actcatcgcg     540
atgttgtaca cccctctgcg cgctaacaat gctggagacg acgtattcac cgtgtcatgc     600
```

-continued

```
agagtgctca ccagaccttc accagacttt gactttatct tcttagtgcc ccccactgtt      660
gagagcagaa ctaagccctt ttctgttccc gtgctgacag ttgaggaaat gacaaattct      720
agatttccaa tcccccttga aaagctgttt acgggaccaa gctctgcctt cgtggtgcag      780
ccacagaatg gtcgatgtac aacagacggc gtcctgctcg gtacaacaca gctcagccct      840
gttaacatat gcacttttag gggcgatgtt acacatatca ctggttctca caactatact      900
atgaacctgg ccagccagaa ctggaacaac tacgacccaa cagaggagat ccctgctcca      960
cttgggacac ccgactttgt tggaaagatc cagggcgtgc tgacacagac gacaaagaca     1020
gatggttcaa caagaggtca caaagctact gtttacaccg gctctgccga tttcgcacca     1080
aaactcggta gagtgcagtt tcagacagat acagatcacg actttgaagc caaccagaac     1140
actaagttta caccagtcgg agttatccag gacggcaaca caacacacag aaacgagcca     1200
cagcaatggg tccttccaag ctatagcggc cggaacacac acaacgttca ccttgctccc     1260
gccgttgctc aacatttcc cggggagcag cttcttttct tccgctctac aatgcccggg     1320
tgctctggat acccaaatat ggatctggac tgcctcctgc cgcaagaatg ggtgcagtat     1380
ttttaccaag aggcagctcc agctcagtct gatgttgccc tgctccggtt tgtgaacccc     1440
gatactggcc gggtcctttt tgagtgcaag ctccataaga gcggatatgt gacagtcgct     1500
catactggcc agcacgacct cgttatccct cctaacggtt acttccgatt tgatagctgg     1560
gttaaccagt tttacacact tgcccctatg ggcaacggta caggccgcag agagccgtg     1620
tag                                                                   1623
```

<210> SEQ ID NO 29
<211> LENGTH: 540
<212> TYPE: PRT
<213> ORGANISM: Norovirus

<400> SEQUENCE: 29

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
```

```
            180                 185                 190
Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
            210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
            245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
            290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
            325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
            355                 360                 365

Thr Asp Thr Asp His Asp Phe Glu Ala Asn Gln Asn Thr Lys Phe Thr
            370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
            405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
            450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
530                 535                 540

<210> SEQ ID NO 30
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_R53I plus sign P80S) plus sign
      P(GII.4/2015_Q368E)

<400> SEQUENCE: 30
```

```
atgaaaatgg cctcgagtga cgctaaccct agtgacggca gcgccgccaa tcttgtgcct    60
gaggttaata atgaggtgat ggccctggag cctgtggtgg gcgcagccat agcagcgccc   120
gtggccggtc agcagaatgt gattgacccg tggataatca acaattttgt ccaagcccct   180
ggtgggagt tcaccgttag cccgagaaat gcgccaggaa aatcctgtg gtcggccagc    240
ttgggacccg atctgaaccc ctatttgtca catctcgctc ggatgtacaa cgggtatgcc   300
ggcggatttg aagtgcaggt gattctggct gggaacgcgt tcactgctgg caaagtgatc   360
tttgcagcgg tgcctcccaa cttccccact gaaggactgt ctccaagcca ggtcacaatg   420
tttccacaca tcgtggtgga cgtacggcag ctagagcctg tcctgattcc cctccctgat   480
gtacgcaata atttctacca ctacaatcaa tccaatgatc cgaccattaa actcatcgcg   540
atgttgtaca cccctctgcg cgctaacaat gctggagacg acgtattcac cgtgtcatgc   600
agagtgctca ccagaccttc accagacttt gactttatct tcttagtgcc ccccactgtt   660
gagagcagaa ctaagccctt ttctgttccc gtgctgacag ttgaggaaat gacaaattct   720
agatttccaa tccccttga aaagctgttt acgggaccaa gctctgcctt cgtggtgcag   780
ccacagaatg tcgatgtac aacagacggc gtcctgctcg gtacaacaca gctcagccct   840
gttaacatat gcacttttag gggcgatgtt acacatatca ctggttctca aactatact    900
atgaacctgg ccagccagaa ctggaacaac tacgacccaa cagaggagat ccctgctcca   960
cttgggacac ccgactttgt ggaaagatc cagggcatgc tgacacagac gacaaagaca  1020
gatggttcaa caagaggtca caaagctact gtttacaccg gctctgccga tttcgcacca  1080
aaactcggta gagtgcagtt tgagacagat acagatcacg actttgaagc caaccagaac  1140
actaagttta caccagtcgg agttatccag gacggcaaca caacacacag aaacgagcca  1200
cagcaatggg tccttccaag ctatagcggc cggaacacac acaacgttca ccttgctccc  1260
gccgttgctc caacatttcc cggggagcag cttcttttct cccgctctac aatgcccggg  1320
tgctctggat acccaaatat ggatctggac tgcctcctgc cgcaagaatg ggtgcagtat  1380
ttttaccaag aggcagctcc agctcagtct gatgttgccc tgctccggtt tgtgaacccc  1440
gatactggcc gggtcctttt tgagtgcaag ctccataaga gcggatatgt gacagtcgct  1500
catactggcc agcacgacct cgttatccct cctaacggtt acttccgatt tgatagctgg  1560
gttaaccagt tttacacact tgcccctatg ggcaacggta caggccgcag agagccgtg   1620
tag                                                                1623

<210> SEQ ID NO 31
<211> LENGTH: 540
<212> TYPE: PRT
<213> ORGANISM: Norovirus

<400> SEQUENCE: 31

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Ile Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80
```

-continued

```
Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
        210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
        290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495
```

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
        530                 535                 540

<210> SEQ ID NO 32
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_R53I plus sign P80S) plus sign
      P(GII.4/2015_M333V plus sign Q368E)

<400> SEQUENCE: 32
atgaaaatgg cctcgagtga cgctaaccct agtgacggca cgccgccaa tcttgtgcct      60 gaggttaata atgaggtgat ggccctggag cctgtggtgg cgcagccat agcagcgccc     120 gtggccggtc agcagaatgt gattgacccg tggataatca acaattttgt ccaagcccct    180
ggtggggagt tcaccgttag cccgagaaat gcgccaggag aaatcctgtg gtcggccagc    240
ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg tcgatgtac aacagacggc gtcctgctcg gtacaacaca gctcagccct    840
gttaacatat gcacttttag gggcgatgtt acacatatca ctggttctca aactatact    900 atgaacctgg ccagccagaa ctggaacaac tacgacccaa cagaggagat ccctgctcca    960
cttgggacac ccgactttgt ggaaagatc cagggcgtgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc aacatttcc cggggagcag cttcttttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag agagccgtg   1620 tag                                                                 1623

<210> SEQ ID NO 33

```
<211> LENGTH: 540
<212> TYPE: PRT
<213> ORGANISM: Norovirus

<400> SEQUENCE: 33

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
```

-continued

```
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 34
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 S(GII.4/2012_A39V plus sign R53I plus sign P80S) plus sign P(GII.4/2015_M333V)

<400> SEQUENCE: 34

```
atgaaaatgg cctcgagtga cgctaaccct agtgacggca gcgccgccaa tcttgtgcct     60
gaggttaata atgaggtgat ggccctggag cctgtggtgg gcgcagccat agcagtcccc    120
gtggccggtc agcagaatgt gattgacccg tggataatca acaattttgt ccaagcccct    180
ggtggggagt tcaccgttag cccgagaaat gcgccaggag aaatcctgtg gtcggccagc    240
ttgggacccg atctgaaccc ctatttgtca catctcgctc ggatgtacaa cgggtatgcc    300
ggcggatttg aagtgcaggt gattctggct gggaacgcgt tcactgctgg caaagtgatc    360
tttgcagcgg tgcctcccaa cttccccact gaaggactgt ctccaagcca ggtcacaatg    420
tttccacaca tcgtggtgga cgtacggcag ctagagcctg tcctgattcc cctccctgat    480
gtacgcaata atttctacca ctacaatcaa tccaatgatc cgaccattaa actcatcgcg    540
atgttgtaca cccctctgcg cgctaacaat gctggagacg acgtattcac cgtgtcatgc    600
agagtgctca ccagaccttc accagacttt gactttatct tcttagtgcc ccccactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tcagacagat acagatcacg actttgaagc caaccagaac   1140
```

-continued

```
actaagttta caccagtcgg agttatccag gacggcaaca caacacacag aaacgagcca    1200
cagcaatggg tccttccaag ctatagcggc cggaacacac acaacgttca ccttgctccc    1260
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag gagagccgtg    1620
tag                                                                  1623
```

<210> SEQ ID NO 35
<211> LENGTH: 541
<212> TYPE: PRT
<213> ORGANISM: Norovirus

<400> SEQUENCE: 35

```
Met Met Lys Met Ala Ser Ser Asp Ala Asn Pro Ser Asp Gly Ser Ala
1               5                   10                  15

Ala Asn Leu Val Pro Glu Val Asn Asn Glu Val Met Ala Leu Glu Pro
                20                  25                  30

Val Val Gly Ala Ala Ile Ala Val Pro Val Ala Gly Gln Gln Asn Val
            35                  40                  45

Ile Asp Pro Trp Ile Ile Asn Asn Phe Val Gln Ala Pro Gly Gly Glu
        50                  55                  60

Phe Thr Val Ser Pro Arg Asn Ala Pro Gly Glu Ile Leu Trp Ser Ala
65                  70                  75                  80

Ser Leu Gly Pro Asp Leu Asn Pro Tyr Leu Ser His Leu Ala Arg Met
                85                  90                  95

Tyr Asn Gly Tyr Ala Gly Gly Phe Glu Val Gln Val Ile Leu Ala Gly
                100                 105                 110

Asn Ala Phe Thr Ala Gly Lys Val Ile Phe Ala Ala Val Pro Pro Asn
            115                 120                 125

Phe Pro Thr Glu Gly Leu Ser Pro Ser Gln Val Thr Met Phe Pro His
        130                 135                 140

Ile Val Val Asp Val Arg Gln Leu Glu Pro Val Leu Ile Pro Leu Pro
145                 150                 155                 160

Asp Val Arg Asn Asn Phe Tyr His Tyr Asn Gln Ser Asn Asp Pro Thr
                165                 170                 175

Ile Lys Leu Ile Ala Met Leu Tyr Thr Pro Leu Arg Ala Asn Asn Ala
                180                 185                 190

Gly Asp Asp Val Phe Thr Val Ser Cys Arg Val Leu Thr Arg Pro Ser
            195                 200                 205

Pro Asp Phe Asp Phe Ile Phe Leu Val Pro Pro Thr Val Glu Ser Arg
        210                 215                 220

Thr Lys Pro Phe Ser Val Pro Val Leu Thr Val Glu Glu Met Thr Asn
225                 230                 235                 240

Ser Arg Phe Pro Ile Pro Leu Glu Lys Leu Phe Thr Gly Pro Ser Ser
                245                 250                 255

Ala Phe Val Val Gln Pro Gln Asn Gly Arg Cys Thr Thr Asp Gly Val
            260                 265                 270

Leu Leu Gly Thr Thr Gln Leu Ser Pro Val Asn Ile Cys Thr Phe Arg
        275                 280                 285
```

```
Gly Asp Val Thr His Ile Thr Gly Ser His Asn Tyr Thr Met Asn Leu
    290                 295                 300

Ala Ser Gln Asn Trp Asn Asn Tyr Asp Pro Thr Glu Glu Ile Pro Ala
305                 310                 315                 320

Pro Leu Gly Thr Pro Asp Phe Val Gly Lys Ile Gln Gly Val Leu Thr
                325                 330                 335

Gln Thr Thr Lys Thr Asp Gly Ser Thr Arg Gly His Lys Ala Thr Val
            340                 345                 350

Tyr Thr Gly Ser Ala Asp Phe Ala Pro Lys Leu Gly Arg Val Gln Phe
        355                 360                 365

Gln Thr Asp Thr Asp His Asp Phe Glu Ala Asn Gln Asn Thr Lys Phe
    370                 375                 380

Thr Pro Val Gly Val Ile Gln Asp Gly Asn Thr Thr His Arg Asn Glu
385                 390                 395                 400

Pro Gln Gln Trp Val Leu Pro Ser Tyr Ser Gly Arg Asn Thr His Asn
                405                 410                 415

Val His Leu Ala Pro Ala Val Ala Pro Thr Phe Pro Gly Glu Gln Leu
            420                 425                 430

Leu Phe Phe Arg Ser Thr Met Pro Gly Cys Ser Gly Tyr Pro Asn Met
        435                 440                 445

Asp Leu Asp Cys Leu Leu Pro Gln Glu Trp Val Gln Tyr Phe Tyr Gln
    450                 455                 460

Glu Ala Ala Pro Ala Gln Ser Asp Val Ala Leu Leu Arg Phe Val Asn
465                 470                 475                 480

Pro Asp Thr Gly Arg Val Leu Phe Glu Cys Lys Leu His Lys Ser Gly
                485                 490                 495

Tyr Val Thr Val Ala His Thr Gly Gln His Asp Leu Val Ile Pro Pro
            500                 505                 510

Asn Gly Tyr Phe Arg Phe Asp Ser Trp Val Asn Gln Phe Tyr Thr Leu
        515                 520                 525

Ala Pro Met Gly Asn Gly Thr Gly Arg Arg Arg Ala Val
    530                 535                 540

<210> SEQ ID NO 36
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_A39V plus sign R53I plus sign P80S) plus sign
      P(GII.4/2015_Q368E)

<400> SEQUENCE: 36
atgaaaatgg cctcgagtga cgctaaccct agtgacggca gcgccgccaa tcttgtgcct      60
gaggttaata atgaggtgat ggccctggag cctgtggtgg gcgcagccat agcagtcccc     120
gtggccggtc agcagaatgt gattgacccg tggataatca acaattttgt ccaagcccct     180
ggtggggagt tcaccgttag cccgagaaat gcgccaggag aaatcctgtg gtcggccagc     240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgg tgcctcccaa cttccccact gaaggactgt ctccaagcca ggtcacaatg     420
tttccacaca tcgtggtgga cgtacggcag ctagagcctg tcctgattcc cctccctgat     480
gtacgcaata atttctacca ctacaatcaa tccaatgatc cgaccattaa actcatcgcg     540
```

```
atgttgtaca cccctctgcg cgctaacaat gctggagacg acgtattcac cgtgtcatgc   600
agagtgctca ccagaccttc accagacttt gactttatct tcttagtgcc ccccactgtt   660
gagagcagaa ctaagcccct ttctgttccc gtgctgacag ttgaggaaat gacaaattct   720
agatttccaa tcccccttga aaagctgttt acgggaccaa gctctgcctt cgtggtgcag   780
ccacagaatg gtcgatgtac aacagacggc gtcctgctcg gtacaacaca gctcagccct   840
gttaacatat gcacttttag gggcgatgtt acacatatca ctggttctca caactatact   900
atgaacctgg ccagccagaa ctggaacaac tacgacccaa cagaggagat ccctgctcca   960
cttgggacac ccgactttgt tggaaagatc cagggcatgc tgacacagac gacaaagaca  1020
gatggttcaa caagaggtca caaagctact gtttacaccg gctctgccga tttcgcacca  1080
aaactcggta gagtgcagtt tgagacagat acagatcacg actttgaagc caaccagaac  1140
actaagttta caccagtcgg agttatccag gacggcaaca caacacacag aaacgagcca  1200
cagcaatggg tccttccaag ctatagcggc cggaacacac acaacgttca ccttgctccc  1260
gccgttgctc aacatttcc cggggagcag cttcttttct tccgctctac aatgcccggg  1320
tgctctggat acccaaatat ggatctggac tgcctcctgc cgcaagaatg ggtgcagtat  1380
ttttaccaag aggcagctcc agctcagtct gatgttgccc tgctccggtt tgtgaacccc  1440
gatactggcc gggtcctttt tgagtgcaag ctccataaga gcggatatgt gacagtcgct  1500
catactggcc agcacgacct cgttatccct cctaacggtt acttccgatt tgatagctgg  1560
gttaaccagt tttacacact tgcccctatg ggcaacggta caggccgcag agagccgtg   1620 tag                                                                1623

<210> SEQ ID NO 37
<211> LENGTH: 540
<212> TYPE: PRT
<213> ORGANISM: Norovirus

<400> SEQUENCE: 37

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Val Pro Val Ala Gly Gln Gln Asn Val Ile
            35                  40                  45

Asp Pro Trp Ile Ile Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Val Ile Phe Ala Ala Val Pro Pro Asn Phe
            115                 120                 125

Pro Thr Glu Gly Leu Ser Pro Ser Gln Val Thr Met Phe Pro His Ile
        130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175
```

```
Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
530                 535                 540
```

<210> SEQ ID NO 38
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 S(GII.4/2012_A39V plus sign R53I plus sign P80S) plus sign P(GII.4/2015_M333V plus sign Q368E

<400> SEQUENCE: 38

```
atgaaaatgg cctcgagtga cgctaaccct agtgacggca gcgccgccaa tcttgtgcct      60
gaggttaata atgaggtgat ggccctggag cctgtggtgg gcgcagccat agcagtcccc     120
gtggccggtc agcagaatgt gattgacccg tggataatca acaattttgt ccaagcccct     180
ggtggggagt tcaccgttag cccgagaaat gcgccaggag aaatcctgtg gtcggccagc     240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgg tgcctcccaa cttccccact gaaggactgt ctccaagcca ggtcacaatg     420
tttccacaca tcgtggtgga cgtacggcag ctagagcctg tcctgattcc cctccctgat     480
gtacgcaata atttctacca ctacaatcaa tccaatgatc cgaccattaa actcatcgcg     540
atgttgtaca cccctctgcg cgctaacaat gctggagacg acgtattcac cgtgtcatgc     600
agagtgctca ccagaccttc accagacttt gactttatct tcttagtgcc ccccactgtt     660
gagagcagaa ctaagccctt ttctgttccc gtgctgacag ttgaggaaat gacaaattct     720
agatttccaa tcccccttga aaagctgttt acgggaccaa gctctgcctt cgtggtgcag     780
ccacagaatg gtcgatgtac aacagacggc gtcctgctcg gtacaacaca gctcagccct     840
gttaacatat gcacttttag gggcgatgtt acacatatca ctggttctca aactatact      900
atgaacctgg ccagccagaa ctggaacaac tacgacccaa cagaggagat ccctgctcca     960
cttgggacac ccgactttgt tggaaagatc cagggcgtgc tgacacagac gacaaagaca    1020
gatggttcaa caagaggtca caaagctact gtttacaccg gctctgccga tttcgcacca    1080
aaactcggta gagtgcagtt tgagacagat acagatcacg actttgaagc caaccagaac    1140
actaagttta caccagtcgg agttatccag gacggcaaca acacacag aaacgagcca    1200
cagcaatggg tccttccaag ctatagcggc cggaacacac acaacgttca ccttgctccc    1260
gccgttgctc aacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag agagccgtg     1620
tag                                                                   1623
```

<210> SEQ ID NO 39
<211> LENGTH: 540
<212> TYPE: PRT
<213> ORGANISM: Norovirus

<400> SEQUENCE: 39

```
Met Lys Met Ala Ser Ser Asp Ala Asn Pro Ser Asp Gly Ser Ala Ala
 1               5                  10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
```

-continued

```
                65                  70                  75                  80
Leu Gly Pro Asp Leu Asn Pro Tyr Leu Ser His Leu Ala Arg Met Tyr
                        85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495
```

```
Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 40
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_P80S plus sign M333V

<400> SEQUENCE: 40
atgaagatgg ctagctcaga cgccaatcca agcgacggta gcgctgccaa cctcgtgccc     60
gaggtcaaca acgaagttat ggcccttgag cccgtggttg gagctgctat agctgctcct    120
gttgctgggc agcagaacgt gatagaccca tggatacgta acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag ggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tcagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttcttttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag gagagccgtg   1620
tag                                                                 1623

<210> SEQ ID NO 41
```

```
<211> LENGTH: 540
<212> TYPE: PRT
<213> ORGANISM: Norovirus

<400> SEQUENCE: 41

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
```

```
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 42
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_P80S plus sign Q368E

<400> SEQUENCE: 42
atgaagatgg ctagctcaga cgccaatcca agcgacggta gcgctgccaa cctcgtgccc     60
gaggtcaaca acgaagttat ggcccttgag cccgtggttg gagctgctat agctgctcct    120
gttgctgggc agcagaacgt gatagaccca tggatacgta acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcatgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
```

```
cagcaatggg tccttccaag ctatagcggc cggaacacac acaacgttca ccttgctccc    1260
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag agagccgtg     1620 tag                                                                  1623
```

<210> SEQ ID NO 43
<211> LENGTH: 540
<212> TYPE: PRT
<213> ORGANISM: Norovirus

<400> SEQUENCE: 43

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285
```

```
Asp Val Thr His Ile Thr Gly Ser His Asn Tyr Thr Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Lys Ile Gln Gly Met Leu Thr Gln
                325                 330                 335
Thr Thr Lys Thr Asp Gly Ser Thr Arg Gly His Lys Ala Thr Val Tyr
            340                 345                 350
Thr Gly Ser Ala Asp Phe Ala Pro Lys Leu Gly Arg Val Gln Phe Glu
        355                 360                 365
Thr Asp Thr Asp His Asp Phe Glu Ala Asn Gln Asn Thr Lys Phe Thr
    370                 375                 380
Pro Val Gly Val Ile Gln Asp Gly Asn Thr Thr His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln Tyr Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Val
    530                 535                 540
```

<210> SEQ ID NO 44
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_P80S plus sign M333V plu ssign Q368E

<400> SEQUENCE: 44

```
atgaagatgg ctagctcaga cgccaatcca agcgacggta gcgctgccaa cctcgtgccc     60
gaggtcaaca acgaagttat ggcccttgag cccgtggttg gagctgctat agctgctcct    120
gttgctgggc agcagaacgt gatagaccca tggatacgta acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
```

```
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca aactatact     900 atgaacctgg ccagccagaa ctggaacaac tacgacccaa cagaggagat ccctgctcca    960
cttgggacac ccgactttgt ggaaagatc cagggcgtgc tgacacagac gacaaagaca    1020
gatggttcaa caagaggtca caaagctact gtttacaccg gctctgccga tttcgcacca    1080
aaactcggta gagtgcagtt tgagacagat acagatcacg actttgaagc caaccagaac    1140
actaagttta caccagtcgg agttatccag gacggcaaca caacacacag aaacgagcca    1200
cagcaatggg tccttccaag ctatagcggc cggaacacac acaacgttca ccttgctccc    1260
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtccttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag agagccgtg    1620 tag                                                                  1623

<210> SEQ ID NO 45
<211> LENGTH: 540
<212> TYPE: PRT
<213> ORGANISM: Norovirus

<400> SEQUENCE: 45

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190
```

```
Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 46
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_A39V plus sign P80S

<400> SEQUENCE: 46
atgaagatgg ctagctcaga cgccaatcca agcgacggta gcgctgccaa cctcgtgccc     60

```
gaggtcaaca acgaagttat ggcccttgag cccgtggttg gagctgctat agctgtgcct      120
gttgctgggc agcagaacgt gatagaccca tggatacgta acaactttgt tcaggccccc      180
ggtggagagt ttacagtcag cccaagaaac gctcctggag agatactgtg gagcgcctcc      240
ctcggccccg acctcaaccc ctatctgtca catctcgctc gcatgtataa cggctatgct      300
ggcggttttg aagttcaggt catccttgcc ggaaacgcct tcaccgctgg aagataatc       360
tttgctgctg tcccacccaa ctttccaact gagggcctga gcccaagcca ggttacaatg      420
tttccacaca tgatagttga tgtcagacag ctggagccag tccttatacc cctgcccgat      480
gtccgaaaca acttctacca ctataatcag agcaacgaca gcacaatcaa gctcatcgct      540
atgctctaca caccactgag agccaacaac gcaggagatg acgtgtttac agtgtcatgt      600
agagtcctca aagaccaag ccctgatttt gatttcatct tcctcgtgcc gccaactgtt       660
gagagcagaa ctaagccctt ttctgttccc gtgctgacag ttgaggaaat gacaaattct      720
agatttccaa tcccccttga aaagctgttt acgggaccaa gctctgcctt cgtggtgcag      780
ccacagaatg gtcgatgtac aacagacggc gtcctgctcg gtacaacaca gctcagccct      840
gttaacatat gcacttttag gggcgatgtt acacatatca ctggttctca aactatact       900
atgaacctgg ccagccagaa ctggaacaac tacgacccaa cagaggagat ccctgctcca      960
cttgggacac ccgactttgt tggaaagatc cagggcatgc tgacacagac gacaaagaca     1020
gatggttcaa caagaggtca caagctact gtttacaccg gctctgccga tttcgcacca      1080
aaactcggta gagtgcagtt tcagacagat acagatcacg actttgaagc caaccagaac     1140
actaagttta caccagtcgg agttatccag gacggcaaca acacacag aaacgagcca       1200
cagcaatggg tccttccaag ctatagcggc cggaacacac acaacgttca ccttgctccc     1260
gccgttgctc aacatttcc cggggagcag cttcttttct tccgctctac aatgcccggg      1320
tgctctggat acccaaatat ggatctggac tgcctcctgc cgcaagaatg ggtgcagtat     1380
ttttaccaag aggcagctcc agctcagtct gatgttgccc tgctccggtt tgtgaacccc     1440
gatactggcc gggtcctttt tgagtgcaag ctccataaga gcggatatgt gacagtcgct     1500
catactggcc agcacgacct cgttatccct cctaacggtt acttccgatt tgatagctgg     1560
gttaaccagt tttacacact tgcccctatg ggcaacggta caggccgcag gagagccgtg     1620
tag                                                                   1623
```

<210> SEQ ID NO 47
<211> LENGTH: 540
<212> TYPE: PRT
<213> ORGANISM: Norovirus

<400> SEQUENCE: 47

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
```

```
            85                  90                  95
Asn Gly Tyr Ala Gly Gly Phe Glu Val Gln Val Ile Leu Ala Gly Asn
            100                 105                 110
Ala Phe Thr Ala Gly Lys Ile Ile Phe Ala Ala Val Pro Pro Asn Phe
            115                 120                 125
Pro Thr Glu Gly Leu Ser Pro Ser Gln Val Thr Met Phe Pro His Met
            130                 135                 140
Ile Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Ser Thr Ile
                    165                 170                 175
Lys Leu Ile Ala Met Leu Tyr Thr Pro Leu Arg Ala Asn Asn Ala Gly
                    180                 185                 190
Asp Asp Val Phe Thr Val Ser Cys Arg Val Leu Thr Arg Pro Ser Pro
                    195                 200                 205
Asp Phe Asp Phe Ile Phe Leu Val Pro Pro Thr Val Glu Ser Arg Thr
            210                 215                 220
Lys Pro Phe Ser Val Pro Val Leu Thr Val Glu Glu Met Thr Asn Ser
225                 230                 235                 240
Arg Phe Pro Ile Pro Leu Glu Lys Leu Phe Thr Gly Pro Ser Ser Ala
                    245                 250                 255
Phe Val Val Gln Pro Gln Asn Gly Arg Cys Thr Thr Asp Gly Val Leu
                    260                 265                 270
Leu Gly Thr Thr Gln Leu Ser Pro Val Asn Ile Cys Thr Phe Arg Gly
                    275                 280                 285
Asp Val Thr His Ile Thr Gly Ser His Asn Tyr Thr Met Asn Leu Ala
            290                 295                 300
Ser Gln Asn Trp Asn Asn Tyr Asp Pro Thr Glu Ile Pro Ala Pro
305                 310                 315                 320
Leu Gly Thr Pro Asp Phe Val Gly Lys Ile Gln Gly Met Leu Thr Gln
                    325                 330                 335
Thr Thr Lys Thr Asp Gly Ser Thr Arg Gly His Lys Ala Thr Val Tyr
            340                 345                 350
Thr Gly Ser Ala Asp Phe Ala Pro Lys Leu Gly Arg Val Gln Phe Gln
            355                 360                 365
Thr Asp Thr Asp His Asp Phe Glu Ala Asn Gln Asn Thr Lys Phe Thr
            370                 375                 380
Pro Val Gly Val Ile Gln Asp Gly Asn Thr Thr His Arg Asn Glu Pro
385                 390                 395                 400
Gln Gln Trp Val Leu Pro Ser Tyr Ser Gly Arg Asn Thr His Asn Val
                    405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
            435                 440                 445
Leu Asp Cys Leu Leu Pro Gln Glu Trp Val Gln Tyr Phe Tyr Gln Glu
            450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                    485                 490                 495
Val Thr Val Ala His Thr Gly Gln His Asp Leu Val Ile Pro Pro Asn
            500                 505                 510
```

Gly Tyr Phe Arg Phe Asp Ser Trp Val Asn Gln Phe Tyr Thr Leu Ala
    515                 520                 525

Pro Met Gly Asn Gly Thr Gly Arg Arg Arg Ala Val
    530                 535                 540

<210> SEQ ID NO 48
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_A39V plus sign P80S plus sign M333V

<400> SEQUENCE: 48
atgaagatgg ctagctcaga cgccaatcca agcgacggta gcgctgccaa cctcgtgccc    60
gaggtcaaca cgaagttat  ggcccttgag cccgtggttg gagctgctat agctgtgcct   120
gttgctgggc agcagaacgt gatagaccca tggatacgta acaactttgt tcaggccccc   180
ggtggagagt ttacagtcag cccaagaaac gctcctggag agatactgtg gagcgcctcc   240
ctcggccccg acctcaaccc ctatctgtca catctcgctc gcatgtataa cggctatgct   300
ggcggttttg aagttcaggt catccttgcc ggaaacgcct tcaccgctgg aagataatc   360 tttgctgctg tcccacccaa cttttccaact gagggcctga gcccaagcca ggttacaatg   420 ttccacaca tgatagttga tgtcagacag ctggagccag tccttatacc cctgccgat   480 gtccgaaaca acttctacca ctataatcag agcaacgaca gcacaatcaa gctcatcgct   540
atgctctaca caccactgag agccaacaac gcaggagatg acgtgtttac agtgtcatgt   600
agagtcctca aagaccaag ccctgatttt gatttcatct tcctcgtgcc gccaactgtt   660
gagagcagaa ctaagccctt ttctgttccc gtgctgacag ttgaggaaat gacaaattct   720
agatttccaa tccccttga aaagctgttt acgggaccaa gctctgcctt cgtggtgcag   780
ccacagaatg tcgatgtac aacagacggc gtcctgctcg gtacaacaca gctcagccct   840
gttaacatat gcacttttag gggcgatgtt acacatatca ctggttctca caactatact   900
atgaacctgg ccagccagaa ctggaacaac tacgacccaa cagaggagat ccctgctcca   960
cttgggacac ccgactttgt tggaaagatc cagggcgtgc tgacacagac gacaaagaca  1020
gatggttcaa caagaggtca caagctact gtttacaccg gtctgccga tttcgcacca  1080 aaactcggta gagtgcagtt tcagacagat acagatcacg actttgaagc caaccagaac  1140
actaagttta caccagtcgg agttatccaa gacggcaaca caacacacag aaacgagcca  1200
cagcaatggg tccttccaag ctatagcggc cggaacacac acaacgttca ccttgctccc  1260
gccgttgctc caacatttcc cggggagcag cttctttct tccgctctac aatgcccggg  1320
tgctctggat acccaaatat ggatctggac tgcctcctgc cgcaagaatg ggtgcagtat  1380
ttttaccaag aggcagctcc agctcagtct gatgttgccc tgctccggtt tgtgaacccc  1440
gatactggcc gggtccttt tgagtgcaag ctccataaga gcggatatgt gacagtcgct  1500
catactggcc agcacgacct cgttatccct cctaacggtt acttccgatt tgatagctgg  1560
gttaaccagt ttacacact tgcccctatg ggcaacggta caggccgcag agagccgtg   1620 tag                                                              1623

<210> SEQ ID NO 49
<211> LENGTH: 540
<212> TYPE: PRT
<213> ORGANISM: Norovirus

<400> SEQUENCE: 49

Met Lys Met Ala Ser Ser Asp Ala Asn Pro Ser Asp Gly Ser Ala Ala
1               5                   10                  15

Asn Leu Val Pro Glu Val Asn Glu Val Met Ala Leu Glu Pro Val
            20                  25                  30

Val Gly Ala Ala Ile Ala Val Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
            115                 120                 125

Pro Thr Glu Gly Leu Ser Pro Ser Gln Val Thr Met Phe Pro His Met
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
        210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
        290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
            355                 360                 365

Thr Asp Thr Asp His Asp Phe Glu Ala Asn Gln Asn Thr Lys Phe Thr
        370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val

```
                405                 410                 415
His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 50
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_A39V plus sign P80Splus sign Q386E

<400> SEQUENCE: 50
atgaagatgg ctagctcaga cgccaatcca agcgacggta gcgctgccaa cctcgtgccc     60
gaggtcaaca acgaagttat ggcccttgag cccgtggttg gagctgctat agctgtgcct    120
gttgctgggc agcagaacgt gatagaccca tggatacgta acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag     780
ccacagaatg gtcgatgtac aacagacggc gtcctgctcg gtacaacaca gctcagccct    840
gttaacatat gcacttttag ggcgatgtt acacatatca ctggttctca caactatact     900
atgaacctgg ccagccagaa ctggaacaac tacgacccaa cagaggagat ccctgctcca    960
cttgggacac ccgactttgt tggaaagatc cagggcatgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
```

```
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag gagagccgtg    1620
tag                                                                  1623
```

<210> SEQ ID NO 51
<211> LENGTH: 540
<212> TYPE: PRT
<213> ORGANISM: Norovirus

<400> SEQUENCE: 51

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300
```

| | | | | | | | | | | | | |
|---|---|---|---|---|---|---|---|---|---|---|---|---|
|Ser|Gln|Asn|Trp|Asn|Asn|Tyr|Asp|Pro|Thr|Glu|Ile|Pro|Ala|Pro|
|305| | | |310| | | |315| | | |320| | |

Ser Gln Asn Trp Asn Asn Tyr Asp Pro Thr Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
            355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
                515                 520                 525

Pro Met Gly Asn Gly Thr Gly Arg Arg Arg Ala Val
530                 535                 540

<210> SEQ ID NO 52
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_A39V plus sign P80S plus sign M333V plus sign
      Q386E

<400> SEQUENCE: 52

```
atgaagatgg ctagctcaga cgccaatcca agcgacggta gcgctgccaa cctcgtgccc      60
gaggtcaaca acgaagttat ggcccttgag cccgtggttg gagctgctat agctgtgcct     120
gttgctgggc agcagaacgt gatagaccca tggatacgta acaactttgt tcaggccccc     180
ggtggagagt ttacagtcag cccaagaaac gctcctggag agatactgtg gagcgcctcc     240
ctcggccccg acctcaaccc ctatctgtca catctcgctc gcatgtataa cggctatgct     300
ggcggttttg aagttcaggt catccttgcc ggaaacgcct tcaccgctgg gaagataatc     360
tttgctgctg tcccacccaa ctttccaact gagggcctga gcccaagcca ggttacaatg     420
tttccacaca tgatagttga tgtcagacag ctggagccag tccttatacc cctgcccgat     480
gtccgaaaca acttctacca ctataatcag agcaacgaca gcacaatcaa gctcatcgct     540
atgctctaca caccactgag agccaacaac gcaggagatg acgtgtttac agtgtcatgt     600
agagtcctca caagaccaag ccctgatttt gatttcatct tcctcgtgcc gccaactgtt     660
```

```
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcactttag gggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttctttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgccccctatg ggcaacggta caggccgcag agagccgtg   1620
tag                                                                1623
```

<210> SEQ ID NO 53
<211> LENGTH: 540
<212> TYPE: PRT
<213> ORGANISM: Norovirus

<400> SEQUENCE: 53

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
```

```
                195                 200                 205
Asp Phe Asp Phe Ile Phe Leu Val Pro Pro Thr Val Glu Ser Arg Thr
210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Ala Val
    530                 535                 540

<210> SEQ ID NO 54
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_R53I plus sign P80S

<400> SEQUENCE: 54
atgaagatgg ctagctcaga cgccaatcca agcgacggta gcgctgccaa cctcgtgccc      60
gaggtcaaca acgaagttat ggcccttgag cccgtggttg gagctgctat agctgctcct     120
```

```
gttgctgggc agcagaacgt gatagaccca tggataatca acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg aagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca aagaccaag ccctgatttt gatttcatct tcctcgtgcc gccaactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca aactatact    900
atgaacctgg ccagccagaa ctggaacaac tacgacccaa cagaggagat ccctgctcca    960
cttgggacac ccgactttgt tggaaagatc cagggcatgc tgacacagac gacaaagaca    1020
gatggttcaa caagaggtca caaagctact gtttacaccg gctctgccga tttcgcacca    1080
aaactcggta gagtgcagtt tcagacagat acagatcacg actttgaagc caaccagaac    1140
actaagttta caccagtcgg agttatccag gacggcaaca caacacacag aaacgagcca    1200
cagcaatggg tccttccaag ctatagcggc cggaacacac acaacgttca ccttgctccc    1260
gccgttgctc caacatttcc cggggagcag cttcttttct tccgctctac aatgcccggg    1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatcccct cctaacggtt acttccgatt tgatagctgg    1560
gttaaccagt tttacacact tgcccctatg ggcaacggta caggccgcag agagccgtg    1620
tag                                                                  1623
```

<210> SEQ ID NO 55
<211> LENGTH: 540
<212> TYPE: PRT
<213> ORGANISM: Norovirus

<400> SEQUENCE: 55

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95
```

```
Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
```

Pro Met Gly Asn Gly Thr Gly Arg Arg Arg Ala Val
    515             520             525
530             535             540

<210> SEQ ID NO 56
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_R53I plus sign P80S plus sign M333V

<400> SEQUENCE: 56

```
atgaagatgg ctagctcaga cgccaatcca agcgacggta gcgctgccaa cctcgtgccc     60
gaggtcaaca acgaagttat ggcccttgag cccgtggttg gagctgctat agctgctcct    120
gttgctgggc agcagaacgt gatagaccca tggataatca acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tcagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttctttttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag gagagccgtg   1620
tag                                                                 1623
```

<210> SEQ ID NO 57
<211> LENGTH: 540
<212> TYPE: PRT
<213> ORGANISM: Norovirus

<400> SEQUENCE: 57

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Ile Ile Phe Ala Ala Val Pro Pro Asn Phe
            115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
    355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415
```

```
His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
        450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
        530                 535                 540

<210> SEQ ID NO 58
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_R53I plus sign P80S  plus sign Q386E

<400> SEQUENCE: 58
atgaagatgg ctagctcaga cgccaatcca agcgacggta cgctgccaa cctcgtgccc    60 gaggtcaaca cgaagttat ggcccttgag cccgtggttg gagctgctat agctgctcct   120
gttgctgggc agcagaacgt gatagaccca tggataatca acaactttgt tcaggccccc   180
ggtggagagt ttacagtcag cccaagaaac gctcctggag atactgtg agcgcctcc    240 ctcggccccg acctcaaccc ctatctgtca catctcgctc gcatgtataa cggctatgct   300
ggcggttttg aagttcaggt catccttgcc ggaaacgcct tcaccgctgg aagataatc    360 tttgctgctg tcccacccaa cttttccaact gagggcctga gcccaagcca ggttacaatg   420
tttccacaca tgatagttga tgtcagacag ctggagccag tccttatacc cctgcccgat   480
gtccgaaaca acttctacca ctataatcag agcaacgaca gcacaatcaa gctcatcgct   540
atgctctaca caccactgag agccaacaac gcaggagatg acgtgtttac agtgtcatgt   600
agagtcctca aagaccaag ccctgatttt gatttcatct tcctcgtgcc gccaactgtt   660
gagagcagaa ctaagccctt ttctgttccc gtgctgacga ttgaggaaat gacaaattct   720
agatttccaa tccccctgga aaagctgttt acgggaccaa gctctgcctt cgtggtgcag   780
ccacagaatg tcgatgtac aacagacggc gtcctgctcg gtacaacaca gctcagccct   840
gttaacatat gcacttttag gggcgatgtt acacatatca ctggttctca aactatact   900 atgaacctgg ccagccagaa ctggaacaac tacgacccaa cagaggagat ccctgctcca   960
cttgggacac ccgactttgt tggaaagatc cagggcatgc tgacacagac gacaaagaca  1020
gatggttcaa caagaggtca caaagctact gtttacaccg ctctgccga tttcgcacca  1080 aaactcggta gagtgcagtt tgagacagat acagatcacg actttgaagc caaccagaac  1140
actaagttta caccagtcgg agttatccag gacggcaaca caacacacag aaacgagcca  1200
cagcaatggg tccttccaag ctatagcggc cggaacacac acaacgttca ccttgctccc  1260
gccgttgctc caacatttcc cggggagcag cttcttttct tccgctctac aatgcccggg  1320
```

```
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtccttt tgagtgcaag ctccataaga gcggatatgt gacagtcgct    1500
catactggcc agcacgacct cgttatccct cctaacggtt acttccgatt tgatagctgg   1560
gttaaccagt tttacacact tgccctatg ggcaacggta caggccgcag agagccgtg    1620 tag                                                                 1623
```

<210> SEQ ID NO 59
<211> LENGTH: 540
<212> TYPE: PRT
<213> ORGANISM: Norovirus

<400> SEQUENCE: 59

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Ile Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Ser Val Pro Val Leu Thr Val Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
290                 295                 300

Ser Gln Asn Trp Asn Asn Tyr Asp Pro Thr Glu Glu Ile Pro Ala Pro
305                 310                 315                 320
```

| | | | | | | | | | | |
|---|---|---|---|---|---|---|---|---|---|---|
|Leu|Gly|Thr|Pro|Asp|Phe|Val|Gly|Lys|Ile|Gln|Gly|Met|Leu|Thr|Gln|
| | | |325| | | |330| | | |335| | | | |

Leu Gly Thr Pro Asp Phe Val Gly Lys Ile Gln Gly Met Leu Thr Gln
            325                 330                 335

Thr Thr Lys Thr Asp Gly Ser Thr Arg Gly His Lys Ala Thr Val Tyr
        340                 345                 350

Thr Gly Ser Ala Asp Phe Ala Pro Lys Leu Gly Arg Val Gln Phe Glu
            355                 360                 365

Thr Asp Thr Asp His Asp Phe Glu Ala Asn Gln Asn Thr Lys Phe Thr
        370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
        450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
                515                 520                 525

Pro Met Gly Asn Gly Thr Gly Arg Arg Arg Ala Val
        530                 535                 540

<210> SEQ ID NO 60
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_R53I plus sign P80S plus sign M333V plus sign
      Q386E

<400> SEQUENCE: 60 atgaagatg

```
agatttccaa tcccccttga aaagctgttt acgggaccaa gctctgcctt cgtggtgcag        780
ccacagaatg gtcgatgtac aacagacggc gtcctgctcg gtacaacaca gctcagccct        840
gttaacatat gcacttttag gggcgatgtt acacatatca ctggttctca caactatact        900
atgaacctgg ccagccagaa ctggaacaac tacgacccaa cagaggagat ccctgctcca        960
cttgggacac ccgactttgt tggaaagatc cagggcgtgc tgacacagac gacaaagaca       1020
gatggttcaa caagaggtca caaagctact gtttacaccg gctctgccga tttcgcacca       1080
aaactcggta gagtgcagtt tgagacagat acagatcacg actttgaagc caaccagaac       1140
actaagttta caccagtcgg agttatccag gacggcaaca caacacacag aaacgagcca       1200
cagcaatggg tccttccaag ctatagcggc cggaacacac acaacgttca ccttgctccc       1260
gccgttgctc caacatttcc cggggagcag cttctttct tccgctctac aatgcccggg        1320
tgctctggat acccaaatat ggatctggac tgcctcctgc cgcaagaatg ggtgcagtat       1380
ttttaccaag aggcagctcc agctcagtct gatgttgccc tgctccggtt tgtgaaccc        1440 gatactggcc gggtcctttt tgagtgcaag ctccataaga gcggatatgt gacagtcgct       1500
catactggcc agcacgacct cgttatccct cctaacggtt acttccgatt tgatagctgg       1560
gttaaccagt tttacacact tgcccctatg ggcaacggta caggccgcag agagccgtg        1620 tag                                                                     1623
```

<210> SEQ ID NO 61
<211> LENGTH: 540
<212> TYPE: PRT
<213> ORGANISM: Norovirus

<400> SEQUENCE: 61

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Ile Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205
```

```
Asp Phe Asp Phe Ile Phe Leu Val Pro Pro Thr Val Glu Ser Arg Thr
    210                 215                 220
Lys Pro Phe Ser Val Pro Val Leu Thr Val Glu Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Thr Gly Ser His Asn Tyr Thr Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Lys Ile Gln Gly Val Leu Thr Gln
                325                 330                 335
Thr Thr Lys Thr Asp Gly Ser Thr Arg Gly His Lys Ala Thr Val Tyr
            340                 345                 350
Thr Gly Ser Ala Asp Phe Ala Pro Lys Leu Gly Arg Val Gln Phe Glu
        355                 360                 365
Thr Asp Thr Asp His Asp Phe Glu Ala Asn Gln Asn Thr Lys Phe Thr
    370                 375                 380
Pro Val Gly Val Ile Gln Asp Gly Asn Thr Thr His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln Tyr Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Val
    530                 535                 540
```

<210> SEQ ID NO 62
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_A39V plus sign R53I plus sign P80S

<400> SEQUENCE: 62

```
atgaagatgg ctagctcaga cgccaatcca agcgacggta gcgctgccaa cctcgtgccc      60
gaggtcaaca acgaagttat ggcccttgag cccgtggttg gagctgctat agctgtgcct     120
gttgctgggc agcagaacgt gatagaccca tggataatca acaactttgt tcaggccccc     180
```

```
ggtggagagt ttacagtcag cccaagaaac gctcctggag agatactgtg gagcgcctcc    240
ctcggcccg  acctcaaccc ctatctgtca catctcgctc gcatgtataa cggctatgct    300
ggcggttttg aagttcaggt catccttgcc ggaaacgcct tcaccgctgg aagataatc     360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag gggcgatgtt acacatatca ctggttctca aactatact    900
atgaacctgg ccagccagaa ctggaacaac tacgacccaa cagaggagat ccctgctcca    960
cttgggacac ccgactttgt tggaaagatc cagggcatgc tgacacagac gacaaagaca   1020
gatggttcaa caagaggtca caagctact gtttacaccg gctctgccga tttcgcacca   1080
aaactcggta gagtgcagtt tcagacagat acagatcacg actttgaagc caaccagaac   1140
actaagttta caccagtcgg agttatccag gacggcaaca acacacag aaacgagcca    1200
cagcaatggg tccttccaag ctatagcggc cggaacacac acaacgttca ccttgctccc   1260
gccgttgctc aacatttcc cggggagcag cttcttttct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag agagccgtg    1620
tag                                                                 1623

<210> SEQ ID NO 63
<211> LENGTH: 540
<212> TYPE: PRT
<213> ORGANISM: Norovirus

<400> SEQUENCE: 63

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110
```

```
Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
        130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
                195                 200                 205

Asp Phe Asp Phe Ile Phe Leu Val Pro Pro Thr Val Glu Ser Arg Thr
                210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
                275                 280                 285

Asp Val Thr His Ile Thr Gly Ser His Asn Tyr Thr Met Asn Leu Ala
                290                 295                 300

Ser Gln Asn Trp Asn Asn Tyr Asp Pro Thr Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
                340                 345                 350

Thr Gly Ser Ala Asp Phe Ala Pro Lys Leu Gly Arg Val Gln Phe Gln
                355                 360                 365

Thr Asp Thr Asp His Asp Phe Glu Ala Asn Gln Asn Thr Lys Phe Thr
                370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asp
                435                 440                 445

Leu Asp Cys Leu Leu Pro Gln Glu Trp Val Gln Tyr Phe Tyr Gln Glu
                450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
                515                 520                 525
```

```
Pro Met Gly Asn Gly Thr Gly Arg Arg Arg Ala Val
    530                 535                 540
```

<210> SEQ ID NO 64
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_A39V plus sign R53I plus sign P80S plus sign M333V

<400> SEQUENCE: 64

```
atgaagatgg ctagctcaga cgccaatcca agcgacggta gcgctgccaa cctcgtgccc      60
gaggtcaaca acgaagttat ggcccttgag cccgtggttg gagctgctat agctgtgcct     120
gttgctgggc agcagaacgt gatagaccca tggataatca acaactttgt tcaggccccc     180
ggtggagagt ttacagtcag cccaagaaac gctcctggag agatactgtg gagcgcctcc     240
ctcggccccg acctcaaccc ctatctgtca catctcgctc gcatgtataa cggctatgct     300
ggcggttttg aagttcaggt catccttgcc ggaaacgcct tcaccgctgg gaagataatc     360
tttgctgctg tcccacccaa ctttccaact gagggcctga gcccaagcca ggttacaatg     420
tttccacaca tgatagttga tgtcagacag ctggagccag tccttatacc cctgcccgat     480
gtccgaaaca acttctacca ctataatcag agcaacgaca gcacaatcaa gctcatcgct     540
atgctctaca caccactgag agccaacaac gcaggagatg acgtgtttac agtgtcatgt     600
agagtcctca caagaccaag ccctgatttt gatttcatct tcctcgtgcc gccaactgtt     660
gagagcagaa ctaagccctt ttctgttccc gtgctgacag ttgaggaaat gacaaattct     720
agatttccaa tccccttga aaagctgttt acgggaccaa gctctgcctt cgtggtgcag      780
ccacagaatg gtcgatgtac aacagacggc gtcctgctcg gtacaacaca gctcagccct     840
gttaacatat gcacttttag gggcgatgtt acacatatca ctggttctca caactatact     900
atgaacctgg ccagccagaa ctggaacaac tacgacccaa cagaggagat ccctgctcca     960
cttgggacac ccgactttgt tggaaagatc cagggcgtgc tgacacagac gacaaagaca    1020
gatggttcaa caagaggtca caaagctact gtttacaccg gctctgccga tttcgcacca    1080
aaactcggta gagtgcagtt tcagacagat acagatcacg actttgaagc caaccagaac    1140
actaagttta caccagtcgg agttatccag gacggcaaca caacacacag aaacgagcca    1200
cagcaatggg tccttccaag ctatagcggc cggaacacac acaacgttca ccttgctccc    1260
gccgttgctc caacatttcc cggggagcag cttctttttct tccgctctac aatgcccggg   1320
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtcctttt tgagtgcaag ctccataaga gcggatatgt gacagtcgct    1500
catactggcc agcacgacct cgttatccct cctaacggtt acttccgatt tgatagctgg    1560
gttaaccagt tttacacact tgcccctatg ggcaacggta caggccgcag gagagccgtg    1620
tag                                                                  1623
```

<210> SEQ ID NO 65
<211> LENGTH: 540
<212> TYPE: PRT
<213> ORGANISM: Norovirus

<400> SEQUENCE: 65

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Gln
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
```

```
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 66
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu
      cod VP1 GII.4/2015_A39Vplus sign R53I plus sign P80S plus sign
      Q386E

<400> SEQUENCE: 66
atgaagatgg ctagctcaga cgccaatcca agcgacggta gcgctgccaa cctcgtgccc     60
gaggtcaaca acgaagttat ggcccttgag cccgtggttg gagctgctat agctgtgcct    120
gttgctgggc agcagaacgt gatagaccca tggataatca acaactttgt tcaggccccc    180
ggtggagagt ttacagtcag cccaagaaac gctcctggag agatactgtg gagcgcctcc    240
ctcggccccg acctcaaccc ctatctgtca catctcgctc gcatgtataa cggctatgct    300
ggcggttttg aagttcaggt catccttgcc ggaaacgcct tcaccgctgg gaagataatc    360
tttgctgctg tcccacccaa ctttccaact gagggcctga gcccaagcca ggttacaatg    420
tttccacaca tgatagttga tgtcagacag ctggagccag tccttatacc cctgcccgat    480
gtccgaaaca acttctacca ctataatcag agcaacgaca gcacaatcaa gctcatcgct    540
atgctctaca caccactgag agccaacaac gcaggagatg acgtgtttac agtgtcatgt    600
agagtcctca caagaccaag ccctgatttt gatttcatct tcctcgtgcc gccaactgtt    660
gagagcagaa ctaagccctt ttctgttccc gtgctgacag ttgaggaaat gacaaattct    720
agatttccaa tccccttga aaagctgttt acgggaccaa gctctgcctt cgtggtgcag    780
ccacagaatg gtcgatgtac aacagacggc gtcctgctcg gtacaacaca gctcagccct    840
gttaacatat gcacttttag ggcgatgtt acacatatca ctggttctca caactatact    900
atgaacctgg ccagccagaa ctggaacaac tacgacccaa cagaggagat ccctgctcca    960
cttgggacac ccgactttgt tggaaagatc cagggcatgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttcttttct tccgctctac aatgcccggg   1320
```

-continued

```
tgctctggat acccaaatat ggatctggac tgcctcctgc cgcaagaatg ggtgcagtat    1380
ttttaccaag aggcagctcc agctcagtct gatgttgccc tgctccggtt tgtgaacccc    1440
gatactggcc gggtccttt tgagtgcaag ctccataaga gcggatatgt gacagtcgct     1500
catactggcc agcacgacct cgttatccct cctaacggtt acttccgatt tgatagctgg    1560
gttaaccagt tttacacact tgccctatg ggcaacggta caggccgcag agagccgtg     1620 tag                                                                   1623
```

<210> SEQ ID NO 67
<211> LENGTH: 540
<212> TYPE: PRT
<213> ORGANISM: Norovirus

<400> SEQUENCE: 67

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Val Pro Val Ala Gly Gln Gln Asn Val Ile
            35                  40                  45

Asp Pro Trp Ile Ile Asn Asn Phe Val Gln Ala Pro Gly Gly Glu Phe
        50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Ile Ile Phe Ala Ala Val Pro Pro Asn Phe
            115                 120                 125

Pro Thr Glu Gly Leu Ser Pro Ser Gln Val Thr Met Phe Pro His Met
        130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Ser Val Pro Val Leu Thr Val Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320
```

```
Leu Gly Thr Pro Asp Phe Val Gly Lys Ile Gln Gly Met Leu Thr Gln
                325                 330                 335

Thr Thr Lys Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Asn Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 68
<211> LENGTH: 1623
<212> TYPE: DNA
<213> ORGANISM: Artificial Sequence
<220> FEATURE:
<223> OTHER INFORMATION: Synthetic sequence, nucleic acid sequence of Hu cod VP1 GII.4/2015_A39V plus sign R53I plus sign P80S plus sign M333V plus sign Q386E

<400> SEQUENCE: 68

```
atgaagatgg ctagctcaga cgccaatcca agcgacggta gcgctgccaa cctcgtgccc      60
gaggtcaaca acgaagttat ggcccttgag cccgtggttg gagctgctat agctgtgcct     120
gttgctgggc agcagaacgt gatagaccca tggataatca acaactttgt tcaggccccc     180
ggtggagagt ttacagtcag cccaagaaac gctcctggag agatactgtg gagcgcctcc     240
ctcggccccg acctcaaccc ctatctgtca catctcgctc gcatgtataa cggctatgct     300
ggcggttttg aagttcaggt catccttgcc ggaaacgcct tcaccgctgg gaagataatc     360
tttgctgctg tcccacccaa ctttccaact gagggcctga gcccaagcca ggttacaatg     420
tttccacaca tgatagttga tgtcagacag ctggagccag tccttatacc cctgcccgat     480
gtccgaaaca acttctacca ctataatcag agcaacgaca gcacaatcaa gctcatcgct     540
atgctctaca caccactgag agccaacaac gcaggagatg acgtgtttac agtgtcatgt     600
agagtcctca caagaccaag ccctgatttt gatttcatct tcctcgtgcc gccaactgtt     660
gagagcagaa ctaagccctt ttctgttccc gtgctgacag ttgaggaaat gacaaattct     720
```

```
agatttccaa tcccccttga aaagctgttt acgggaccaa gctctgcctt cgtggtgcag    780
ccacagaatg gtcgatgtac aacagacggc gtcctgctcg gtacaacaca gctcagccct    840
gttaacatat gcactttag gggcgatgtt acacatatca ctggttctca caactatact     900
atgaacctgg ccagccagaa ctggaacaac tacgacccaa cagaggagat ccctgctcca    960
cttgggacac ccgactttgt tggaaagatc cagggcgtgc tgacacagac gacaaagaca   1020
gatggttcaa caagaggtca caaagctact gtttacaccg gctctgccga tttcgcacca   1080
aaactcggta gagtgcagtt tgagacagat acagatcacg actttgaagc caaccagaac   1140
actaagttta caccagtcgg agttatccag gacggcaaca caacacacag aaacgagcca   1200
cagcaatggg tccttccaag ctatagcggc cggaacacac acaacgttca ccttgctccc   1260
gccgttgctc caacatttcc cggggagcag cttctttcct tccgctctac aatgcccggg   1320
tgctctggat acccaaatat ggatctggac tgcctcctgc cgcaagaatg ggtgcagtat   1380
ttttaccaag aggcagctcc agctcagtct gatgttgccc tgctccggtt tgtgaacccc   1440
gatactggcc gggtcctttt tgagtgcaag ctccataaga gcggatatgt gacagtcgct   1500
catactggcc agcacgacct cgttatccct cctaacggtt acttccgatt tgatagctgg   1560
gttaaccagt tttacacact tgcccctatg ggcaacggta caggccgcag agagccgtg    1620 tag                                                                1623
```

<210> SEQ ID NO 69
<211> LENGTH: 540
<212> TYPE: PRT
<213> ORGANISM: Norovirus

<400> SEQUENCE: 69

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Val Pro Val Ala Gly Gln Gln Asn Val Ile
        35                  40                  45

Asp Pro Trp Ile Ile Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Met
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205
```

-continued

```
Asp Phe Asp Phe Ile Phe Leu Val Pro Pro Thr Val Glu Ser Arg Thr
    210                 215                 220
Lys Pro Phe Ser Val Pro Val Leu Thr Val Glu Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Thr Gly Ser His Asn Tyr Thr Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Lys Ile Gln Gly Val Leu Thr Gln
                325                 330                 335
Thr Thr Lys Thr Asp Gly Ser Thr Arg Gly His Lys Ala Thr Val Tyr
            340                 345                 350
Thr Gly Ser Ala Asp Phe Ala Pro Lys Leu Gly Arg Val Gln Phe Glu
        355                 360                 365
Thr Asp Thr Asp His Asp Phe Glu Ala Asn Gln Asn Thr Lys Phe Thr
    370                 375                 380
Pro Val Gly Val Ile Gln Asp Gly Asn Thr Thr His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln Tyr Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Val
    530                 535                 540

<210> SEQ ID NO 70
<211> LENGTH: 5491
<212> TYPE: DNA
<213> ORGANISM: Artificial Sequence
<220> FEATURE:
<223> OTHER INFORMATION: Synthetic sequence, nucleic acid sequence of
      Cloning vector 3674 from left to right T-DNA

<400> SEQUENCE: 70
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacatttta cttgaacaaa      180
```

```
aatattcacc tactactgtt ataaatcatt attaaacatt agagtaaaga aatatggatg      240
ataagaacaa gagtagtgat attttgacaa caattttgtt gcaacatttg agaaaatttt      300
gttgttctct cttttcattg gtcaaaaaca atagagagag aaaaaggaag agggagaata      360
aaaacataat gtgagtatga gagagaaagt tgtacaaaag ttgtaccaaa atagttgtac      420
aaatatcatt gaggaatttg acaaaagcta cacaaataag ggttaattgc tgtaaataaa      480
taaggatgac gcattagaga gatgtaccat tagagaattt ttggcaagtc attaaaaaga      540
aagaataaat tattttaaa attaaagtt gagtcatttg attaaacatg tgattattta        600
atgaattgat gaaagagttg gattaaagtt gtattagtaa ttagaatttg gtgtcaaatt      660
taatttgaca tttgatcttt tcctatatat tgccccatag agtcagttaa ctcatttta       720 tatttcatag atcaaataag agaaataacg gtatattaat ccctccaaaa aaaaaaacg       780 gtatatttac taaaaaatct aagccacgta ggaggataac aggatccccg taggaggata      840
acatccaatc caaccaatca caacaatcct gatgagataa cccactttaa gcccacgcat      900
ctgtggcaca tctacattat ctaaatcaca cattcttcca cacatctgag ccacacaaaa      960
accaatccac atctttatca cccattctat aaaaaatcac actttgtgag tctacacttt     1020
gattcccttc aaacacatac aaagagaaga gactaattaa ttaattaatc atcttgagag     1080
aaaatggaac gagctataca aggaaacgac gctagggaac aagctaacag tgaacgttgg     1140
gatggaggat caggaggtac cacttctccc ttcaaacttc ctgacgaaag tccgagttgg     1200
actgagtggc ggctacataa cgatgagacg aattcgaatc aagataatcc ccttggtttc     1260
aaggaaagct ggggtttcgg gaaagttgta tttaagagat atctcagata cgacaggacg     1320
gaagcttcac tgcacagagt ccttggatct tggacgggag attcggttaa ctatgcagca     1380
tctcgatttt tcggtttcga ccagatcgga tgtacctata gtattcggtt tcgaggagtt     1440
agtatcaccg tttctggagg gtcgcgaact cttcagcatc tctgtgagat ggcaattcgg     1500
tctaagcaag aactgctaca gcttgcccca atcgaagtgg aaagtaatgt atcaagagga     1560
tgccctgaag gtactcaaac cttcgaaaaa gaaagcgagt aagttaaaat gcttcttcgt     1620
ctcctattta taatatggtt tgttattgtt aattttgttc ttgtagaaga gcttaattaa     1680
tcgttgttgt tatgaaatac tatttgtatg agatgaactg gtgtaatgta attcatttac     1740
ataagtggag tcagaatcag aatgtttcct ccataactaa ctagacatga agacctgccg     1800
cgtacaattg tcttatattt gaacaactaa aattgaacat cttttgccac aactttataa     1860
gtggttaata tagctcaaat atatggtcaa gttcaataga ttaataatgg aaatatcagt     1920
tatcgaaatt cattaacaat caacttaacg ttattaacta ctaattttat atcatcccct     1980
ttgataaatg atagtacacc aattaggaag gagcatgctc gcctaggaga ttgtcgtttc     2040
ccgccttcag tttgcaagct gctctagccg tgtagccaat acgcaaaccg cctctccccg     2100
cgcgttggga attactagcg cgtgtcgaca agcttcatg ccggtcaaca tggtggagca      2160
cgacacactt gtctactcca aaaatatcaa agatacagtc tcagaagacc aaagggcaat     2220
tgagactttt caacaaaggg taatatccgg aaacctcctc ggattccatt gcccagctat     2280
ctgtcacttt attgtgaaga tagtggaaaa ggaaggtggc tcctacaaat gccatcattg     2340
cgataaagga aaggccatcg ttgaagatgc ctctgccgac agtggtccca aagatggacc     2400
cccacccacg aggagcatcg tggaaaaaga agacgttcca accacgtctt caaagcaagt     2460
ggattgatgt gataacatgg tggagcacga cacacttgtc tactccaaaa atatcaaaga     2520
```

```
tacagtctca gaagaccaaa gggcaattga gacttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggaccccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct atataaggaa gttcatttca    2880
tttggagagg ataacaattt aaacaaacaa aatcaacaaa tatagaaaat aacgcatttc    2940
caattctttg aaatttctga cgtcactcct cagccaaaac gacaccccca tctgtctatc    3000
cactggcccc tggatctgct gcccaaacta actccatggt gaccctggga tgcctggtca    3060
agggctattt ccctgagcca gtgacagtga cctggaactc tggatccctg tccagcggtg    3120
tgcacacctt cccagctgtc ctgcagtctg acctctacac tctgagcagc tcagtgactg    3180
tcccctccag cacctggccc agcgagaccg tcacctgcaa cgttgcccac ccggccagca    3240
gcaccaaggt ggacaagaaa attgtgccca gggattgtgg ttgtaagcct tgcatatgta    3300
cagtcccaga agtatcatct gtcttcatct tcccccaaa gcccaaggat gtgctcacca    3360
ttactctgac tcctaaggtc acgtgtgttg tggtagacat cagcaaggat gatcccgagg    3420
tccagttcag ctggtttgta gatgatgtgg aggtgcacac agctcagacg caaccccggg    3480
aggagcagtt caacagcact ttccgctcag tcagtgaact tcccatcatg caccaggact    3540
ggctcaatgg caaggagcga tcgctcacca tcaccatcac catcaccatc accattaaag    3600
gcctattttc tttagtttga atttactgtt attcggtgtg catttctatg tttggtgagc    3660
ggttttctgt gctcagagtg tgtttatttt atgtaattta atttctttgt gagctcctgt    3720
ttagcaggtc gtcccttcag caaggacaca aaaagatttt aattttatta tcgttcaaac    3780
atttggcaat aaagtttctt aagattgaat cctgttgccg tcttgcgat gattatcata    3840 taatttctgt tgaattacgt taagcatgta ataattaaca tgtaatgcat gacgttattt    3900
atgagatggg ttttatgat tagagtcccg caattataca tttaatacgc gatagaaaac    3960
aaaatatagc gcgcaaacta ggataaatta tcgcgcgcgg tgtcatctat gttactagat    4020
ctctaggtaa aaatcccaat tatatttggt ctaatttagt ttggtattga gtaaaacaaa    4080
ttcgaaccaa accaaaatat aaatatatag tttttatata tatgccttta agactttta    4140 tagaattttc tttaaaaaat atctagaaat atttgcgact cttctggcat gtaatatttc    4200
gttaaatatg aagtgctcca tttttattaa ctttaaataa ttggttgtac gatcactttc    4260
ttatcaagtg ttactaaaat gcgtcaatct ctttgttctt ccatattcat atgtcaaaat    4320
ctatcaaaat tcttatatat cttttcgaa tttgaagtga aatttcgata atttaaaatt    4380
aaatagaaca tatcattatt taggtatcat attgattttt atacttaatt actaaatttg    4440
gttaactttg aaagtgtaca tcaacgaaaa attagtcaaa cgactaaaat aaataaatat    4500
catgtgttat taagaaaatt ctcctataag aatatttta tagatcatat gtttgtaaaa    4560
aaaattaatt tttactaaca catatattta cttatcaaaa atttgacaaa gtaagattaa    4620
aataatattc atctaacaaa aaaaaaacca gaaaatgctg aaaacccggc aaaaccgaac    4680
caatccaaac cgatatagtt ggtttggttt gattttgata taaaccgaac caactcggtc    4740
catttgcacc cctaatcata atagctttaa tatttcaaga tattattaag ttaacgttgt    4800
caatatcctg gaaatttgc aaaatgaatc aagcctatat ggctgtaata tgaatttaaa    4860
agcagctcga tgtggtggta atatgtaatt tacttgattc taaaaaata tcccaagtat    4920
```

| | |
|---|---|
| taataatttc tgctaggaag aaggttagct acgatttaca gcaaagccag aatacaaaga | 4980 |
| accataaagt gattgaagct cgaaatatac gaaggaacaa atattttaa aaaaatacgc | 5040 |
| aatgacttgg aacaaaagaa agtgatatat tttttgttct taaacaagca tccccctctaa | 5100 |
| agaatggcag ttttcctttg catgtaacta ttatgctccc ttcgttacaa aaattttgga | 5160 |
| ctactattgg gaacttcttc tgaaaattct agagtctcaa gcttggcgcg cccacgtgac | 5220 |
| tagtggcact ggccgtcgtt ttacaacgtc gtgactggga aaaccctggc gttacccaac | 5280 |
| ttaatcgcct tgcagcacat ccccctttcg ccagctggcg taatagcgaa gaggcccgca | 5340 |
| ccgatcgccc ttcccaacag ttgcgcagcc tgaatggcga atgctagagc agcttgagct | 5400 |
| tggatcagat tgtcgtttcc cgccttcagt ttaaactatc agtgtttgac aggatatatt | 5460 |
| ggcgggtaaa cctaagagaa aagagcgttt a | 5491 |

<210> SEQ ID NO 71
<211> LENGTH: 2866
<212> TYPE: DNA
<213> ORGANISM: Norovirus

<400> SEQUENCE: 71

| | |
|---|---|
| gtcaacatgg tggagcacga cacacttgtc tactccaaaa atatcaaaga tacagtctca | 60 |
| gaagaccaaa gggcaattga gacttttcaa caaagggtaa tatccggaaa cctcctcgga | 120 |
| ttccattgcc cagctatctg tcactttatt gtgaagatag tggaaaagga aggtggctcc | 180 |
| tacaaatgcc atcattgcga taaggaaag gccatcgttg aagatgcctc tgccgacagt | 240 |
| ggtcccaaag atggaccccc acccacgagg agcatcgtgg aaaaagaaga cgttccaacc | 300 |
| acgtcttcaa gcaagtggga ttgatgtgat aacatggtgg agcacgacac acttgtctac | 360 |
| tccaaaaata tcaaagatac agtctcagaa gaccaagggg caattgagac ttttcaacaa | 420 |
| agggtaatat ccggaaaacct cctcggattc cattgcccag ctatctgtca ctttattgtg | 480 |
| aagatagtgg aaaaggaagg tggctcctac aaatgccatc attgcgataa ggaaaggcc | 540 |
| atcgttgaag atgcctctgc cgacagtggt cccaaagatg gacccccacc cacgaggagc | 600 |
| atcgtggaaa agaagacgt tccaaccacg tcttcaaagc aagtggattg atgtgatatc | 660 |
| tccactgacg taaggdatga cgcacaatcc cactatcctt cgcaagaccc ttcctctata | 720 |
| taaggaagtt catttcattt ggagaggata acaatttaaa caaacaaaat caacaaatat | 780 |
| agaaaataac gcatttccaa ttctttgaaa tttctgcaac aatgaagatg ctagctcag | 840 |
| acgccaatcc aagcgacggt agcgctgcca acctcgtgcc cgaggtcaac aacgaagtta | 900 |
| tggcccttga gccgtggtt ggagctgcta tagctgctcc tgttgctggg cagcagaacg | 960 |
| tgatagaccc atggatacgt aacaactttg ttcaggcccc cggtggagag tttacagtca | 1020 |
| gcccaagaaa cgctcctgga gagatactgt ggagcgcccc actcggcccc gacctcaacc | 1080 |
| cctatctgtc acatctcgct cgcatgtata acggctatgc tggcggtttt gaagttcagg | 1140 |
| tcatccttgc cggaaacgcc ttcaccgctg gaagataat ctttgctgct gtcccaccca | 1200 |
| actttccaac tgagggcctg agcccaagcc aggttacaat gtttccacac atgatagttg | 1260 |
| atgtcagaca gctggagcca gtccttatac ccctgcccga tgtccgaaac aacttctacc | 1320 |
| actataatca gagcaacgac agcacaatca agctcatcgc tatgctctac acaccactga | 1380 |
| gagccaacaa cgcaggagat gacgtgttta cagtgtcatg tagagtcctc acaagaccaa | 1440 |
| gccctgattt tgatttcatc ttcctcgtgc cgccaactgt tgagagcaga actaagccct | 1500 |

```
tttctgttcc cgtgctgaca gttgaggaaa tgacaaattc tagatttcca atccccttg    1560 aaaagctgtt tacgggacca agctctgcct tcgtggtgca gccacagaat ggtcgatgta    1620
caacagacgg cgtcctgctc ggtacaacac agctcagccc tgttaacata tgcacttta    1680 ggggcgatgt tacacatatc actggttctc acaactatac tatgaacctg ccagccaga    1740 actggaacaa ctacgaccca acagaggaga tccctgctcc acttgggaca cccgactttg    1800
ttggaaagat ccagggcatg ctgacacaga cgacaaagac agatggttca acaagaggtc    1860
acaaagctac tgtttacacc ggctctgccg atttcgcacc aaaactcggt agagtgcagt    1920
ttcagacaga tacagatcac gactttgaag ccaaccagaa cactaagttt acaccagtcg    1980
gagttatcca ggacggcaac acaacacaca gaaacgagcc acagcaatgg gtccttccaa    2040
gctatagcgg ccggaacaca cacaacgttc accttgctcc cgccgttgct ccaacatttc    2100
ccggggagca gcttcttttc ttccgctcta caatgcccgg gtgctctgga tacccaaata    2160
tggatctgga ctgcctcctg ccgcaagaat gggtgcagta ttttaccaa gaggcagctc    2220 cagctcagtc tgatgttgcc ctgctccggt tgtgaaccc cgatactggc cgggtccttt    2280
ttgagtgcaa gctccataag agcggatatg tgacagtcgc tcatactggc cagcacgacc    2340
tcgttatccc tcctaacggt tacttccgat ttgatagctg ggttaaccag ttttacacac    2400
ttgcccctat gggcaacggt acaggccgca ggagagccgt gtagaggcct attttcttta    2460
gtttgaattt actgttattc ggtgtgcatt tctatgtttg gtgagcggtt ttctgtgctc    2520
agagtgtgtt tattttatgt aatttaattt ctttgtgagc tcctgtttag caggtcgtcc    2580
cttcagcaag gacacaaaaa gattttaatt ttattatcgt tcaaacattt ggcaataaag    2640
tttcttaaga ttgaatcctg ttgccggtct tgcgatgatt atcatataat ttctgttgaa    2700
ttacgttaag catgtaataa ttaacatgta atgcatgacg ttatttatga gatgggtttt    2760
tatgattaga gtcccgcaat tatacattta atacgcgata gaaaacaaaa tatagcgcgc    2820
aaactaggat aaattatcgc gcgcggtgtc atctatgtta ctagat              2866
```

<210> SEQ ID NO 72
<211> LENGTH: 2866
<212> TYPE: DNA
<213> ORGANISM: Norovirus

<400> SEQUENCE: 72

```
gtcaacatgg tggagcacga cacttgtc tactccaaaa atatcaaaga tacagtctca     60
gaagaccaaa gggcaattga gactttcaa caaagggtaa tatccggaaa cctcctcgga    120
ttccattgcc cagctatctg tcactttatt gtgaagatag tggaaaagga aggtggctcc    180
tacaaatgcc atcattgcga taaggaaag gccatcgttg aagatgcctc tgccgacagt    240
ggtcccaaag atggaccccc acccacgagg agcatcgtgg aaaagaaga cgttccaacc    300 acgtcttcaa gcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa ggaaaggcc    540 atcgttgaag atgcctctgc cgacagtggt cccaaagatg gacccccacc cacgaggagc    600
atcgtggaaa agaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggata acaatttaaa caaacaaaat caacaaatat    780
```

```
agaaaataac gcatttccaa ttctttgaaa tttctgcaac aatgaagatg gctagctcag    840
acgccaatcc aagcgacggt agcgctgcca acctcgtgcc cgaggtcaac aacgaagtta    900
tggcccttga gcccgtggtt ggagctgcta gctgctcc tgttgctggg cagcagaacg     960
tgatagaccc atggatacgt aacaactttg ttcaggcccc cggtggagag tttacagtca    1020
gcccaagaaa cgctcctgga gagatactgt ggagcgcctc cctcggcccc gacctcaacc    1080
cctatctgtc acatctcgct cgcatgtata acggctatgc tggcggtttt gaagttcagg    1140
tcatccttgc cggaaacgcc ttcaccgctg ggaagataat ctttgctgct gtcccaccca    1200
actttccaac tgagggcctg agcccaagcc aggttacaat gtttccacac atgatagttg    1260
atgtcagaca gctggagcca gtccttatac ccctgcccga tgtccgaaac aacttctacc    1320
actataatca gagcaacgac agcacaatca agctcatcgc tatgctctac acaccactga    1380
gagccaacaa cgcaggagat gacgtgttta cagtgtcatg tagagtcctc acaagaccaa    1440
gccctgattt tgatttcatc ttcctcgtgc cgccaactgt tgagagcaga actaagccct    1500
tttctgttcc cgtgctgaca gttgaggaaa tgacaaattc tagatttcca atccccttg     1560 aaaagctgtt tacgggacca agctctgcct tcgtggtgca gccacagaat ggtcgatgta    1620
caacagacgg cgtcctgctc ggtacaacac agctcagccc tgttaacata tgcacttta    1680 ggggcgatgt tacacatatc actggttctc acaactatac tatgaacctg gccagccaga    1740
actggaacaa ctacgaccca acagaggaga tccctgctcc acttgggaca cccgactttg    1800
ttggaaagat ccagggcatg ctgacacaga cgacaaagac agatggttca acaagaggtc    1860
acaaagctac tgtttacacc ggctctgccg atttcgcacc aaaactcggt agagtgcagt    1920
ttcagacaga tacagatcac gactttgaag ccaaccagaa cactaagttt acaccagtcg    1980
gagttatcca ggacggcaac acaacacaca gaaacgagcc acagcaatgg gtccttccaa    2040
gctatagcgg ccggaacaca cacaacgttc accttgctcc cgccgttgct ccaacatttc    2100
ccggggagca gcttcttttc ttccgctcta caatgcccgg gtgctctgga tacccaaata    2160
tggatctgga ctgcctcctg ccgcaagaat gggtgcagta ttttttaccaa gaggcagctc    2220 cagctcagtc tgatgttgcc ctgctccggt tgtgaaccc cgatactggc cgggtccttt     2280
ttgagtgcaa gctccataag agcggatatg tgacagtcgc tcatactggc cagcacgacc    2340
tcgttatccc tcctaacggt tacttccgat ttgatagctg ggttaaccag ttttacacac    2400
ttgcccctat gggcaacggt acaggccgca ggagagccgt gtagaggcct atttctttta    2460
gtttgaattt actgttattc ggtgtgcatt tctatgtttg gtgagcggtt ttctgtgctc    2520
agagtgtgtt tattttatgt aatttaattt ctttgtgagc tcctgtttag caggtcgtcc    2580
cttcagcaag gacacaaaaa gatttttaatt ttattatcgt tcaaacattt ggcaataaag    2640
tttcttaaga ttgaatcctg ttgccggtct tgcgatgatt atcatataat ttctgttgaa    2700
ttacgttaag catgtaataa ttaacatgta atgcatgacg ttatttatga gatgggtttt    2760
tatgattaga gtcccgcaat tatacattta atacgcgata gaaaacaaaa tatagcgcgc    2820
aaactaggat aaattatcgc gcgcggtgtc atctatgtta ctagat                  2866
```

<210> SEQ ID NO 73
<211> LENGTH: 54
<212> TYPE: DNA
<213> ORGANISM: Artificial Sequence
<220> FEATURE:
<223> OTHER INFORMATION: Synthetic sequence, primer
      IF(nbPK74)GII.4Syd15(opt1).c

<400> SEQUENCE: 73
tctttgaaat tctgcaaca atgaagatgg ctagctcaga cgccaatcca agcg            54

<210> SEQ ID NO 74
<211> LENGTH: 49
<212> TYPE: DNA
<213> ORGANISM: Artificial Sequence
<220> FEATURE:
<223> OTHER INFORMATION: Synthetic sequence, primer
      IF-(Syd15)GII4(opt1).r

<400> SEQUENCE: 74
actaaagaaa ataggcctct acacggctct cctgcggcct gtaccgttg                 49

<210> SEQ ID NO 75
<211> LENGTH: 51
<212> TYPE: DNA
<213> ORGANISM: Artificial Sequence
<220> FEATURE:
<223> OTHER INFORMATION: Synthetic sequence, primer
      IF(nbPK74)GII.4Syd12.c

<400> SEQUENCE: 75
tctttgaaat tctgcaaca atgaaaatgg cctcgagtga cgctaaccct a               51

<210> SEQ ID NO 76
<211> LENGTH: 50
<212> TYPE: DNA
<213> ORGANISM: Artificial Sequence
<220> FEATURE:
<223> OTHER INFORMATION: Synthetic sequence, primer GII.4(P80S).r

<400> SEQUENCE: 76
gatcgggtcc caagctggcc gaccacagga tttctcctgg cgcatttctc                50

<210> SEQ ID NO 77
<211> LENGTH: 50
<212> TYPE: DNA
<213> ORGANISM: Artificial Sequence
<220> FEATURE:
<223> OTHER INFORMATION: Synthetic sequence, primer GII.4(P80S).c

<400> SEQUENCE: 77
aatcctgtgg tcggccagct tgggacccga tctgaacccc tatttgtcac                50

<210> SEQ ID NO 78
<211> LENGTH: 48
<212> TYPE: DNA
<213> ORGANISM: Artificial Sequence
<220> FEATURE:
<223> OTHER INFORMATION: Synthetic sequence, primer IF-GII4Syd12VP1.r

<400> SEQUENCE: 78
actaaagaaa ataggccttc agacagccct gcgtctgcca gtcccatt                  48

<210> SEQ ID NO 79
<211> LENGTH: 48
<212> TYPE: DNA
<213> ORGANISM: Artificial Sequence
<220> FEATURE:
<223> OTHER INFORMATION: Synthetic sequence, primer
      GII.4Syd15(opt1)(P80S).r

<400> SEQUENCE: 79
gtcggggccg agggaggcgc tccacagtat ctctccagga gcgtttct                  48

<210> SEQ ID NO 80
<211> LENGTH: 47
<212> TYPE: DNA
<213> ORGANISM: Artificial Sequence
<220> FEATURE:
<223> OTHER INFORMATION: Synthetic sequence, primer
    GII.4Syd15(opt1)(P80S).c

<400> SEQUENCE: 80
gatactgtgg agcgcctccc tcggccccga cctcaacccc tatctgt                47

<210> SEQ ID NO 81
<211> LENGTH: 49
<212> TYPE: DNA
<213> ORGANISM: Artificial Sequence
<220> FEATURE:
<223> OTHER INFORMATION: Synthetic sequence, primer
    GII.4Syd15(opt1)+GII.4Syd12.r

<400> SEQUENCE: 81
ggcttagttc tgctctcaac agtgggggc actaagaaga taaagtcaa              49

<210> SEQ ID NO 82
<211> LENGTH: 49
<212> TYPE: DNA
<213> ORGANISM: Artificial Sequence
<220> FEATURE:
<223> OTHER INFORMATION: Synthetic sequence, primer
    GII.4Syd12+GII.4Syd15(opt1).c

<400> SEQUENCE: 82 tgcccccac tgttgagagc agaactaagc cctttctgt tcccgtgct                49

<210> SEQ ID NO 83
<211> LENGTH: 48
<212> TYPE: DNA
<213> ORGANISM: Artificial Sequence
<220> FEATURE:
<223> OTHER INFORMATION: Synthetic sequence, primer
    GII.4Syd15(opt1)(M333V).r

<400> SEQUENCE: 83
cgtctgtgtc agcacgccct ggatctttcc aacaaagtcg ggtgtccc               48

<210> SEQ ID NO 84
<211> LENGTH: 49
<212> TYPE: DNA
<213> ORGANISM: Artificial Sequence
<220> FEATURE:
<223> OTHER INFORMATION: Synthetic sequence, primer
    GII.4Syd15(opt1)(M333V).c

<400> SEQUENCE: 84
tggaaagatc cagggcgtgc tgacacagac gacaaagaca gatggttca             49

<210> SEQ ID NO 85
<211> LENGTH: 49
<212> TYPE: DNA
<213> ORGANISM: Artificial Sequence
<220> FEATURE:
<223> OTHER INFORMATION: Synthetic sequence, primer
    GII.4Syd15(opt1)(Q368E).r

<400> SEQUENCE: 85
atctgtatct gtctcaaact gcactctacc gagttttggt gcgaaatcg              49

<210> SEQ ID NO 86
<211> LENGTH: 49
<212> TYPE: DNA
<213> ORGANISM: Artificial Sequence
<220> FEATURE:
<223> OTHER INFORMATION: Synthetic sequence, primer
GII.4Syd15(opt1)(Q368E).c

<400> SEQUENCE: 86
cggtagagtg cagtttgaga cagatacaga tcacgacttt gaagccaac        49

<210> SEQ ID NO 87
<211> LENGTH: 54
<212> TYPE: DNA
<213> ORGANISM: Artificial Sequence
<220> FEATURE:
<223> OTHER INFORMATION: Synthetic sequence, primer
VP1_GII.4Syd12(A39V).r

<400> SEQUENCE: 87
gaccggccac ggggactgct atggctgcgc ccaccacagg ctccagggcc atca    54

<210> SEQ ID NO 88
<211> LENGTH: 54
<212> TYPE: DNA
<213> ORGANISM: Artificial Sequence
<220> FEATURE:
<223> OTHER INFORMATION: Synthetic sequence, primer
VP1_GII.4Syd12(A39V).c

<400> SEQUENCE: 88
gggcgcagcc atagcagtcc ccgtggccgg tcagcagaat gtgattgacc cgtg    54

<210> SEQ ID NO 89
<211> LENGTH: 48
<212> TYPE: DNA
<213> ORGANISM: Artificial Sequence
<220> FEATURE:
<223> OTHER INFORMATION: Synthetic sequence, primer
VP1_GII.4Syd12(R53I).r

<400> SEQUENCE: 89
tggacaaaat tgttgattat ccacgggtca atcacattct gctgaccg         48

<210> SEQ ID NO 90
<211> LENGTH: 50
<212> TYPE: DNA
<213> ORGANISM: Artificial Sequence
<220> FEATURE:
<223> OTHER INFORMATION: Synthetic sequence, primer
VP1_GII.4Syd12(R53I).c

<400> SEQUENCE: 90
gattgacccg tggataatca acaatttgt ccaagcccct ggtggggagt         50

<210> SEQ ID NO 91
<211> LENGTH: 48
<212> TYPE: DNA
<213> ORGANISM: Artificial Sequence
<220> FEATURE:
<223> OTHER INFORMATION: Synthetic sequence, primer
VP1(Syd15)GII4(opt1)(A39V).r

<400> SEQUENCE: 91
tgcccagcaa caggcacagc tatagcagct ccaaccacgg gctcaagg          48

```
<210> SEQ ID NO 92
<211> LENGTH: 48
<212> TYPE: DNA
<213> ORGANISM: Artificial sequence
<220> FEATURE:
<223> OTHER INFORMATION: Synthetic sequence, primer
      VP1(Syd15)GII4(opt1)(A39V).c

<400> SEQUENCE: 92
tggagctgct atagctgtgc ctgttgctgg gcagcagaac gtgataga            48

<210> SEQ ID NO 93
<211> LENGTH: 51
<212> TYPE: DNA
<213> ORGANISM: Artificial Sequence
<220> FEATURE:
<223> OTHER INFORMATION: Synthetic sequence, primer
      VP1(Syd15)GII4(opt1)(R53I).r

<400> SEQUENCE: 93
caaagttgtt gattatccat gggtctatca cgttctgctg cccagcaaca g        51

<210> SEQ ID NO 94
<211> LENGTH: 48
<212> TYPE: DNA
<213> ORGANISM: Artificial Sequence
<220> FEATURE:
<223> OTHER INFORMATION: Synthetic sequence, primer
      VP1(Syd15)GII4(opt1)(R53I).c

<400> SEQUENCE: 94
tgatagaccc atggataatc aacaactttg ttcaggcccc cggtggag            48
```

The invention claimed is:

1. A modified norovirus VP1 protein comprising an S domain and a P domain,
wherein the S domain comprises an amino acid sequence of the S domain of a first wild type norovirus VP1 protein, wherein said sequence comprises one or more amino acid substitutions selected from the group consisting of substitutions at a position in sequence alignment with amino acids 39, 53 and 80 of a reference sequence of SEQ ID NO: 1;
wherein the P domain comprises an amino acid sequence of the P domain of a second wild type norovirus VP1 protein, wherein said sequence comprises one or more amino acid substitutions selected from the group consisting of substitutions at a position in sequence alignment with amino acids 333 and 368 of the reference sequence of SEQ ID NO: 1; or
a combination thereof, and
wherein the amino acid substitution at the position in sequence alignment with amino acid 39 is to valine, isoleucine, leucine or methionine; the amino substitution at the position in sequence alignment with amino acid 53 is to isoleucine, leucine, valine, alanine or methionine; the amino substitution at the position in sequence alignment with amino acid 80 is to serine, asparagine, cysteine or threonine; the amino substitution at the position in sequence alignment with amino acid 333 is to valine, isoleucine or leucine; and the amino substitution at the position in sequence alignment with amino acid 368 is to glutamate, asparagine or aspartate.

2. The modified norovirus VP1 protein of claim 1, wherein the first and the second wild type norovirus VP1 proteins are norovirus GII.4 VP1 proteins.

3. The modified norovirus VP1 protein of claim 1, wherein:
the S domain comprises the amino acid sequence of the S domain of Hu/GII.4/Sydney/2015 or Hu/GII.4/Sydney/NSW0514/2012/AU, and wherein the one or more amino acid substitutions in the S domain are:
an amino acid substitution at a position in sequence alignment with amino acid 80 of the reference sequence of SEQ ID NO:1;
two amino acid substitutions at positions in sequence alignment with amino acids 39 and 80 of the reference sequence of SEQ ID NO:1;
two amino acid substitutions at positions in sequence alignment with amino acids 53 and 80 of the reference sequence of SEQ ID NO:1; or
three amino acid substitutions at positions in sequence alignment with amino acids 39, 53 and 80 of the reference sequence of SEQ ID NO:1.

4. The modified norovirus VP1 protein of claim 3, wherein the one or more amino acid substitution in the P domain are:
an amino acid substitution at a position in sequence alignment with amino acid 333 of the reference sequence of SEQ ID NO: 1;
an amino acid substitution at a position in sequence alignment with amino acid 368 of the reference sequence of SEQ ID NO: 1; or
two amino acid substitutions at positions in sequence alignment with amino acids 333 and 368 of the reference sequence of SEQ ID NO: 1.

5. A recombinant nucleic acid encoding the modified norovirus VP1 protein of claim 1.

6. The recombinant nucleic acid of claim 5, wherein codon usage is optimized to human codon usage, increased GC content, or a combination thereof.

7. A vector comprising the nucleic acid of claim 5.

8. A virus-like particle (VLP) comprising the modified norovirus VP1 of claim 1.

9. A method of producing a modified norovirus VP1 protein, or a norovirus virus like particle (VLP), in a plant, portion of a plant or a plant cell, comprising:
introducing the nucleic acid of claim 5 into the plant, portion of the plant or the plant cell; and
incubating the plant, the portion of the plant or the plant cell under conditions that permit expression of the modified norovirus VP1 protein.

10. The modified norovirus VP1 protein or the norovirus VLP produced by the method of claim 9.

11. A plant, portion of the plant, or plant cell comprising the modified norovirus VP1 protein of claim 1.

12. A plant, portion of the plant, or plant cell comprising the VLP of claim 8.

13. A plant extract comprising the modified norovirus VP1 protein produced by the method of claim 9.

14. A plant extract comprising the norovirus VLP produced by the method of claim 9.

15. A composition for inducing an immune response comprising, an effective dose of the VLP of claim 8, and a pharmaceutically acceptable carrier, adjuvant, vehicle or excipient.

16. A vaccine comprising an effective dose of the modified norovirus VP1 protein of claim 1, for inducing an immune response.

17. A method for inducing immunity to a norovirus infection in a subject, the method comprising administering the VLP of claim 8 to the subject.

18. A method of increasing the yield of a norovirus virus like particle (VLP) in a plant, portion of a plant or a plant cell, comprising:
introducing the nucleic acid of claim 5 into the plant, portion of the plant, or the plant cell; and
incubating the plant, portion of the plant or the plant cell under conditions that permit expression of the modified norovirus VP1 protein, thereby producing the norovirus VLP;
wherein the yield of the norovirus VLP comprising the modified norovirus VP1 protein is greater than the yield of a norovirus VLP comprising a wild type norovirus VP1 protein produced in the plant, portion of the plant or the plant cell, under the same conditions.

19. The modified norovirus VP1 protein of claim 2, wherein the first and the second wild type norovirus VP1 proteins are selected from the group consisting of GII.4/Sydney/NSW0514/2012/AU (SEQ ID NO:1), Hu/GII.4/Sydney/2015 (SEQ ID NO:3), US96/GII.4/Dresden174/1997/DE_AY741811 (SEQ ID NO:5), FH02/GII.4/FarmingtonHills/2002/US_AY502023 (SEQ ID NO:6), Hnt04:GII.4/Hunter-NSW504D/2004/AU_DQ078814 (SEQ ID NO:7), 2006b: GII.4/Shellharbour-NSW696T/2006/AU_EF684915 (SEQ ID NO:8) and NO09: GII.4/Orange-NSW001P/2008/AU_GQ845367 (SEQ ID NO:9).

20. The method of claim 9, further comprising the steps of:
harvesting the plant, portion of the plant, or the plant cell; and
extracting, purifying, or both extracting and purifying the modified norovirus VP1 protein or VLP from the plant, portion of the plant or the plant cell.

21. The method of claim 17, wherein the VLP is administered to the subject orally, intranasally, intramuscularly, intraperitoneally, intravenously, subcutaneously, rectally, or intravaginally.

22. A modified norovirus VP1 protein comprising an S domain and a P domain,
wherein the S domain comprises an amino acid substitution at a position in a sequence alignment with amino acid 80 of the reference sequence of SEQ ID NO:1, wherein the amino acid substitution is to serine, asparagine, cysteine or threonine; and
wherein the P domain comprises one or more of:
an amino acid substitution at a position in a sequence alignment with amino acid 333 of the reference sequence of SEQ ID NO: 1, wherein the amino acid substitution is to valine, isoleucine or leucine; and
an amino acid substitution at a position in sequence alignment with amino acid 368 of the reference sequence of SEQ ID NO: 1, wherein the amino acid substitution is to glutamate, asparagine or aspartate; or a combination thereof.

\* \* \* \* \*